United States Patent
Yamamoto et al.

(10) Patent No.: US 10,074,813 B2
(45) Date of Patent: Sep. 11, 2018

(54) ORGANIC SEMICONDUCTOR COMPOSITION AND METHOD FOR MANUFACTURING ORGANIC SEMICONDUCTOR ELEMENT

(71) Applicant: FUJIFILM CORPORATION, Minato-ku, Tokyo (JP)

(72) Inventors: Yosuke Yamamoto, Kanagawa (JP); Yushi Hongo, Kanagawa (JP); Kensuke Masui, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 15/648,463

(22) Filed: Jul. 13, 2017

(65) Prior Publication Data
US 2017/0317296 A1 Nov. 2, 2017

Related U.S. Application Data

(63) Continuation of application No. PCT/JP2016/058257, filed on Mar. 16, 2016.

(30) Foreign Application Priority Data

Mar. 17, 2015 (JP) .................... 2015-053206

(51) Int. Cl.
*H01L 29/08* (2006.01)
*H01L 35/24* (2006.01)
(Continued)

(52) U.S. Cl.
CPC ........ *H01L 51/0074* (2013.01); *C07D 495/22* (2013.01); *C09D 11/03* (2013.01);
(Continued)

(58) Field of Classification Search
CPC . H01L 51/00; H01L 51/0074; H01L 51/0071; H01L 51/0068; H01L 51/0094;
(Continued)

(56) References Cited

U.S. PATENT DOCUMENTS

2008/0258613 A1* 10/2008 Fukuoka ............. H01L 51/5012
313/504
2010/0200841 A1 8/2010 Cheon
(Continued)

FOREIGN PATENT DOCUMENTS

JP 2006-287224 A 10/2006
JP 2012-517673 A 8/2012
(Continued)

OTHER PUBLICATIONS

Extended European Search Report dated Jan. 3, 2018, issued in corresponding EP Patent Application No. 16764999.5.
(Continued)

*Primary Examiner* — Charles Garber
*Assistant Examiner* — Abdulfattah Mustapha
(74) *Attorney, Agent, or Firm* — SOLARIS Intellectual Property Group, PLLC

(57) ABSTRACT

An object of the present invention is to provide an organic semiconductor composition, which makes it possible to obtain an organic semiconductor film having high mobility and being excellent in film uniformity and heat resistance, and a method for manufacturing an organic semiconductor element.
The organic semiconductor composition of the present invention contains an organic semiconductor as Component A and an organic solvent, which is represented by Formula B-1 and has a melting point of equal to or lower than 25° C. and a boiling point of equal to or higher than 150° C. and
(Continued)

equal to or lower than 280° C., as Component B, in which an ionization potential of Component A is equal to or higher than 5.1 eV. In the formula, X represents O, S, S=O, O=S=O, or NR, $Y_1$ to $Y_4$ each independently represent $NR_1$ or $CR_{10}R_{11}$, R, $R_1$, $R_{10}$, and $R_{11}$ each independently represent a hydrogen atom or a substituent, and n represents 1 or 2.

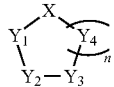

(B-1)

13 Claims, 1 Drawing Sheet

(51) Int. Cl.
*H01L 51/00* (2006.01)
*C07D 495/22* (2006.01)
*H01L 29/786* (2006.01)
*H01L 51/05* (2006.01)
*C09D 11/03* (2014.01)
*C09D 11/033* (2014.01)
*C09D 11/102* (2014.01)
*C09D 11/36* (2014.01)
*C09D 11/38* (2014.01)
*C09D 11/52* (2014.01)

(52) U.S. Cl.
CPC .......... *C09D 11/033* (2013.01); *C09D 11/102* (2013.01); *C09D 11/36* (2013.01); *C09D 11/38* (2013.01); *C09D 11/52* (2013.01); *H01L 29/786* (2013.01); *H01L 51/0036* (2013.01); *H01L 51/0068* (2013.01); *H01L 51/0069* (2013.01); *H01L 51/0071* (2013.01); *H01L 51/0072* (2013.01); *H01L 51/0073* (2013.01); *H01L 51/0094* (2013.01); *H01L 51/05* (2013.01)

(58) Field of Classification Search
CPC . H01L 51/0073; H01L 51/0069; C09D 11/03; C09D 11/52; C09D 11/38; C09D 11/36; C09D 11/102
See application file for complete search history.

(56) References Cited

U.S. PATENT DOCUMENTS

| | | |
|---|---|---|
| 2010/0323464 A1 | 12/2010 | Cheon et al. |
| 2012/0205637 A1 | 8/2012 | Cheon et al. |
| 2013/0098449 A1* | 4/2013 | Okubo .................. B82Y 10/00 136/263 |
| 2015/0166560 A1 | 6/2015 | Kitamura et al. |
| 2016/0013429 A1 | 1/2016 | Takaku et al. |
| 2016/0049592 A1 | 2/2016 | Yonekuta et al. |

FOREIGN PATENT DOCUMENTS

| | | |
|---|---|---|
| JP | 2013-516052 A | 5/2013 |
| WO | 2014/034393 A1 | 3/2014 |
| WO | 2014/148614 A1 | 9/2014 |
| WO | 2014/156878 A1 | 10/2014 |

OTHER PUBLICATIONS

English language translation of the following: Office action dated Feb. 27, 2018 from the JPO in a Japanese patent application No. 2017-506577 corresponding to the instant patent application.

* cited by examiner

ORGANIC SEMICONDUCTOR COMPOSITION AND METHOD FOR MANUFACTURING ORGANIC SEMICONDUCTOR ELEMENT

CROSS-REFERENCE TO RELATED APPLICATIONS

This application is a Continuation of International Application No. PCT/JP2016/058257 filed on Mar. 16, 2016, which claims priority to Japanese Patent Application No. 2015-053206 filed on Mar. 17, 2015. The entire contents of these applications are incorporated herein by reference.

BACKGROUND OF THE INVENTION

1. Field of the Invention

The present invention relates to an organic semiconductor composition and a method for manufacturing an organic semiconductor element.

2. Description of the Related Art

An organic transistor having an organic semiconductor film (organic semiconductor layer) is used in a field effect transistor (FET) used in a liquid crystal display or an organic electroluminescence (EL) display, a radio frequency identifier (RFID, RF tag), and the like, because the use of the organic transistor makes it possible to achieve weight lightening, cost reduction, and flexibilization.

As the method for preparing an organic semiconductor film, various methods are suggested.

For example, JP2006-287224A describes a film forming method which is for forming a film of a polythiophene semiconductor on a substrate, including (1) step of dissolving the polythiophene semiconductor in a solvent containing halogen-containing aromatic compound and (2) step of printing the obtained solution on the substrate by using an ink jet.

JP2013-516052A describes a composition containing one or more organic semiconductor compounds (OSC), one or more organic solvents, and one or more additives (wetting agents) reducing the surface tension of the composition, in which the wetting agents are volatile and can chemically react with the organic semiconductor compounds.

SUMMARY OF THE INVENTION

An object of the present invention is to provide an organic semiconductor composition, which makes it possible to obtain an organic semiconductor film having high mobility and being excellent in film uniformity and heat resistance, and a method for manufacturing an organic semiconductor element.

The aforementioned object of the present invention was achieved by means described below in <1> or <12>. Preferred embodiments are also described below in <2> to <11> and <13>.

<1> An organic semiconductor composition comprising an organic semiconductor as Component A, an organic solvent, which is represented by Formula B-1 and has a melting point of equal to or lower than 25° C. and a boiling point of equal to or higher than 150° C. and equal to or lower than 280° C., as Component B, in which an ionization potential of Component A is equal to or higher than 5.1 eV.

In Formula B-1, X represents O, S, S=O, O=S=O, or NR; $Y_1$ to $Y_4$ each independently represent $NR_1$ or $CR_{10}R_{11}$; R, $R_1$, $R_{10}$, and $R_{11}$ each independently represent a hydrogen atom or a substituent; n represents 1 or 2; in a case where n is 2, two $Y_4$'s may be the same as or different from each other; in a case where X is NR, a substituent on $Y_1$ or $Y_4$ and the substituent R on N may form a ring or may form a double bond in a 5-membered or 6-membered ring containing X by being bonded to each other; substituents of $Y_1$ to $Y_4$ adjacent to each other may form a ring or may form a double bond in a 5-membered or 6-membered ring containing X by being bonded to each other; and in a case where X is O, a substituent of $Y_1$ and a substituent of $Y_2$ do not form a double bond by being bonded to each other.

<2> The organic semiconductor composition described in <1>, in which Component B is an organic solvent which is represented by the following Formula B-2 and has a melting point of equal to or lower than 25° C. and a boiling point of equal to or higher than 150° C. and equal to or lower than 280° C.

In Formula B-2, X represents O, S, S=O, O=S=O, or NR; n represents 1 or 2; R and $R_{20}$ to $R_{27}$ each independently represent a hydrogen atom or a substituent; in a case where n is 2, two $R_{26}$'s and two $R_{27}$'s may be the same as or different from each other; two out of R and $R_{20}$ to $R_{27}$ may form a ring by being bonded to each other; R and $R_{20}$, $R_{20}$ and $R_{22}$, $R_{22}$ and $R_{24}$, and $R_{24}$ and $R_{26}$ may form a double bond in a 5-membered or 6-membered ring containing X by being bonded to each other; and in a case where X is O, $R_{20}$ and $R_{22}$ do not form a double bond by being bonded to each other.

<3> The organic semiconductor composition described in <1> or <2>, in which Component B is an organic solvent which is represented by any one of the following Formulae B-3 to B-6 and has a melting point of equal to or lower than 25° C. and a boiling point of equal to or higher than 150° C. and equal to or lower than 280° C.

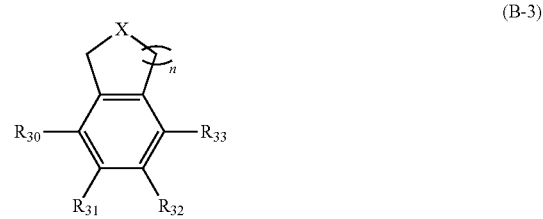

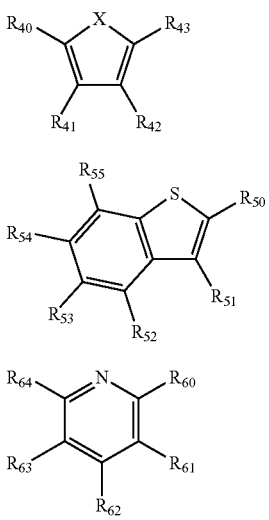

(B-4)

(B-5)

(B-6)

In Formulae B-3 to B-6, X represents an oxygen atom or a sulfur atom; n represents 1 or 2; $R_{30}$ to $R_{33}$, $R_{40}$ to $R_{43}$, $R_{50}$ to $R_{55}$, and $R_{60}$ to $R_{64}$ each independently represent a hydrogen atom or a substituent; at least one of $R_{40}$, $R_{41}$, $R_{42}$, or $R_{43}$ represents a halogen atom; and $R_{60}$ and $R_{61}$ and $R_{61}$ and $R_{62}$ may form a ring by being linked to each other.

<4> The organic semiconductor composition described in any one of <1> to <3>, in which Component A has a condensed polycyclic aromatic group, the number of rings in the condensed polycyclic aromatic group is equal to or greater than 4, at least one ring in the condensed polycyclic aromatic group is a heterocyclic ring, and at least one structure selected from the group consisting of a benzene ring, a naphthalene ring, and a phenanthrene ring is contained as a partial structure in the condensed polycyclic aromatic group.

<5> The organic semiconductor composition described in <4>, in which the number of rings in the condensed polycyclic aromatic group is 5 or 6.

<6> The organic semiconductor composition described in any one of <1> to <5>, in which Component A contains at least one kind of compound represented by any one of Formulae 1 to 16.

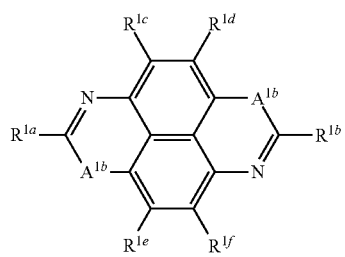

(1)

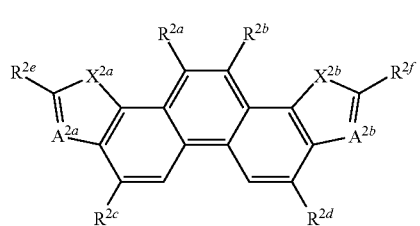

(2)

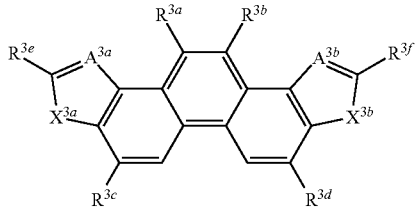

(3)

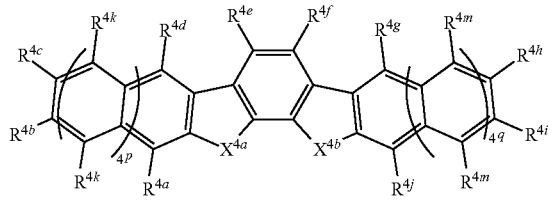

(4)

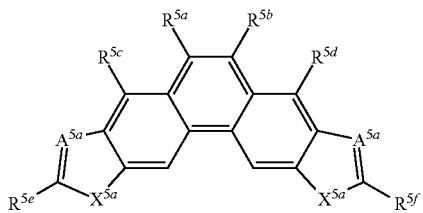

(5)

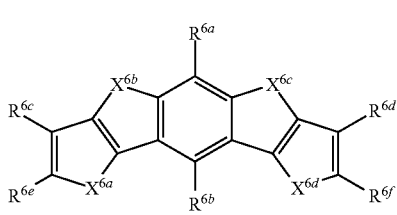

(6)

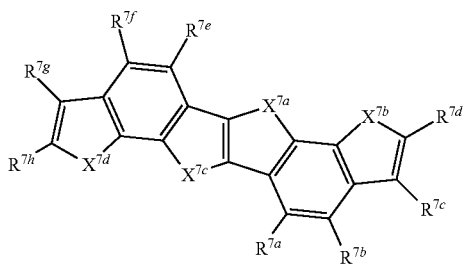

(7)

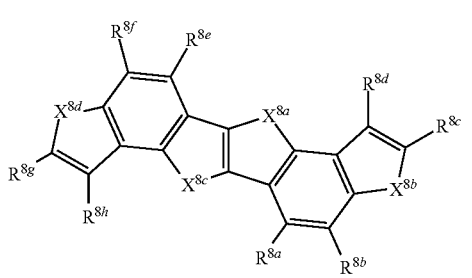

(8)

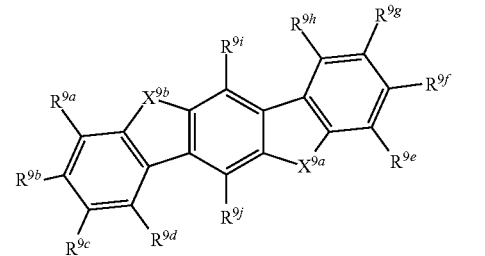
(9)

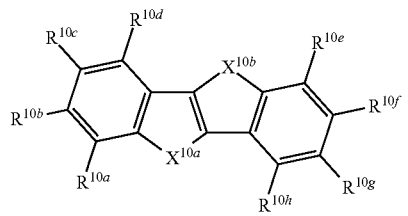
(10)

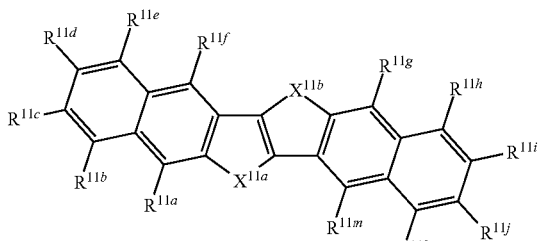
(11)

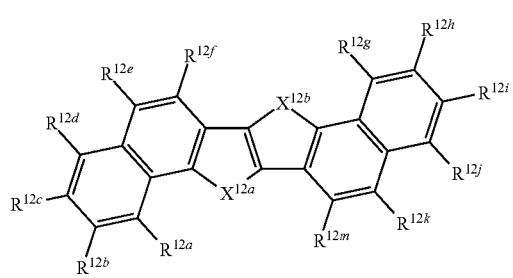
(12)

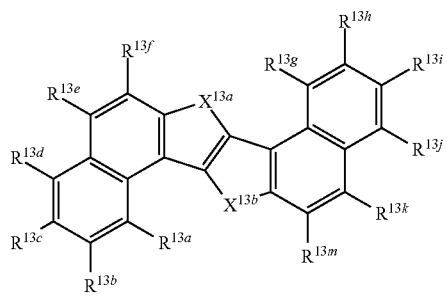
(13)

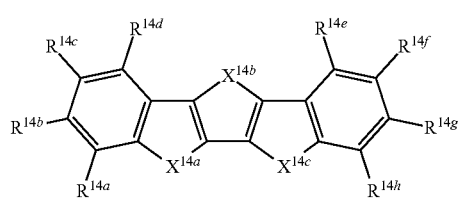
(14)

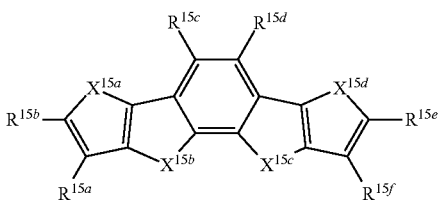
(15)

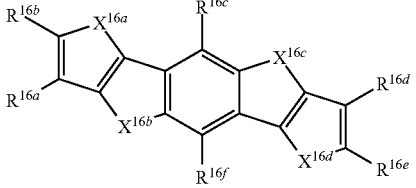
(16)

In Formula 1, $A^{1a}$ and $A^{1b}$ each independently represent a S atom, an O atom, or a Se atom, $R^{1a}$ to $R^{1f}$ each independently represent a hydrogen atom or a substituent, and at least one of $R^{1a}$, $R^{1b}$, $R^{1c}$, $R^{1d}$, $R^{1e}$, or $R^{1f}$ is a group represented by the following Formula W.

$$-L^W-R^W \quad (W)$$

In Formula W, $L^W$ represents a divalent linking group represented by any one of the following Formulae L-1 to L-25 or a divalent linking group in which 2 or more divalent linking groups represented by any one of the following Formulae L-1 to L-25 are bonded to each other, and $R^W$ represents an alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having 2 or more silicon atoms, or a trialkylsilyl group.

(L-1)

(L-2)

(L-3)

(L-4)

(L-5)

(L-6)

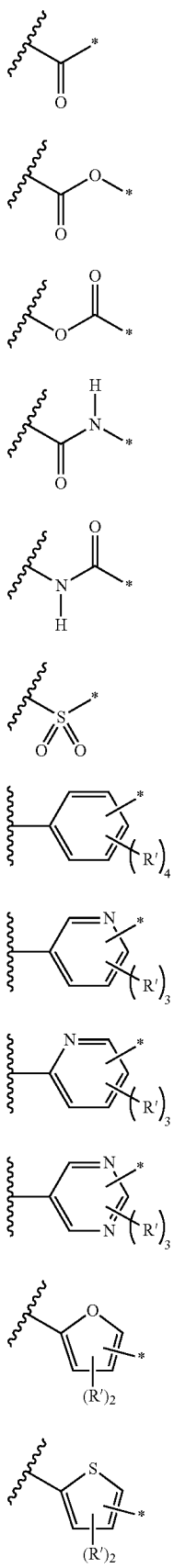
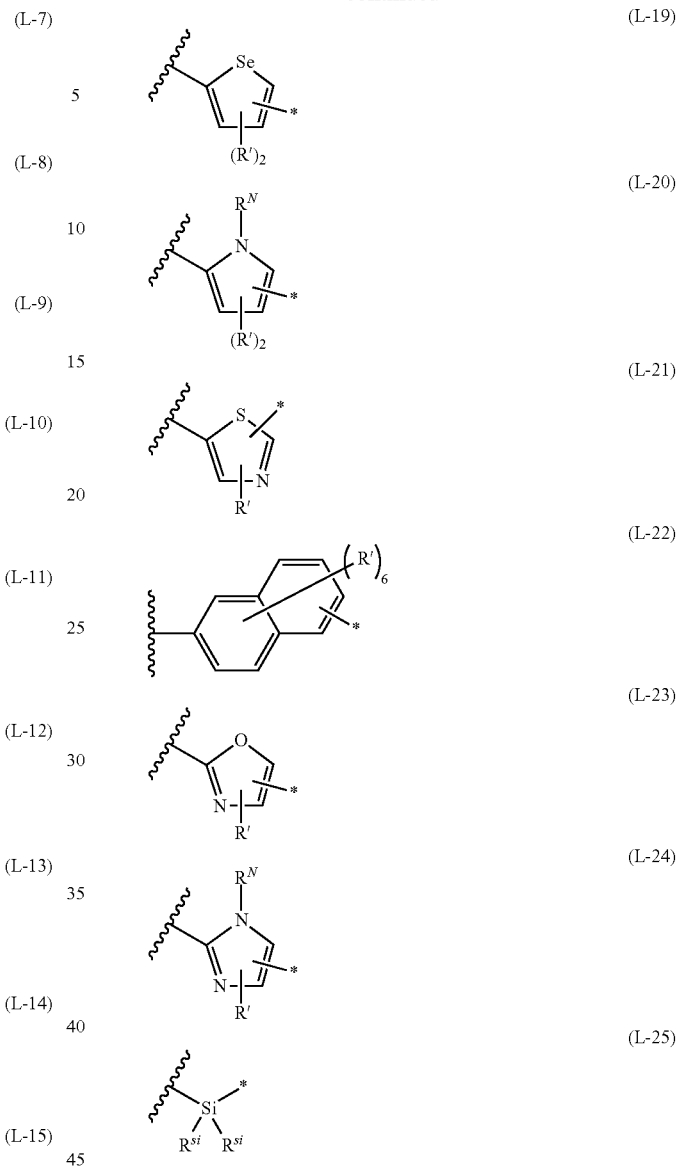

In Formulae L-1 to L-25, * represents a bonding position with respect to $R^W$, the portion of a wavy line represents a bonding position on the other side, R' in Formulae L-1, L-2, L-6, and L-13 to L-24 each independently represents a hydrogen atom or a substituent, $R^N$ in Formulae L-20 and L-24 represents a hydrogen atom or a substituent, and $R^{si}$ in Formula L-25 each independently represents a hydrogen atom, an alkyl group, an alkenyl group, or an alkynyl group.

In Formula 2, $X^{2a}$ and $X^{2b}$ each independently represent $NR^{2i}$, an O atom, or a S atom, $A^{2a}$ represents $CR^{2g}$ or a N atom, $A^{2b}$ represents $CR^{2h}$ or a N atom, $R^{2i}$ represents a hydrogen atom, an alkyl group, an alkenyl group, an alkynyl group, or an acyl group, $R^{2a}$ to $R^{2h}$ each independently represent a hydrogen atom or a substituent, and at least one of $R^{2a}$, $R^{2b}$, $R^{2c}$, $R^{2d}$, $R^{2e}$, $R^{2f}$, $R^{2g}$, or $R^{2h}$ is a group represented by Formula W.

In Formula 3, $X^{3a}$ and $X^{3b}$ each independently represent a S atom, an O atom, or $NR^{3g}$, and $A^{3a}$ and $A^{3b}$ each independently represent $CR^{3h}$ or a N atom. $R^{3a}$ to $R^{3b}$ each independently represent a hydrogen atom or a substituent, and at least one of $R^{3a}$, $R^{3b}$, $R^{3c}$, $R^{3d}$, $R^{3e}$, $R^{3f}$, $R^{3g}$, or $R^{3h}$ is a group represented by Formula W.

In Formula 4, $X^{4a}$ and $X^{4b}$ each independently represent an O atom, a S atom, or a Se atom, 4p and 4q each independently represent an integer of 0 to 2, $R^{4a}$ to $R^{4j}$, $R^{4k}$, and $R^{4m}$ each independently represent a hydrogen atom, a halogen atom, or a group represented by Formula W, and at least one of $R^{4a}$, $R^{4b}$, $R^{4c}$, $R^{4d}$, $R^{4e}$, $R^{4f}$, $R^{4g}$, $R^{4h}$, $R^{4i}$, $R^{4j}$, $R^{4k}$, or $R^{4m}$ is a group represented by Formula W. Here, in a case where at least one of $R^{4e}$ or $R^{4f}$ is a group represented by Formula W, $L^W$ in Formula W represented by $R^{4e}$ and $R^{4f}$ is a divalent linking group represented by Formula L-2 or L-3.

In Formula 5, $X^{5a}$ and $X^{5b}$ each independently represent $NR^{5i}$, an O atom, or a S atom, $A^{5a}$ represents $CR^{5g}$ or a N atom, $A^{5b}$ represents $CR^{5h}$ or a N atom, $R^{5i}$ represents a hydrogen atom, an alkyl group, an alkenyl group, an alkynyl group, an acyl group, an aryl group, or a heteroaryl group, $R^{5a}$ to $R^{5h}$ each independently represent a hydrogen atom or a substituent, and at least one of $R^{5a}$, $R^{5b}$, $R^{5c}$, $R^{5d}$, $R^{5e}$, $R^{5f}$, $R^{5g}$, or $R^{5h}$ is a group represented by Formula W.

In Formula 6, $X^{6a}$ to $X^{6d}$ each independently represent $NR^{6g}$, an O atom, or a S atom, $R^{6g}$ represents a hydrogen atom, an alkyl group, an alkenyl group, an alkynyl group, an acyl group, an aryl group, or a heteroaryl group, $R^{6a}$ to $R^{6f}$ each independently represent a hydrogen atom or a substituent, and at least one of $R^{6a}$, $R^{6b}$, $R^{6c}$, $R^{6d}$, $R^{6e}$, or $R^{6f}$ is a group represented by Formula W.

In Formula 7, $X^{7a}$ and $X^{7c}$ each independently represent a S atom, an O atom, a Se atom, or $NR^{7i}$, $X^{7b}$ and $X^{7d}$ each independently represent a S atom, an O atom, or a Se atom, $R^{7a}$ to $R^{7i}$ each independently represent a hydrogen atom or a substituent, and at least one of $R^{7a}$, $R^{7b}$, $R^{7c}$, $R^{7d}$, $R^{7e}$, $R^{7f}$, $R^{7g}$, $R^{7h}$, or $R^{7i}$ is a group represented by Formula W.

In Formula 8, $X^{8a}$ and $X^{8c}$ each independently represent a S atom, an O atom, a Se atom, or $NR^{8i}$, $X^{8b}$ and $X^{8d}$ each independently represent a S atom, an O atom, or a Se atom, $R^{8a}$ to $R^{8i}$ each independently represent a hydrogen atom or a substituent, and at least one of $R^{8a}$, $R^{8b}$, $R^{8c}$, $R^{8d}$, $R^{8e}$, $R^{8f}$, $R^{8g}$, $R^{8h}$, or $R^{8i}$ is a group represented by Formula W.

In Formula 9, $X^{9a}$ and $X^{9b}$ each independently represent an O atom, a S atom, or a Se atom, $R^{9c}$, $R^{9d}$, and $R^{8g}$ to $R^{9j}$ each independently represent a hydrogen atom, a halogen atom, or a group represented by Formula W, and $R^{9a}$, $R^{9b}$, $R^{9e}$, and $R^{9f}$ each independently represent a hydrogen atom or a substituent.

In Formula 10, $R^{10a}$ to $R^{10h}$ each independently represent a hydrogen atom or a substituent, at least one of $R^{10a}$, $R^{10b}$, $R^{10c}$, $R^{10d}$, $R^{10e}$, $R^{10f}$, $R^{10g}$, or $R^{10h}$ represents a substituent represented by Formula W, $X^{10a}$ and $X^{10b}$ each independently represent a S atom, an O atom, a Se atom, or $NR^{10i}$, and $R^{10i}$ each independently represents a hydrogen atom or a group represented by Formula W.

In Formula 11, $X^{11a}$ and $X^{11b}$ each independently represent a S atom, an O atom, a Se atom, or $NR^{11n}$, $R^{11a}$ to $R^{11k}$, $R^{11m}$, and $R^{11n}$ each independently represent a hydrogen atom or a substituent, and at least one of $R^{11a}$, $R^{11b}$, $R^{11c}$, $R^{11d}$, $R^{11e}$, $R^{11f}$, $R^{11g}$, $R^{11h}$, $R^{11i}$, $R^{11j}$, $R^{11k}$, $R^{11m}$, or $R^{12n}$ is a group represented by Formula W.

In Formula 12, $X^{12a}$ and $X^{12b}$ each independently represent a S atom, an O atom, a Se atom, or $NR^{12n}$, $R^{12a}$ to $R^{12k}$, $R^{12m}$, and $R^{12n}$ each independently represent a hydrogen atom or a substituent, and at least one of $R^{12a}$, $R^{12b}$, $R^{12c}$, $R^{12d}$, $R^{12e}$, $R^{12f}$, $R^{12g}$, $R^{12h}$, $R^{12i}$, $R^{12j}$, $R^{12k}$, $R^{12m}$, or $R^{12n}$ is a group represented by Formula W.

In Formula 13, $X^{13a}$ and $X^{13b}$ each independently represent a S atom, an O atom, a Se atom, or $NR^{13n}$, $R^{13a}$ to $R^{13k}$, $R^{13m}$, and $R^{13n}$ each independently represent a hydrogen atom or a substituent, and at least one of $R^{13a}$, $R^{13b}$, $R^{13c}$, $R^{13d}$, $R^{13e}$, $R^{13f}$, $R^{13g}$, $R^{13h}$, $R^{13i}$, $R^{13j}$, $R^{13k}$, $R^{13m}$, or $R^{13n}$ is a group represented by Formula W.

In Formula 14, $X^{14a}$ to $X^{14c}$ each independently represent a S atom, an O atom, a Se atom, or $NR^{14i}$, $R^{14a}$ to $R^{14i}$ each independently represent a hydrogen atom or a substituent, and at least one of $R^{14a}$, $R^{14b}$, $R^{14c}$, $R^{14d}$, $R^{14e}$, $R^{14f}$, $R^{14g}$, $R^{14h}$, or $R^{14i}$ is a group represented by Formula W.

In Formula 15, $X^{15a}$ to $X^{15d}$ each independently represent a S atom, an O atom, a Se atom, or $NR^{15g}$, $R^{15a}$ to $R^{15g}$ each independently represent a hydrogen atom or a substituent, and at least one of $R^{15a}$, $R^{15b}$, $R^{15c}$, $R^{15d}$, $R^{15e}$, $R^{15f}$, or $R^{15g}$ is a group represented by Formula W.

In Formula 16, $X^{16a}$ to $X^{16d}$ each independently represent a S atom, an O atom, a Se atom, or $NR^{16g}$, $R^{16a}$ to $R^{16g}$ each independently represent a hydrogen atom or a substituent, and at least one of $R^{16a}$, $R^{16b}$, $R^{16c}$, $R^{16d}$, $R^{16e}$, $R^{16f}$, or $R^{16g}$ is a group represented by Formula W.

<7> The organic semiconductor composition described in any one of <1> to <6>, further comprising a polymer compound as Component C.

<8> The organic semiconductor composition described in <7>, in which a content of Component C is 0.01% to 2.0% by mass with respect to a total mass of the organic semiconductor composition.

<9> The organic semiconductor composition described in any one of <1> to <8> that has a viscosity of 2 to 50 mPa·s at 25° C.

<10> The organic semiconductor composition described in any one of <1> to <9>, in which a content of Component A is 0.2% to 5% by mass with respect to the total mass of the organic semiconductor composition.

<11> The organic semiconductor composition described in any one of <1> to <10> that is for ink jet printing and/or flexographic printing.

<12> A method for manufacturing an organic semiconductor element, comprising an application step of applying the organic semiconductor composition described in any one of <1> to <11> onto a substrate and a removing step of removing at least a portion of Component B from the applied organic semiconductor composition.

<13> The method for manufacturing an organic semiconductor element described in <12>, in which the application step is performed by ink jet printing or flexographic printing.

According to the present invention, it is possible to provide an organic semiconductor composition, which makes it possible to obtain an organic semiconductor film having high mobility and being excellent in film uniformity and heat resistance, and a method for manufacturing an organic semiconductor element.

DESCRIPTION OF THE PREFERRED EMBODIMENTS

Figure 1:
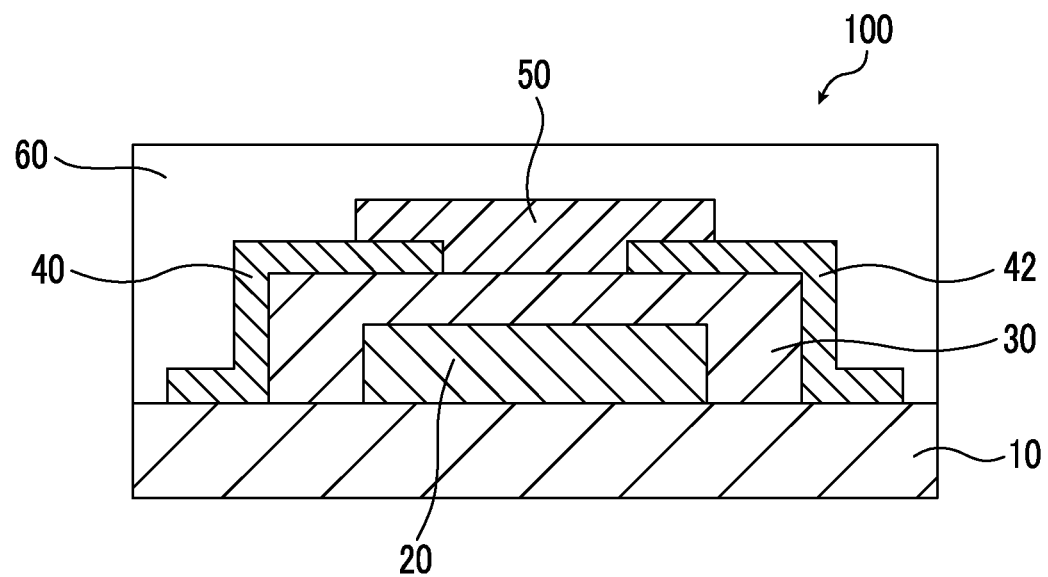
FIG. 1 is a schematic cross-sectional view of an aspect of an organic semiconductor element of the present invention.

Hereinafter, the contents of the present invention will be specifically described. The constituents in the following description will be explained based on typical embodiments of the present invention, but the present invention is not limited to the embodiments. In the specification of the present application, "to" is used to mean that the numerical values listed before and after "to" are a lower limit and an upper limit respectively. Furthermore, in the present invention, an organic EL element refers to an organic electroluminescence element.

In the present specification, in a case where there is no description regarding whether a group (atomic group) is substituted or unsubstituted, the group includes both of a group having a substituent and a group not having a substituent. For example, an "alkyl group" includes not only an alkyl group not having a substituent (unsubstituted alkyl group) but also an alkyl group having a substituent (substituted alkyl group).

In the present specification, in some cases, a chemical structural formula is described as a simplified structural formula in which a hydrogen atom is omitted.

In the present invention, the description of "mobility" refers to carrier mobility and means either or both of electron mobility and hole mobility.

In the present invention, "% by mass" and "% by weight" have the same definition, and "part by mass" and "part by weight" have the same definition.

In the present invention, a combination of two or more preferred aspects is a more preferred aspect.

(Organic Semiconductor Composition)

The organic semiconductor composition (hereinafter, simply referred to as "composition" as well) of the present invention contains an organic semiconductor as Component A and an organic solvent, which is represented by Formula B-1 and has a melting point of equal to or lower than 25° C. and a boiling point of equal to or higher than 150° C. and equal to or lower than 280° C., as Component B, in which an ionization potential of Component A is equal to or higher than 5.1 eV.

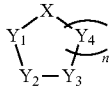

(B-1)

In Formula B-1, X represents O, S, S=O, O=S=O, or NR; $Y_1$ to $Y_4$ each independently represent $NR_1$ or $CR_{10}R_{11}$; R, $R_1$, $R_{10}$, and $R_{11}$ each independently represent a hydrogen atom or a substituent; n represents 1 or 2; in a case where n is 2, two $Y_4$'s may be the same as or different from each other; in a case where X is NR, a substituent on $Y_1$ or $Y_4$ and the substituent R on N may form a ring or may form a double bond in a 5-membered or 6-membered ring containing X by being bonded to each other; substituents of $Y_1$ to $Y_4$ adjacent to each other may form a ring or may form a double bond in a 5-membered or 6-membered ring containing X by being bonded to each other; and in a case where X is O, a substituent of $Y_1$ and a substituent of $Y_2$ do not form a double bond by being bonded to each other.

As a result of repeating a thorough examination, the inventors of the present invention found that by using an organic semiconductor composition obtained by dissolving an organic semiconductor in a specific organic solvent, it is possible to obtain an organic semiconductor film having high mobility and being excellent in film uniformity and heat resistance. Based on what they had found, the inventors accomplished the present invention.

The details of the mechanism that brings about the aforementioned effect are unclear. However, presumably, because Component B used in the present invention excellently dissolves the organic semiconductor and results in high film uniformity in a case where the organic semiconductor is crystallized, high mobility may be obtained. Furthermore, by using Component B as a solvent, the obtained organic semiconductor film hardly undergoes a change due to heat and exhibits excellent heat resistance, although the details of the mechanism are unclear.

Component A: Organic Semiconductor

The organic semiconductor composition of the present invention contains an organic semiconductor as Component A, and an ionization potential of Component A is equal to or higher than 5.1 eV.

The organic semiconductor is not particularly limited, and any organic compound (a low-molecular weight compound or a polymer) may be selected as long as the compound functions as a semiconductor. Among the organic compounds, from the viewpoint of the solubility with respect to Component B, an organic semiconductor small molecule having a condensed polycyclic aromatic group is preferable.

The ionization potential (Ip, ionization energy, referred to as dissociation energy as well) of Component A is equal to or higher than 5.1 eV.

The ionization potential of general conductive polymers such as polythiophenes (for example, poly(3-hexylthiophene-2,5-diyl) (P3HT)) is less than 5.1 eV, while the ionization potential of the organic semiconductor as a small molecule (preferably having a molecular weight of less than 1,000) which will be described later is equal to or higher than 5.1 eV.

The ionization potential is measured using AC-2 manufactured by RIKEN KIKAI Co., Ltd.

In the present invention, Component A preferably includes an organic semiconductor (hereinafter, referred to as "specific organic semiconductor" or "Component A-1" as well) having a condensed polycyclic aromatic group, in which the number of rings in the condensed polycyclic aromatic group is equal to or greater than 4, at least one ring in the condensed polycyclic aromatic group contains at least one atom selected from the group consisting of a sulfur atom, a nitrogen atom, a selenium atom, and an oxygen atom, and at least one structure selected from the group consisting of a benzene ring, a naphthalene ring, and a phenanthrene ring is contained as a partial structure in the condensed polycyclic aromatic group.

It is preferable that the partial structure in the condensed polycyclic aromatic group in Component A-1 does not contain an anthracene ring. In a case where the partial structure does not contain an anthracene ring, the mobility and the film uniformity of the obtained organic semiconductor film become excellent, although the reason is unclear.

The condensed polycyclic aromatic group is a group obtained by the condensation of a plurality of aromatic rings.

Examples of the aromatic rings include an aromatic hydrocarbon ring (for example, a benzene ring) and an aromatic heterocyclic ring (for example, a thiophene ring, a furan ring, a pyrrole ring, a selenophene ring, and an imidazole ring).

Component A-1 contains the condensed polycyclic aromatic group (condensed polycyclic aromatic structure), and it is preferable that this group is contained in Component A-1 as a main component. Herein, the "main component" means that the content of the condensed polycylcic aromatic group based on the molecular weight is equal to or greater than 30% by mass with respect to the total molecular weight of Component A. The content of the condensed polycyclic aromatic group is preferably equal to or greater than 40%.

The upper limit of the content of the condensed polycyclic aromatic group is not particularly limited, but from the viewpoint of solubility, the upper limit is preferably equal to or less than 80%.

The condensed polycyclic aromatic group is a ring structure formed by the condensation of a plurality of rings and exhibits aromaticity.

From the viewpoint of the mobility of the organic semiconductor, the condensed polycyclic aromatic group preferably contains at least 1 or more heterocyclic rings, and each of the heterocyclic rings preferably has 1 heteroatom. The type of the heteroatom is not particularly limited, and examples thereof include an oxygen atom (O atom), a sulfur atom (S atom), a nitrogen atom (N atom), a selenium atom (Se atom), and the like. Among these, a sulfur atom (S atom) and a selenium atom (Se atom) are preferable, and a sulfur atom (S atom) is more preferable.

From the viewpoint of the mobility of the organic semiconductor, Component A-1 preferably has at least a thiophene ring structure and/or a selenophene ring structure, and more preferably has at least a thiophene ring structure. It is even more preferable that a thiophene ring structure is the only heterocyclic structure that Component A-1 has.

From the viewpoint of the mobility of the organic semiconductor, the aforementioned condensed polycyclic aromatic group is preferably a condensed polycyclic aromatic group which contains at least any one structure selected from the group consisting of a benzene ring, a naphthalene ring, and a phenanthrene ring as a partial structure, and contains 1 or more thiophene rings, in which the number of rings is 4 to 6. Particularly, the condensed polycyclic aromatic group more preferably contains a benzene ring and 2 or more thiophene rings, in which the number of rings is 4 to 6.

Examples of the condensed polycyclic aromatic group preferably include a group obtained in a case where a ring (heterocyclic ring, preferably, a thiophene ring) containing at last one kind of atom selected from the group consisting of a sulfur atom, a nitrogen atom, a selenium atom, and an oxygen atom and a benzene ring are alternately condensed (fused) with each other.

From the viewpoint of the mobility of the organic semiconductor, the composition of the present invention preferably contains at least one kind of compound represented by any one of Formulae 1 to 16 as Component A-1, and more preferably contains 1 or more kinds of compounds represented by any one of Formulae 1 to 16 as Component A-1.

The composition of the present invention may contain only one kind of Component A-1 or two or more kinds of Component A-1.

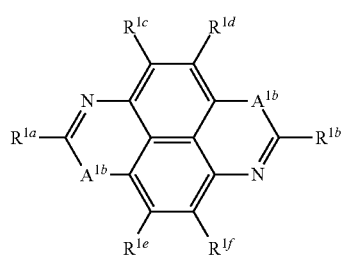

(1)

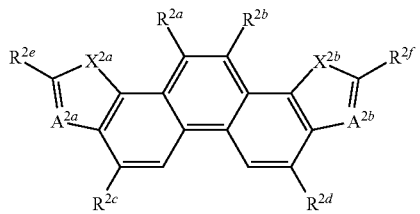

(2)

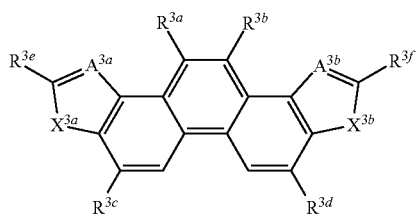

(3)

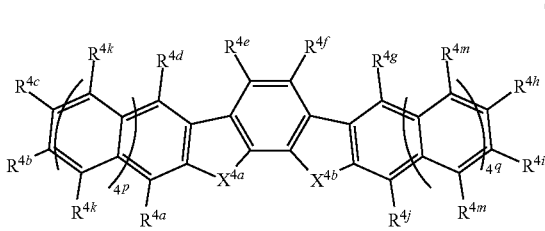

(4)

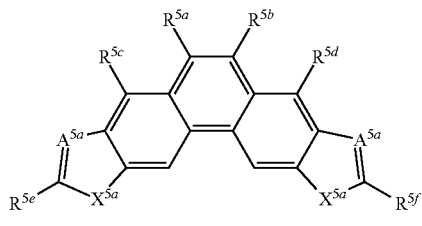

(5)

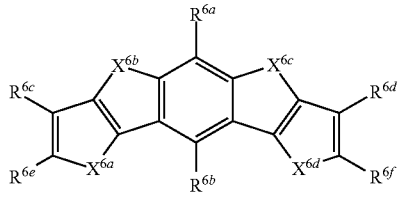

(6)

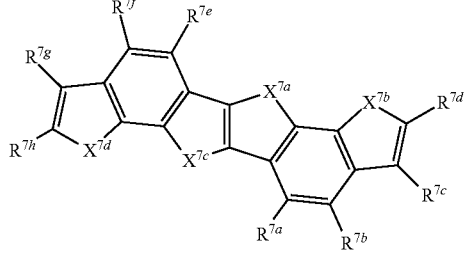

(7)

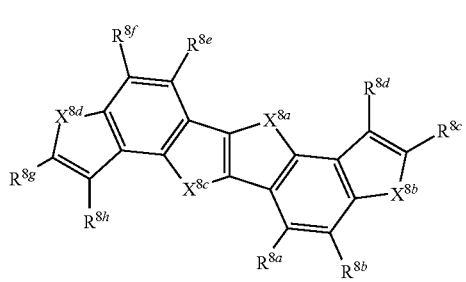

(8)

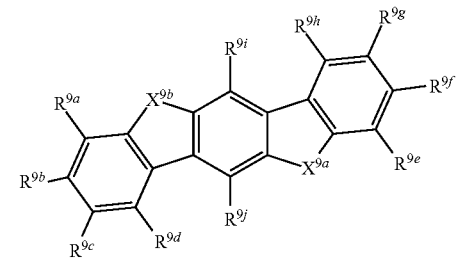
(9)

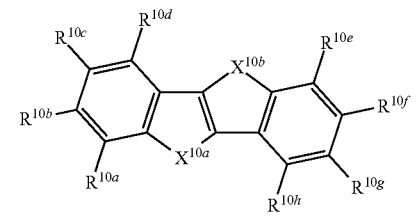
(10)

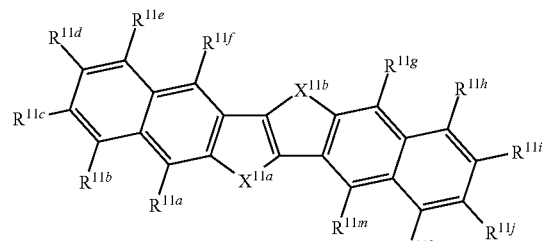
(11)

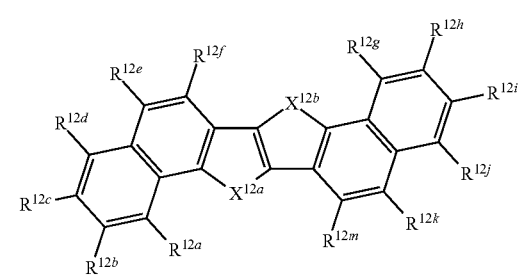
(12)

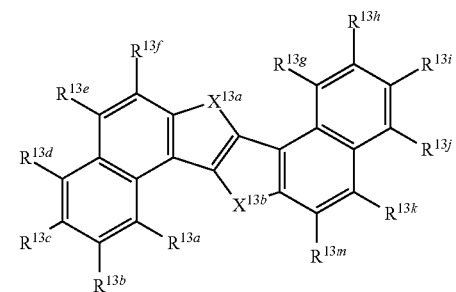
(13)

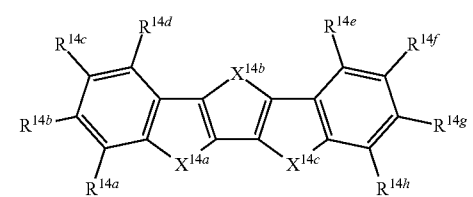
(14)

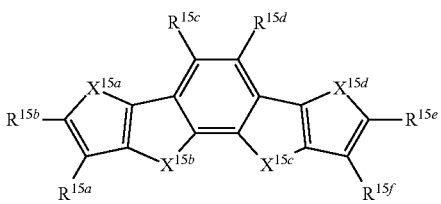
(15)

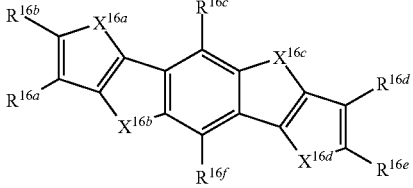
(16)

In Formula 1, $A^{1a}$ and $A^{1b}$ each independently represent a S atom, an O atom, or a Se atom, $R^{1a}$ to $R^{1f}$ each independently represent a hydrogen atom or a substituent, and at least one of $R^{1a}$, $R^{1b}$, $R^{1c}$, $R^{1d}$, $R^{1e}$, or $R^{1f}$ is a group represented by the following Formula W.

$$-L^W-R^W \qquad (W)$$

In Formula W, $L^W$ represents a divalent linking group represented by any one of the following Formulae L-1 to L-25 or a divalent linking group in which 2 or more divalent linking groups represented by any one of the following Formulae L-1 to L-25 are bonded to each other. $R^W$ represents an alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having 2 or more silicon atoms, or a trialkylsilyl group.

(L-1)

(L-2)

(L-3)

(L-4)

(L-5)

(L-6)

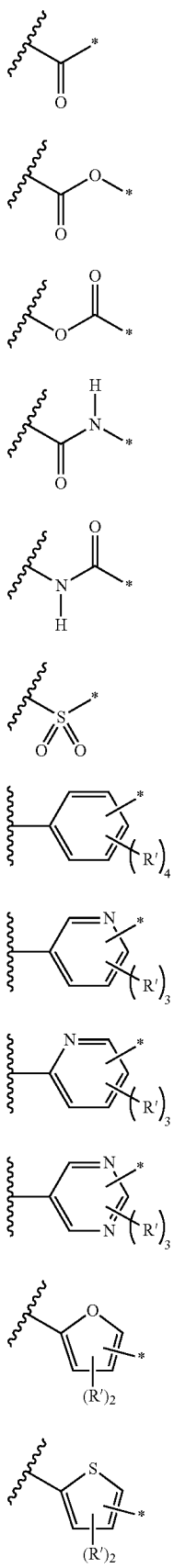
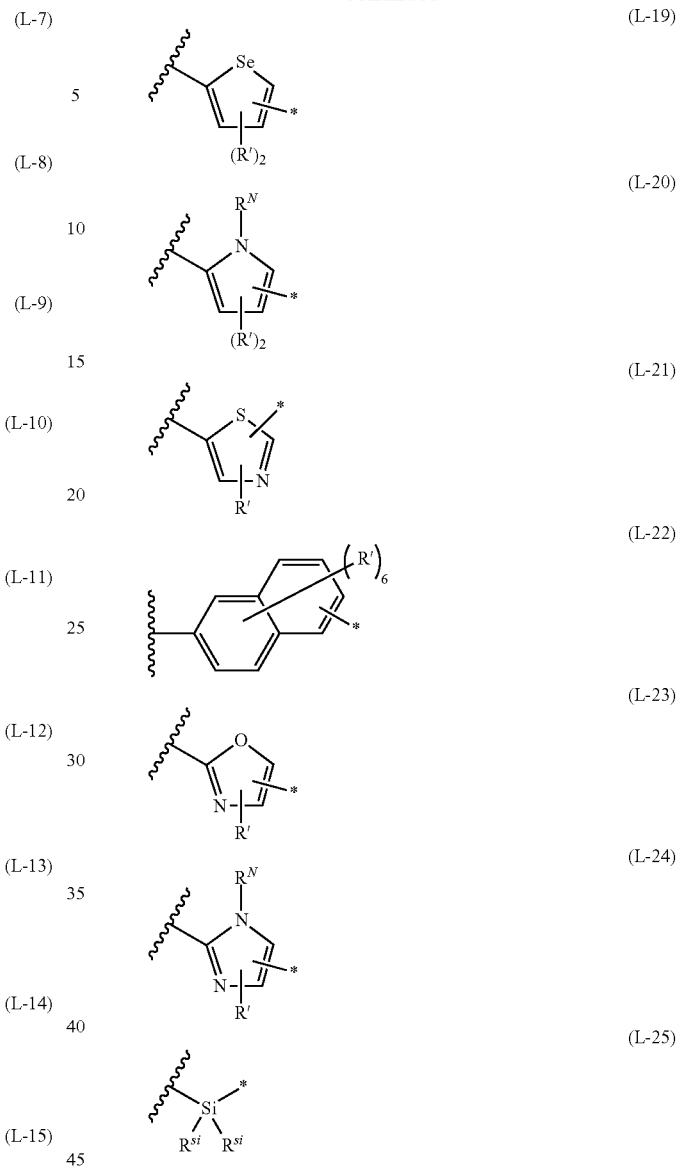

In Formulae L-1 to L-25, * represents a bonding position with respect to R, the portion of a wavy line represents a bonding position on the other side, R' in Formulae L-1, L-2, L-6, and L-13 to L-24 each independently represents a hydrogen atom or a substituent, $R^N$ in Formulae L-20 and L-24 represents a hydrogen atom or a substituent, and $R^{si}$ in Formula L-25 each independently represents a hydrogen atom, an alkyl group, an alkenyl group, or an alkynyl group.

In Formula 2, $X^{2a}$ and $X^{2b}$ each independently represent $NR^{2i}$, an O atom, or a S atom, $A^{2a}$ represents $CR^{2g}$ or a N atom, $A^{2b}$ represents $CR^{2h}$ or a N atom, $R^{2i}$ represents a hydrogen atom, an alkyl group, an alkenyl group, an alkynyl group, or an acyl group, $R^{2a}$ to $R^{2h}$ each independently represent a hydrogen atom or a substituent, and at least one of $R^{2a}$, $R^{2b}$, $R^{2c}$, $R^{2d}$, $R^{2e}$, $R^{2f}$, $R^{2g}$, or $R^{2h}$ is a group represented by Formula W.

In Formula 3, $X^{3a}$ and $X^{3b}$ each independently represent a S atom, an O atom, or $NR^{3g}$, and $A^{3a}$ and $A^{3b}$ each independently represent $CR^{3h}$ or a N atom. $R^{3a}$ to $R^{3b}$ each independently represent a hydrogen atom or a substituent, and at least one of $R^{3a}$, $R^{3b}$, $R^{3c}$, $R^{3d}$, $R^{3e}$, $R^{3f}$, $R^{3g}$, or $R^{3h}$ is a group represented by Formula W.

In Formula 4, $X^{4a}$ and $X^{4b}$ each independently represent an O atom, a S atom, or a Se atom, 4p and 4q each independently represent an integer of 0 to 2, $R^{4a}$ to $R^{4j}$, $R^{4k}$, and $R^{4m}$ each independently represent a hydrogen atom, a halogen atom, or a group represented by Formula W, and at least one of $R^{4a}$, $R^{4b}$, $R^{4c}$, $R^{4d}$, $R^{4e}$, $R^{4f}$, $R^{4g}$, $R^{4h}$, $R^{4i}$, $R^{4j}$, $R^{4k}$, or $R^{4m}$ is a group represented by Formula W. Here, in a case where at least one of $R^{4e}$ or $R^{4f}$ is a group represented by Formula W, $L^W$ in Formula W represented by $R^{4e}$ and $R^{4f}$ is a divalent linking group represented by Formula L-2 or L-3.

In Formula 5, $X^{5a}$ and $X^{5b}$ each independently represent $NR^{5i}$, an O atom, or a S atom, $A^{5a}$ represents $CR^{5g}$ or a N atom, $A^{5b}$ represents $CR^{5h}$ or a N atom, $R^{5i}$ represents a hydrogen atom, an alkyl group, an alkenyl group, an alkynyl group, an acyl group, an aryl group, or a heteroaryl group, $R^{5a}$ to $R^{5h}$ each independently represent a hydrogen atom or a substituent, and at least one of $R^{5a}$, $R^{5b}$, $R^{5c}$, $R^{5d}$, $R^{5e}$, $R^{5f}$, $R^{5g}$, or $R^{5h}$ is a group represented by Formula W.

In Formula 6, $X^{6a}$ to $X^{6d}$ each independently represent $NR^{6g}$, an O atom, or a S atom, $R^{6g}$ represents a hydrogen atom, an alkyl group, an alkenyl group, an alkynyl group, an acyl group, an aryl group, or a heteroaryl group, $R^{6a}$ to $R^{6f}$ each independently represent a hydrogen atom or a substituent, and at least one of $R^{6a}$, $R^{6b}$, $R^{6c}$, $R^{6d}$, $R^{6e}$, or $R^{6f}$ is a group represented by Formula W.

In Formula 7, $X^{7a}$ and $X^{7c}$ each independently represent a S atom, an O atom, a Se atom, or $NR^{7i}$, $X^{7b}$ and $X^{7d}$ each independently represent a S atom, an O atom, or a Se atom, $R^{7a}$ to $R^{7i}$ each independently represent a hydrogen atom or a substituent, and at least one of $R^{7a}$, $R^{7b}$, $R^{7c}$, $R^{7d}$, $R^{7e}$, $R^{7f}$, $R^{7g}$, $R^{7h}$, or $R^{7i}$ is a group represented by Formula W.

In Formula 8, $X^{8a}$ and $X^{8c}$ each independently represent a S atom, an O atom, a Se atom, or $NR^{8i}$, $X^{8b}$ and $X^{8d}$ each independently represent a S atom, an O atom, or a Se atom, $R^{8a}$ to $R^{8i}$ each independently represent a hydrogen atom or a substituent, and at least one of $R^{8a}$, $R^{8b}$, $R^{8c}$, $R^{8d}$, $R^{8e}$, $R^{8f}$, $R^{8g}$, $R^{8h}$, or $R^{8i}$ is a group represented by Formula W.

In Formula 9, $X^{9a}$ and $X^{9b}$ each independently represent an O atom, a S atom, or a Se atom, $R^{9c}$, $R^{9d}$, and $R^{9g}$ to $R^{9j}$ each independently represent a hydrogen atom, a halogen atom, or a group represented by Formula W, and $R^{9a}$, $R^{9b}$, $R^{9e}$, and $R^{9f}$ each independently represent a hydrogen atom or a substituent.

In Formula 10, $R^{10a}$ to $R^{10h}$ each independently represent a hydrogen atom or a substituent, at least one of $R^{10a}$, $R^{10b}$, $R^{10c}$, $R^{10d}$, $R^{10e}$, $R^{10f}$, $R^{10g}$, or $R^{10h}$ represents a substituent represented by Formula W, $X^{10a}$ and $X^{10b}$ each independently represent a S atom, an O atom, a Se atom, or $NR^{10i}$, and $R^{10i}$ each independently represents a hydrogen atom or a group represented by Formula W.

In Formula 11, $X^{11a}$ and $X^{11b}$ each independently represent a S atom, an O atom, a Se atom, or $NR^{11n}$, $R^{11a}$ to $R^{11k}$, $R^{11m}$, and $R^{11n}$ each independently represent a hydrogen atom or a substituent, and at least one of $R^{11a}$, $R^{11b}$, $R^{11c}$, $R^{11d}$, $R^{11e}$, $R^{11f}$, $R^{11g}$, $R^{11h}$, $R^{11i}$, $R^{11j}$, $R^{11k}$, $R^{11m}$, or $R^{11n}$ is a group represented by Formula W.

In Formula 12, $X^{12a}$ and $X^{12b}$ each independently represent a S atom, an O atom, a Se atom, or $NR^{12n}$, $R^{12a}$ to $R^{12k}$, $R^{12m}$, and $R^{12n}$ each independently represent a hydrogen atom or a substituent, and at least one of $R^{12a}$, $R^{12b}$, $R^{12c}$, $R^{12d}$, $R^{12e}$, $R^{12f}$, $R^{12g}$, $R^{12h}$, $R^{12i}$, $R^{12j}$, $R^{12k}$, $R^{12m}$, or $R^{12n}$ is a group represented by Formula W.

In Formula 13, $X^{13a}$ and $X^{13b}$ each independently represent a S atom, an O atom, a Se atom, or $NR^{13n}$, $R^{13a}$ to $R^{13k}$, $R^{13m}$, and $R^{13n}$ each independently represent a hydrogen atom or a substituent, and at least one of $R^{13a}$, $R^{13b}$, $R^{13c}$, $R^{13d}$, $R^{13e}$, $R^{13f}$, $R^{13g}$, $R^{13h}$, $R^{13i}$, $R^{13j}$, $R^{13k}$, $R^{13m}$, or $R^{13n}$ is a group represented by Formula W.

In Formula 14, $X^{14a}$ to $X^{14c}$ each independently represent a S atom, an O atom, a Se atom, or $NR^{14i}$, $R^{14a}$ to $R^{14i}$ each independently represent a hydrogen atom or a substituent, and at least one of $R^{14a}$, $R^{14b}$, $R^{14c}$, $R^{14d}$, $R^{14e}$, $R^{14f}$, $R^{14g}$, $R^{14h}$, or $R^{14i}$ is a group represented by Formula W.

In Formula 15, $X^{15a}$ to $X^{15d}$ each independently represent a S atom, an O atom, a Se atom, or $NR^{15g}$, $R^{15a}$ to $R^{15g}$ each independently represent a hydrogen atom or a substituent, and at least one of $R^{15a}$, $R^{15b}$, $R^{15c}$, $R^{15d}$, $R^{15e}$, $R^{15f}$, or $R^{15g}$ is a group represented by Formula W.

In Formula 16, $X^{16a}$ to $X^{16d}$ each independently represent a S atom, an O atom, a Se atom, or $NR^{16g}$, $R^{16a}$ to $R^{16g}$ each independently represent a hydrogen atom or a substituent, and at least one of $R^{16a}$, $R^{16b}$, $R^{16c}$, $R^{16d}$, $R^{16e}$, $R^{16f}$, or $R^{16g}$ is a group represented by Formula W.

—Compound Represented by Formula 1—

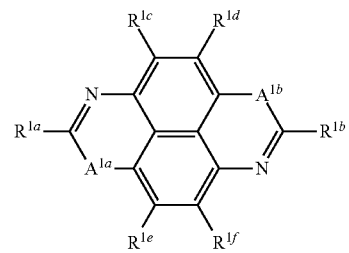

(1)

In Formula 1, $A^{1a}$ and $A^{1b}$ each independently represent a sulfur atom (S atom), an oxygen atom (O atom), or a selenium atom (Se atom). $A^{1a}$ and $A^{1b}$ are preferably a S atom or an O atom. $A^{1a}$ and $A^{1b}$ may be the same as or different from each other, but are preferably the same as each other.

In Formula 1, $R^{1a}$ to $R^{1f}$ each independently represent a hydrogen atom or a substituent. Here, at least one of $R^{1a}$, $R^{1b}$, $R^{1c}$, $R^{1d}$, $R^{1e}$, or $R^{1f}$ is a group represented by Formula W which will be described later.

The compound represented by Formula 1 may have other substituents in addition to the group represented by Formula W which will be described later.

The type of the substituent that $R^{1a}$ to $R^{1f}$ in Formula 1 can adopt is not particularly limited, and examples of the substituent include a substituent X described below. Examples of the substituent X include a group represented by Formula W which will be described later, a halogen atom, an alkyl group (including a cycloalkyl group, a bicycloalkyl group, and a tricycloalkyl group), an alkenyl group (including cycloalkenyl and bicycloalkenyl), an alkynyl group, an aryl group, a heterocyclic group (may be referred to as a hetero ring group), a cyano group, a hydroxy group, a nitro group, a carboxyl group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, alkyl- and aryl sulfonylamino groups, a mercapto group, an alkylthio group, an arylthio group, a heterocyclic thio group, a sulfamoyl group, a sulfo group, alkyl- and aryl sulfinyl groups, alkyl- and aryl sulfonyl groups, an acyl group, an aryloxycarbonyl group, an alkoxycarbonyl group, a carbamoyl group, aryl- and heterocyclic azo groups, an imido group, a phosphino group, a phosphinyl group, a phosphinyloxy group, a phosphinylamino group, a phosphono group, a silyl group, a hydrazino group, a ureido group, a boronic acid group (—B(OH)$_2$), a phosphato group (—OPO(OH)$_2$), a sulfato group (—OSO$_3$H), and other known substituents. In the present specification, examples of the "substituent" in Formulae 1 to 16 preferably include the aforementioned substituent X.

Among these, as the group other than the group represented by Formula W which will be described later, a halogen atom, an alkyl group, an alkynyl group, an alkenyl group, an alkoxy group, an alkylthio group, and an aryl group are preferable, a fluorine atom, a substituted or unsubstituted alkyl group having 1 to 3 carbon atoms, a substituted or unsubstituted alkynyl group having 2 or 3 carbon atoms, a substituted or unsubstituted alkenyl group having 2 or 3 carbon atoms, a substituted or unsubstituted alkoxy group having 1 or 2 carbon atoms, a substituted or unsubstituted methylthio group, and a phenyl group are more preferable, and a fluorine atom, a substituted or unsubstituted alkyl group having 1 to 3 carbon atoms, a substituted or unsubstituted alkynyl group having 2 or 3 carbon atoms, a substituted or unsubstituted alkenyl group having 2 or 3 carbon atoms, a substituted or unsubstituted alkoxy group having 1 or 2 carbon atoms, and a substituted or unsubstituted methylthio group are particularly preferable.

In the compound represented by Formula 1, among $R^{1a}$ to $R^{1f}$, the number of substituents other than the group represented by Formula W is preferably 0 to 4, more preferably 0 to 2, and particularly preferably 0.

Furthermore, these substituents may further have the aforementioned substituents.

Among the substituents, $R^{1c}$ to $R^{1f}$ preferably each independently represent a hydrogen atom, a fluorine atom, a substituted or unsubstituted alkyl group having 1 to 3 carbon atoms, a substituted or unsubstituted alkynyl group having 2 or 3 carbon atoms, a substituted or unsubstituted alkenyl group having 2 or 3 carbon atoms, a substituted or unsubstituted alkoxy group having 1 or 2 carbon atoms, or a substituted or unsubstituted methylthio group.

Next, the group represented by Formula W will be described.

-L$^W$-R$^W$      (W)

In Formula W, L represents a divalent linking group represented by any one of the following Formulae L-1 to L-25 or a divalent linking group in which 2 or more divalent linking groups represented by any one of the following Formulae L-1 to L-25 are bonded to each other.

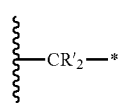
(L-1)

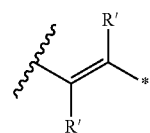
(L-2)

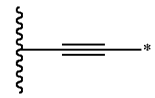
(L-3)

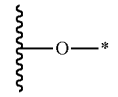
(L-4)

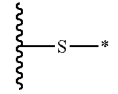
(L-5)

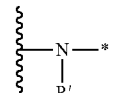
(L-6)

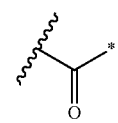
(L-7)

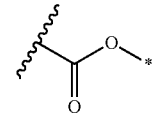
(L-8)

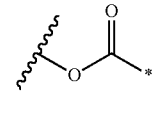
(L-9)

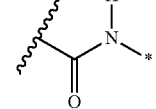
(L-10)

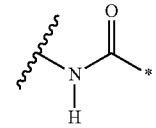
(L-11)

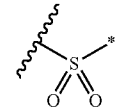
(L-12)

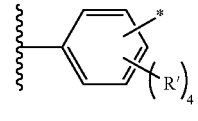
(L-13)

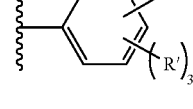
(L-14)

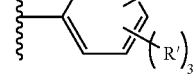
(L-15)

(L-16) 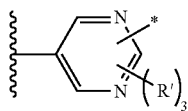

(L-17) 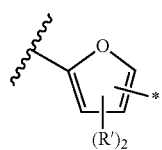

(L-18) 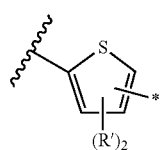

(L-19) 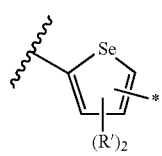

(L-20) 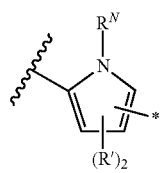

(L-21) 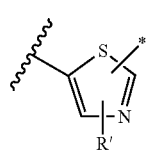

(L-22) 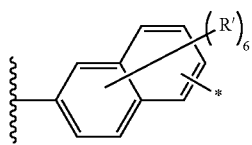

(L-23) 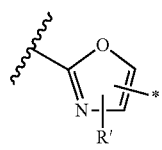

(L-24) 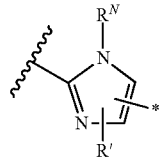

(L-25) 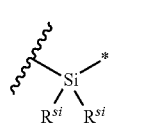

In Formulae L-1 to L-25, * represents a bonding position with respect to $R^W$, and the portion of a wavy line represents a bonding position on the other side. More specifically, for example, in the compound represented by Formula 1, the portion of a wavy line binds to a ring forming the skeleton represented by Formula 1. As will be described later, in a case where Formula W is contained in other compounds, the portion of a wavy line binds to a ring forming the skeleton of each of other compounds.

In a case where $L^W$ represents a divalent linking group in which 2 or more divalent linking groups represented by any one of Formulae L-1 to L-25 are bonded to each other, * of one linking group is bonded to the portion of a wavy line of the other linking group.

In Formulae L-13 to L-24, as the bonding position of R' and the bonding position * with respect to $R^W$, any position on an aromatic ring or a heterocyclic aromatic ring can be adopted.

R' in Formulae L-1, L-2, L-6, and L-13 to L-24 each independently represents a hydrogen atom or a substituent. $R^N$ in Formulae L-20 and L-24 represents a hydrogen atom or a substituent. $R^{si}$ in Formula L-25 each independently represents a hydrogen atom, an alkyl group, an alkenyl group, or an alkynyl group.

R' in Formulae L-1 and L-2 each may form a condensed ring by being bonded to $R^W$ adjacent to $L^W$.

Among the above linking groups, the divalent linking groups represented by any one of Formulae L-17 to L-21, L-23, and L-24 are more preferably divalent linking groups represented by any one of the following Formulae L-17A to L-21A, L-23A, and L-24A.

(L-17A) 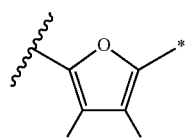

(L-18A) 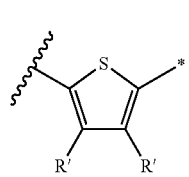

(L-19A) 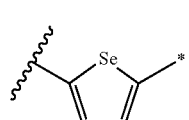

(L-20A) 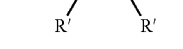

(L-21A) 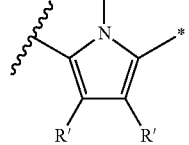

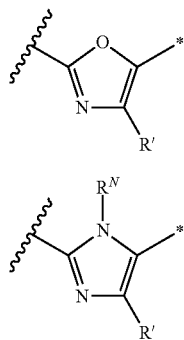

In a case where a substituted or unsubstituted alkyl group, an oxyethylene group, an oligo-oxyethylene group in which a repetition number v of an oxyethylene unit is equal to or greater than 2, a siloxane group, an oligosiloxane group having 2 or more silicon atoms, or a substituted or unsubstituted trialkylsilyl group is present on the terminal of a substituent, the substituent can be interpreted as a substituent consisting only of —$R^W$ in Formula W or a substituent consisting of -L-$R^W$ in Formula W.

In the present invention, in a case where a substituted or unsubstituted alkyl group having a main chain consisting of N carbon atoms is present on the terminal of a substituent, the substituent is interpreted as -L-$R^W$ in Formula W including as many linking groups as possible from the terminal of the substituent. Specifically, the substituent is interpreted as a substituent in which "one group represented by Formula L-1 corresponding to $L^W$ in Formula W" and "a substituted or unsubstituted alkyl group which corresponds to $R^W$ in Formula W and has a main chain consisting of (N−1) carbon atoms" are bonded to each other. For example, in a case where a n-octyl group which is an alkyl group having eight carbon atoms is present on the terminal of a substituent, the substituent is interpreted as a substituent in which one group represented by Formula L-1, in which two R's represent hydrogen atoms, and a n-pentyl group having 7 carbon atoms are bonded to each other.

In contrast, in the present invention, in a case where an oxyethylene group, an oligo-oxyethylene group in which a repetition number v of an oxyethylene unit is equal to or greater than 2, a siloxane group, an oligosiloxane group having 2 or more silicon atoms, or a substituted or unsubstituted trialkylsilyl group is present on the terminal of a substituent, the substituent is interpreted as a substituent consisting only of $R^W$ in Formula W including as many linking groups as possible from the terminal of the substituent. For example, in a case where a —(OCH$_2$CH$_2$)—(OCH$_2$CH$_2$)—(OCH$_2$CH$_2$)—OCH$_3$ group is present on the terminal of a substituent, the substituent is interpreted as a substituent consisting only of an oligo-oxyethylene group in which a repetition number v of an oxyethylene unit is 3.

In a case where $L^W$ forms a linking group in which divalent linking groups represented by any one of Formulae L-1 to L-25 are bonded to each other, the number of bonded divalent linking groups represented by any one of Formulae L-1 to L-25 is preferably 2 to 4, and more preferably 2 or 3.

Examples of the substituent R' in Formulae L-1, L-2, L-6, and L-13 to L-24 include those exemplified above as substituents that the $R^{1a}$ to $R^{1f}$ of Formula 1 can adopt. The substituent R' in Formula L-6 among the above formulae is preferably an alkyl group. In a case where R' in Formula L-6 is an alkyl group, the number of carbon atoms in the alkyl group is preferably 1 to 9, more preferably 4 to 9 from the viewpoint of chemical stability and carrier transport properties, and even more preferably 5 to 9. In a case where R' in Formula L-6 is an alkyl group, the alkyl group is preferably a linear alkyl group, because then the mobility can be improved.

$R^N$ in Formulae L-20 and L-24 represents a hydrogen atom or a substituent. Examples of $R^N$ include those exemplified above as substituents that $R^{1a}$ to $R^{1f}$ in Formula 1 can adopt. $R^N$ is preferably a hydrogen atom or a methyl group among the substituents.

$R^{si}$ in Formula L-25 each independently represents a hydrogen atom, an alkyl group, an alkenyl group, or an alkynyl group. $R^{si}$ is preferably an alkyl group. The alkyl group that $R^{si}$ can adopt is not particularly limited. A preferred range of the alkyl group that that $R^{si}$ can adopt is the same as a preferred range of an alkyl group that a trialkylsilyl group can adopt in a case where R represents the trialkylsilyl group. The alkenyl group that $R^{si}$ can adopt is not particularly limited. The alkenyl group is preferably a substituted or unsubstituted alkenyl group and more preferably a branched alkenyl group, and the alkenyl group preferably has 2 or 3 carbon atoms. The alkynyl group that $R^{si}$ can adopt is not particularly limited. The alkynyl group is preferably a substituted or unsubstituted alkynyl group and more preferably a branched alkynyl group, and the alkynyl group preferably has 2 or 3 carbon atoms.

$L^W$ is preferably a divalent linking group which is represented by any one of Formulae L-1 to L-5, L-13, L-17, and L-18 or a divalent linking group in which 2 or more divalent linking groups represented by any one of Formulae L-1 to L-5, L-13, L-17, and L-18 are bonded to each other, more preferably a divalent linking group which is represented by any one of Formulae L-1, L-3, L-13, and L-18 or a divalent linking group in which 2 or more divalent linking groups represented by any one of Formulae L-1, L-3, L-13, and L-18 are bonded to each other, and particularly preferably a divalent linking group which is represented by any one of Formulae L-1, L-3, L-13, and L-18 or a divalent linking group in which a divalent linking group represented by any one of Formulae L-3, L-13, and L-18 is bonded to a divalent linking group represented by Formula L-1.

It is preferable that, in the divalent linking group, in which a divalent linking group represented by any one of Formulae L-3, L-13, and L-18 and a divalent linking group represented by Formula L-1 are bonded to each other, the divalent linking group represented by Formula L-1 is bonded to the $R^W$ side.

From the viewpoint of chemical stability and carrier transport properties, $L^W$ is particularly preferably a divalent linking group containing a divalent linking group represented by Formula L-1, and more particularly preferably a divalent linking group represented by Formula L-1. It is most preferable that $L^W$ is a divalent linking group represented by Formula L-1 and $R^W$ is a substituted or unsubstituted alkyl group.

In Formula W, $R^W$ represents a substituted or unsubstituted alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having 2 or more silicon atoms, or a substituted or unsubstituted trialkylsilyl group.

In Formula W, in a case where $L^W$ adjacent to $R^W$ is a divalent linking group which is represented by Formula L-1, $R^W$ is preferably a substituted or unsubstituted alkyl group, an oxyethylene group, an oligo-oxyethylene group in which a repetition number v of an oxyethylene unit is equal to or greater than 2, a siloxane group, or an oligosiloxane group having 2 or more silicon atoms, and more preferably a substituted or unsubstituted alkyl group.

In Formula W, in a case where $L^W$ adjacent to $R^W$ is a divalent linking group which is represented by any one of Formula L-2 and Formulae L-4 to L-25, $R^W$ is more preferably a substituted or unsubstituted alkyl group.

In Formula W, in a case where $L^W$ adjacent to $R^W$ is a divalent linking group which is represented by Formula L-3, $R^W$ is preferably a substituted or unsubstituted alkyl group or a substituted or unsubstituted trialkylsilyl group.

In a case where $R^W$ is a substituted or unsubstituted alkyl group, the number of carbon atoms in the alkyl group is preferably 4 to 17, more preferably 6 to 14 from the viewpoint of chemical stability and carrier transport properties, and even more preferably 6 to 12. It is preferable that R is a long-chain alkyl group having carbon atoms within the above range, particularly, a long-chain linear alkyl group, because then the linearity of the molecule is improved, and hence the mobility can be improved.

In a case where $R^W$ represents an alkyl group, the alkyl group may be linear, branched, or cyclic. It is preferable that the alkyl group is a linear alkyl group, because then the linearity of the molecule is improved, and hence the mobility can be improved.

Particularly, from the viewpoint of improving the mobility, $R^W$ and $L^W$ in Formula W preferably form a combination in which $L^W$ in Formula 1 is a divalent linking group represented by Formula L-1 and $R^W$ in Formula 1 is a linear alkyl group having 7 to 17 carbon atoms or a combination in which $L^W$ is a divalent linking group, in which a divalent linking group represented by any one of Formulae L-3, L-13, and L-18 and a divalent linking group represented by Formula L-1 are bonded to each other, and $R^W$ is a linear alkyl group.

In a case where $L^W$ is a divalent linking group represented by Formula L-1 and $R^W$ is a linear alkyl group having 7 to 17 carbon atoms, $R^W$ is more preferably a linear alkyl group having 7 to 14 carbon atoms from the viewpoint of improving the mobility, and particularly preferably a linear alkyl group having 7 to 12 carbon atoms.

In a case where $L^W$ is a divalent linking group, in which a divalent linking group represented by any one of Formulae L-3, L-13, and L-18 and a divalent linking group represented by Formula L-1 are bonded to each other, and $R^W$ is a linear alkyl group, $R^W$ is more preferably a linear alkyl group having 4 to 17 carbon atoms, even more preferably a linear alkyl group having 6 to 14 carbon atoms from the viewpoint of chemical stability and carrier transport properties, and particularly preferably a linear alkyl group having 6 to 12 carbon atoms from the viewpoint of improving the mobility.

In contrast, from the viewpoint of improving the solubility in an organic solvent, $R^W$ is preferably a branched alkyl group.

In a case where $R^W$ is an alkyl group having a substituent, examples of the substituent include a halogen atom and the like, and the halogen atom is preferably a fluorine atom. In a case where $R^W$ is an alkyl group having a fluorine atom, all of the hydrogen atoms of the alkyl group may be substituted with fluorine atoms such that a perfluoroalkyl group is formed. Here, $R^W$ is preferably an unsubstituted alkyl group.

In the present specification, in a case where $R^W$ is an oligo-oxyethylene group in which the repetition number v of an oxyethylene unit is equal to or greater than 2, the "oligo-oxyethylene group" represented by R refers to a group represented by $-(OCH_2CH_2)_v-OY$ (the repetition number v of an oxyethylene unit represents an integer of equal to or greater than 2, and Y on the terminal represents a hydrogen atom or a substituent). In a case where Y on the terminal of the oligo-oxyethylene group is a hydrogen atom, the terminal becomes a hydroxyl group. The repetition number v of the oxyethylene unit is preferably 2 to 4, and more preferably 2 or 3.

It is preferable that the hydroxyl group on the terminal of the oligo-oxyethylene group is capped. That is, it is preferable that Y represents a substituent. In this case, the hydroxyl group is preferably capped with an alkyl group having 1 to 3 carbon atoms. That is, Y is preferably an alkyl group having 1 to 3 carbon atoms, more preferably a methyl group or an ethyl group, and particularly preferably a methyl group.

In a case where $R^W$ is a siloxane group or an oligosiloxane group having 2 or more silicon atoms, a repetition number of the siloxane unit is preferably 2 to 4, and more preferably 2 or 3. Furthermore, it is preferable that a hydrogen atom or an alkyl group is bonded to each silicon atom (Si atom). In a case where an alkyl group is bonded to the silicon atom, the number of carbon atoms in the alkyl group is preferably 1 to 3. For example, it is preferable that a methyl group or an ethyl group is bonded to the silicon atom. The same alkyl groups may be bonded to the silicon atoms, or different alkyl groups or hydrogen atoms may be bonded to the silicon atoms. All of the siloxane units constituting the oligosiloxane group may be the same as or different from each other, but it is preferable that all of the siloxane units are the same as each other.

In a case where $L^W$ adjacent to $R^W$ is a divalent linking group represented by Formula L-3, $R^W$ is preferably a substituted or unsubstituted trialkylsilyl group. In a case where $R^W$ is a substituted or unsubstituted trialkylsilyl group, the substituent of the silyl group is not particularly limited as long as the substituent is a substituted or unsubstituted alkyl group. However, it is preferable that the substituent is a branched alkyl group. The number of carbon atoms in the alkyl group bonded to each silicon atom is preferably 1 to 3. For example, it is preferable that a methyl group, an ethyl group, or an isopropyl group is bonded to the silicone atoms. The same alkyl groups or different alkyl groups may be bonded to the silicon atoms. In a case where $R^W$ is a trialkylsilyl group further having a substituent on an alkyl group, the substituent is not particularly limited.

In Formula W, the total number of carbon atoms contained in $L^W$ and $R^W$ is preferably 5 to 18. In a case where the total number of carbon atoms contained in $L^W$ and $R^W$ is equal to or greater than the lower limit of the above range, the mobility is improved, and the driving voltage is reduced. In a case where the total number of carbon atoms contained in $L^W$ and $R^W$ is equal to or less than the upper limit of the above range, the solubility in an organic solvent is improved.

The total number of carbon atoms contained in $L^W$ and $R^W$ is preferably 5 to 14, more preferably 6 to 14, even more preferably 6 to 12, and particularly preferably 8 to 12.

In the compound represented by Formula 1, the number of groups represented by Formula W among $R^{1a}$ to $R^{1f}$ is preferably 1 to 4, more preferably 1 or 2, and particularly preferably 2.

In the present invention, at least one of $R^{1a}$ or Rlb in Formula 1 is preferably a group represented by Formula W for the following reason. That is, it is considered that from the viewpoint of excellent chemical stability of the compound, the highest occupied molecular orbital (HOMO) level, and packing in a film of molecules, the positions of $R^{1a}$ and $R^{1b}$ are suitable as substitution positions in Formula 1. Particularly, in Formula 1, in a case where a substituent is on the 2 sites of $R^{1a}$ and $R^{1b}$, high carrier density can be obtained.

In Formula 1, $R^{1c}$ to $R^{1f}$ preferably each independently represent a hydrogen atom, a fluorine atom, a substituted or unsubstituted alkyl group having 1 to 3 carbon atoms, a substituted or unsubstituted alkynyl group having 2 or 3 carbon atoms, a substituted or unsubstituted alkenyl group having 2 or 3 carbon atoms, a substituted or unsubstituted alkoxy group having 1 or 2 carbon atoms, or a substituted or unsubstituted methylthio group.

In the present invention, from the viewpoint of the mobility of the organic semiconductor film, the compound represented by Formula 1 is preferably a compound represented by Formula 1A.

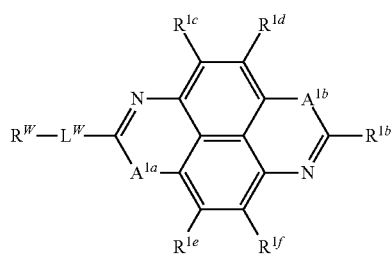

(1A)

The definition of each of $A^{1a}$, $A^{1b}$, and $R^{1b}$ to $R^{1f}$ in Formula 1A is the same as the definition of each of Ala, $A^{1b}$, and $R^{1b}$ to $R^{1f}$ in Formula 1 described above. Furthermore, the definition of each of $L^W$ and $R^W$ in Formula 1A is the same as the definition of each of $L^W$ and $R^W$ in Formula W described above.

From the viewpoint of the mobility of the organic semiconductor film, the compound represented by Formula 1 is preferably a compound represented by Formula 1B.

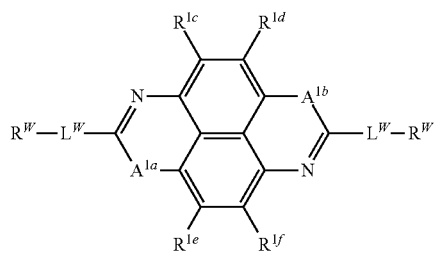

(1B)

The definition of each of $A^{1a}$, $A^{1b}$, and $R^{1c}$ to $R^{1f}$ in Formula 1B is the same as the definition of each of $A^{1a}$, $A^{1b}$, and $R^{1c}$ to $R^{1f}$ in Formula 1 described above. Furthermore, the definition of each of $L^W$ and $R^W$ in Formula 1B is the same as the definition of each of $L^W$ and $R^W$ in Formula W described above. In Formula 1B, two $L^W$'s and two $R^W$'s may be the same as or different from each other.

From the viewpoint of the mobility of the organic semiconductor film, the compound represented by Formula 1 is preferably a compound represented by Formula 1C.

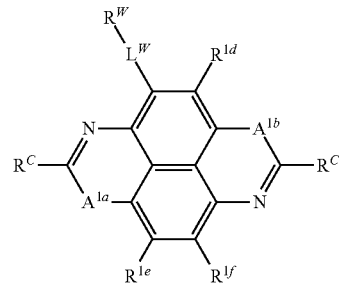

(1C)

The definition of each of Ala, $A^{1b}$, and $R^{1d}$ to $R^{1f}$ in Formula 1C is the same as the definition of each of Ala, $A^{1b}$, and $R^{1d}$ to $R^{1f}$ in Formula 1 described above. Furthermore, the definition of each of $L^W$ and $R^W$ in Formula 1C is the same as the definition of each of $L^W$ and $R^W$ in Formula W described above. $R^c$ each independently represents a hydrogen atom or an aryl group.

From the viewpoint of the mobility of the organic semiconductor film, the compound represented by Formula 1 is preferably a compound represented by Formula 1D.

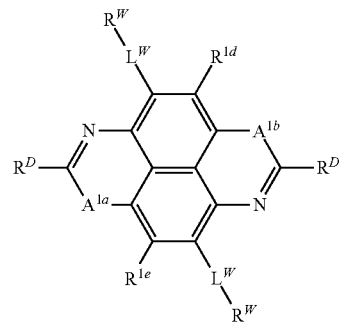

(1D)

The definition of each of $A^{1a}$, $A^{1b}$, $R^{1d}$, and $R^{1e}$ in Formula 1D is the same as the definition of each of $A^{1a}$, $A^{1b}$, $R^{1d}$, and $R^{1e}$ in Formula 1 described above. Furthermore, the definition of each of $L^W$ and $R^W$ in Formula 1D is the same as the definition of each of $L^W$ and $R^W$ in Formula W described above. In Formula 1D, two $L^W$'s and two $R^W$'s may be the same as or different from each other. $R^D$ each independently represents a hydrogen atom or an aryl group.

—Compound Represented by Formula 2—

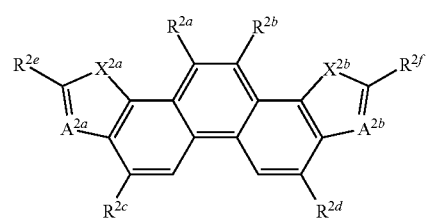

(2)

In Formula 2, $X^{2a}$ and $X^{2b}$ each independently represent $NR^{2i}$ (>N—$R^{2i}$), an O atom, or a S atom. From the viewpoint of ease of synthesis, $X^{2a}$ and $X^{2b}$ preferably each independently represent an O atom or a S atom. In contrast, from the viewpoint of improving the mobility, at least one of $X^{2a}$ or $X^{2b}$ preferably represents a S atom.

$X^{2a}$ and $X^{2b}$ are preferably the same linking groups. It is more preferable that both of $X^{2a}$ and $X^{2b}$ are S atoms.

$R^{2i}$ represents a hydrogen atom, an alkyl group, an alkenyl group, an alkynyl group, or an acyl group. $R^{2i}$ is preferably a hydrogen atom or an alkyl group, more preferably an alkyl group having 1 to 14 carbon atoms, and particularly preferably an alkyl group having 1 to 4 carbon atoms.

In a case where $R^{2i}$ represents an alkyl group, the alkyl group may be linear, branched, or cyclic. It is preferable that the alkyl group is a linear alkyl group, because then the linearity of the molecule is improved, and hence the mobility can be improved.

In Formula 2, $A^{2a}$ represents $CR^{2g}$ or a N atom, $A^{2b}$ represents $CR^{2h}$ or a N atom, and $R^{2g}$ and $R^{2h}$ each independently represent a hydrogen atom or a substituent. It is preferable that $A^{2a}$ represents $CR^{2g}$, or $A^{2b}$ represents $CR^{2h}$. It is more preferable that $A^{2a}$ represents $CR^{2g}$, and $A^{2b}$ represents $CR^{2h}$. $A^{2a}$ and $A^{2b}$ may be the same as or different from each other, but it is preferable that they are the same as each other.

In Formula 2, $R^{2e}$ and $R^{2g}$ may or may not form a ring by being bonded to each other, but it is preferable that they do not form a ring by being bonded to each other.

In Formula 2, $R^{2f}$ and $R^{2h}$ may or may not form a ring by being bonded to each other, but it is preferable that they do not form a ring by being bonded to each other.

In Formula 2, $R^{2a}$ to $R^{2h}$ each independently represent a hydrogen atom or a substituent, and at least one of $R^{2a}$, $R^{2b}$, $R^{2c}$, $R^{2d}$, $R^{2e}$, $R^{2f}$, $R^{2g}$, or $R^{2h}$ represents a substituent represented by Formula W.

Examples of the substituent that $R^{2a}$ to $R^{2h}$ can each independently adopt include the substituent X described above. The definition of the substituent represented by Formula W is as described above.

The substituent that $R^{2a}$ to $R^{2h}$ can each independently adopt is preferably an alkyl group, an aryl group, an alkenyl group, an alkynyl group, a heterocyclic group, an alkoxy group, an alkylthio group, or a substituent represented by Formula W, more preferably an alkyl group having 1 to 12 carbon atoms, an aryl group having 6 to 20 carbon atoms, an alkenyl group having 2 to 12 carbon atoms, an alkynyl group having 2 to 12 carbon atoms, an alkoxy group having 1 to 11 carbon atoms, a heterocyclic group having 5 to 12 carbon atoms, an alkylthio group having 1 to 12 carbon atoms, or a group represented by Formula W, particularly preferably a group having a chain length of a linking group, which will be described later, of equal to or less than 3.7 Å (=0.37 nm) or a group represented by Formula W, and more particularly preferably a group represented by Formula W.

In the compound represented by Formula 2, among $R^{2a}$ to $R^{2h}$, the number of groups represented by Formula W is preferably 1 to 4 from the viewpoint of improving the mobility and improving the solubility in an organic solvent, more preferably 1 or 2, and particularly preferably 2.

A group represented by Formula W can be positioned in any of $R^{2a}$ to $R^{2h}$ without particular limitation. From the viewpoint of improving the mobility and improving the solubility in an organic solvent, the group represented by Formula W is preferably positioned in $R^{2e}$ or $R^{2f}$.

Among $R^{2a}$ to $R^{2h}$, the number of substituents other than a group represented by Formula W is preferably 0 to 4, more preferably 0 to 2, even more preferably 0 or 1, and particularly preferably 0.

In a case where $R^{2a}$ to $R^{2h}$ each represent a substituent other than a group represented by W, the substituent is preferably a group having a chain length of a linking group of equal to or less than 3.7 Å, more preferably a group having a chain length of a linking group of 1.0 to 3.7 Å, and even more preferably a group having a chain length of a linking group of 1.0 to 2.1 Å.

The chain length of a linking group refers to a length from a C atom to the terminal of a substituent R in a C (carbon atom)-R bond. The calculation for structural optimization can be performed using a density functional method (Gaussian 03 (Gaussian, Inc)/basis function: 6-31G', exchange-correlation functional: B3LYP/LANL2DZ). Regarding a molecular length of typical substituents, a propyl group has a molecular length of 4.6 Å, a pyrrole group has a molecular length of 4.6 Å, a propynyl group has a molecular length of 4.5 Å, a propenyl group has a molecular length of 4.6 Å, an ethoxy group has a molecular length of 4.5 Å, a methylthio group has a molecular length of 3.7 Å, an ethenyl group has a molecular length of 3.4 Å, an ethyl group has a molecular length of 3.5 Å, an ethynyl group has a molecular length of 3.6 Å, a methoxy group has a molecular length of 3.3 Å, a methyl group has a molecular length of 2.1 Å, and a hydrogen atom has a molecular length of 1.0 Å.

In a case where $R^{2a}$ to $R^{2h}$ represent substituents other than a group represented by Formula W, the substituents preferably each independently represent a substituted or unsubstituted alkyl group having 2 or less carbon atoms, a substituted or unsubstituted alkynyl group having 2 or less carbon atoms, a substituted or unsubstituted alkenyl group having 2 or less carbon atoms, or a substituted or unsubstituted acyl group having 2 or less carbon atoms, and more preferably each independently represent a substituted or unsubstituted alkyl group having 2 or less carbon atoms.

In a case where $R^{2a}$ to $R^{2h}$ represent substituents other than a group represented by Formula W, and the substituents each independently represent a substituted alkyl group having 2 or less carbon atoms, examples of substituents that the alkyl group can have include a cyano group, a fluorine atom, a deuterium atom, and the like. Among these, a cyano group is preferable. In a case where $R^{2a}$ to $R^{2h}$ represent substituents other than a group represented by Formula W, the substituted or unsubstituted alkyl group having 2 or less carbon atoms that is represented by each of the substituents is preferably a methyl group, an ethyl group, or a methyl group substituted with a cyano group, more preferably a methyl group or a methyl group substituted with a cyano group, and particularly preferably a methyl group substituted with a cyano group.

In a case where $R^{2a}$ to $R^{2h}$ represent substituents other than a group represented by Formula W, and the substituents each independently represent a substituted alkynyl group having 2 or less carbon atoms, examples of substituents that the alkynyl group can have include a deuterium atom and the like. In a case where $R^{2a}$ to $R^{2h}$ represent substituents other than a group represented by Formula W, examples of the substituted or unsubstituted alkynyl group having 2 or less carbon atoms that is represented by each of the substituents include an ethynyl group and an acetylene group substituted with a deuterium atom. Between these, an ethynyl group is preferable.

In a case where $R^{2a}$ to $R^{2h}$ represent substituents other than a group represented by Formula W, and the substituents each independently represent a substituted alkenyl group having 2 or less carbon atoms, examples of substituents that the alkenyl group can have include a deuterium atom and the like. In a case where $R^{2a}$ to $R^{2h}$ represent substituents other than a group represented by Formula W, examples of the substituted or unsubstituted alkenyl group having 2 or less carbon atoms that is represented by each of the substituents include an ethenyl group and an ethenyl group substituted with a deuterium atom. Between these, an ethenyl group is preferable.

In a case where $R^{2a}$ to $R^{2h}$ represent substituents other than a group represented by Formula W, and the substituents each independently represent a substituted acyl group having 2 or less carbon atoms, examples of substituents that the acyl group can have include a fluorine atom and the like. In a case where $R^{2a}$ to $R^{2h}$ represent substituents other than a group represented by Formula W, examples of the substituted or unsubstituted acyl group having 2 or less carbon atoms that is represented by each of the substituents include a formyl group, an acetyl group, and an acetyl group substituted with fluorine. Among these, a formyl group is preferable.

The compound represented by Formula 2 is preferably a compound represented by the following Formula 2A or 2B, and particularly preferably a compound represented by Formula 2A from the viewpoint of high mobility.

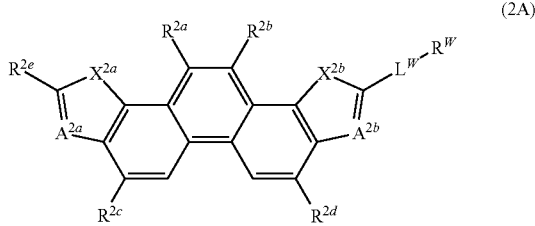

(2A)

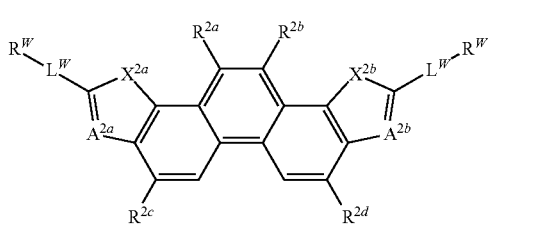

(2B)

In Formula 2A, $X^{2a}$ and $X^{2b}$ each independently represent an O atom or a S atom, $A^{2a}$ represents $CR^{2g}$ or a N atom, $A^{2b}$ represents $CR^{2h}$ or a N atom, $R^{2a}$ to $R^{2e}$, $R^{2g}$, and $R^{2h}$ each independently represent a hydrogen atom or a substituent. The definition of each of $L^W$ and $R^W$ in Formula 2A is the same as the definition of each of $L^W$ and $R^W$ in Formula W described above.

In Formula 2B, $X^{2a}$ and $X^{2b}$ each independently represent an O atom or a S atom, $A^{2a}$ represents $CR^{2g}$ or a N atom, $A^{2b}$ represents $CR^{2h}$ or a N atom, $R^{2a}$ to $R^{2d}$, $R^{2g}$, and $R^{2h}$ each independently represent a hydrogen atom or a substituent. The definition of each of $L^W$ and $R^W$ in Formula 2B is the same as the definition of each of $L^W$ and $R^W$ in Formula W described above. Furthermore, in Formula 2B, two $L^W$'s and two $R^W$'s may be the same as or different from each other.

—Compound Represented by Formula 3—

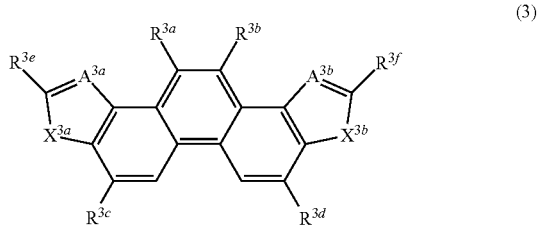

(3)

In Formula 3, $R^{3a}$ to $R^{3f}$ and $R^{3g}$ and $R^{3h}$, which will be described later, each independently represent a hydrogen atom or a substituent. Here, at least one of $R^{3a}$, $R^{3b}$, $R^{3c}$, $R^{3d}$, $R^{3e}$, $R^{3f}$, $R^{3g}$, or $R^{3h}$ represents a group represented by Formula W.

Examples of the substituent represented by $R^{3a}$ to $R^{3b}$ include the substituent X described above. The definition of a group represented by Formula W is as described above.

The substituent that $R^{3a}$ to $R^{3f}$ can each independently adopt is preferably an alkyl group, an aryl group, an alkenyl group, an alkynyl group, a heterocyclic group, an alkoxy group, an alkylthio group, or a substituent represented by Formula W, and more preferably an alkyl group having 1 to 12 carbon atoms, an aryl group having 6 to 20 carbon atoms, an alkenyl group having 2 to 12 carbon atoms, an alkynyl group having 2 to 12 carbon atoms, an alkoxy group having 1 to 11 carbon atoms, a heterocyclic group having 5 to 12 carbon atoms, an alkylthio group having 1 to 12 carbon atoms, or a group represented by Formula W.

In Formula 3, $X^{3a}$ and $X^{3b}$ each independently represent a S atom, an O atom, or $NR^{3g}$ (>N—$R^{3g}$), and $R^{3g}$ represents a hydrogen atom or a substituent. X is preferably a S atom or an O atom. In Formula 3, $X^{3a}$ and $X^{3b}$ are preferably the same as each other.

$R^{3g}$ is preferably a hydrogen atom, an alkyl group, or an aryl group, more preferably an alkyl group having 1 to 14 carbon atoms, and particularly preferably an alkyl group having 4 to 12 carbon atoms. It is preferable that $R^{3g}$ is a long-chain alkyl group having carbon atoms within the above range, particularly, a long-chain linear alkyl group, because then the linearity of the molecule is improved, and hence the mobility can be improved.

In a case where $R^{3g}$ is an alkyl group, the alkyl group may be linear, branched, or cyclic. It is preferable that the alkyl group is a linear alkyl group, because then the linearity of the molecule is improved, and hence the mobility can be improved.

In Formula 3, $A^{3a}$ and $A^{3b}$ each independently represent $CR^{3h}$ or a N atom. It is preferable that $A^{3a}$ and $A^{3b}$ each independently represent $CR^{3h}$. In Formula 3, $A^{3a}$ and $A^{3b}$ may be the same as or different from each other, but it is preferable that they are the same as each other.

$R^{3h}$ is preferably a group having a chain length of a linking group of equal to or less than 3.7 Å, more preferably a group having a chain length of a linking group of 1.0 to 3.7 Å, and even more preferably a group having a chain length of a linking group of 1.0 to 2.1 Å. The definition of a chain length of a linking group is as described above.

$R^{3h}$ is preferably a hydrogen atom, a substituted or unsubstituted alkyl group having 2 or less carbon atoms, a substituted or unsubstituted alkynyl group having 2 or less carbon atoms, a substituted or unsubstituted alkenyl group having 2 or less carbon atoms, or a substituted or unsubstituted acyl group having 2 or less carbon atoms, more preferably a hydrogen atom or a substituted or unsubstituted alkyl group having 2 or less carbon atoms, and particularly preferably a hydrogen atom.

In a case where $R^{3h}$ represents a substituted alkyl group having 2 or less carbon atoms, examples of substituents that the alkyl group can have include a cyano group, a fluorine atom, a deuterium atom, and the like. Among these, a cyano group is preferable. The substituted or unsubstituted alkyl group having 2 or less carbon atoms that is represented by $R^{3h}$ is preferably a methyl group, an ethyl group, or a methyl group substituted with a cyano group, more preferably a methyl group or a methyl group substituted with a cyano group, and particularly preferably a methyl group substituted with a cyano group.

In a case where $R^{3h}$ represents a substituted alkynyl group having 2 or less carbon atoms, examples of substituents that the alkynyl group can have include a deuterium atom and the like. Examples of the substituted or unsubstituted alkynyl group having 2 or less carbon atoms that is represented by $R^{3h}$ include an ethynyl group and an acetylene group substituted with a deuterium atom. Between these, an ethynyl group is preferable.

In a case where $R^{3h}$ represents a substituted alkenyl group having 2 or less carbon atoms, examples of substituents that the alkenyl group can have include a deuterium atom and the like. Examples of the substituted or unsubstituted alkenyl group having 2 or less carbon atoms that is represented by $R^{3h}$ include an ethenyl group and an ethenyl group substituted with a deuterium atom. Between these, an ethenyl group is preferable.

In a case where $R^{3h}$ represents a substituted acyl group having 2 or less carbon atoms, examples of substituents that the acyl group can have include a fluorine atom and the like. Examples of the substituted or unsubstituted acyl group having 2 or less carbon atoms that is represented by $R^{3h}$ include a formyl group, an acetyl group, and an acetyl group substituted with a fluorine atom. Among these, a formyl group is preferable.

The compound represented by Formula 3 is preferably a compound represented by Formula 3A, 3B, or 3C, more preferably a compound represented by Formula 3A or 3B, and particularly preferably a compound represented by Formula 3A from the viewpoint of high solubility. In contrast, from the viewpoint of high mobility, the compound represented by Formula 3 is particularly preferably a compound represented by Formula 3B.

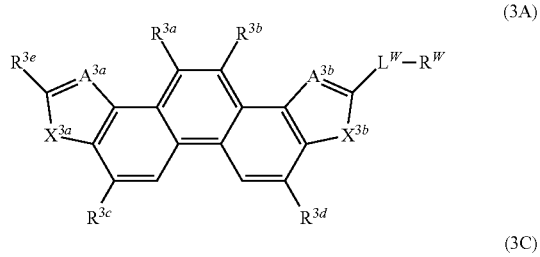

(3A)

(3C)

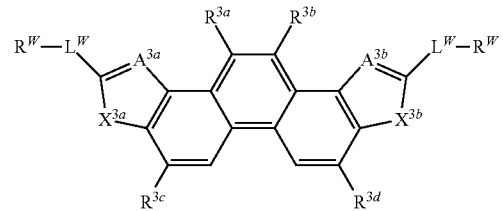

(3B)

In Formula 3A, $X^{3a}$ and $X^{3b}$ each independently represent a S atom, an O atom, or $NR^{3g}$, and $A^{3a}$ and $A^{3b}$ each independently represent $CR^{3h}$ or a N atom. $R^{3a}$ to $R^{3e}$, $R^{3g}$, and $R^{3h}$ each independently represent a hydrogen atom or a substituent. Here, $R^{3e}$ is not a group represented by Formula W. The definition of each of $L^W$ and $R^W$ in Formula 3A is the same as the definition of each of $L^W$ and $R^W$ in Formula W described above.

In Formula 3B, $X^{3a}$ and $X^{3b}$ each independently represent a S atom, an O atom, or $NR^{3g}$, and $A^{3a}$ and $A^{3b}$ each independently represent $CR^{3h}$ or a N atom. $R^{3a}$ to $R^{3d}$, $R^{3g}$, and $R^{3h}$ each independently represent a hydrogen atom or a substituent. The definition of each of $L^W$ and $R^W$ in Formula 3B is the same as the definition of each of $L^W$ and $R^W$ in Formula W described above. Furthermore, in Formula 3B, two $L^W$'s and two $R^W$'s may be the same as or different from each other.

In Formula 3C, $A^{3a}$ and $A^{3b}$ each independently represent $CR^{3h}$ or a N atom. $R^{3a}$ to $R^{3f}$ and $R^{3h}$ each independently represent a hydrogen atom or a substituent. The definition of each of $L^W$ and $R^W$ in Formula 3C is the same as the definition of each of $L^W$ and $R^W$ in Formula W described above. Furthermore, in Formula 3C, two $L^W$'s and two $R^W$'s may be the same as or different from each other.

—Compound Represented by Formula 4—

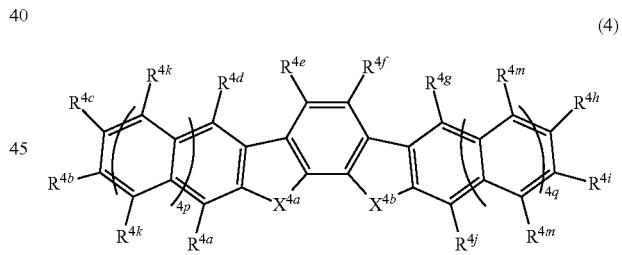

(4)

In Formula 4, $X^{4a}$ and $X^{4b}$ each independently represent an O atom, a S atom, or a Se atom.

It is preferable that $X^{4a}$ and $X^{4b}$ each independently represent an O atom or a S atom. From the viewpoint of improving the mobility, it is more preferable that at least one of $X^a$ or $X^{4b}$ is a S atom. It is preferable that $X^{4a}$ and $X^{4b}$ are the same linking groups. It is particularly preferable that both of $X^{4a}$ and $X^{4b}$ are S atoms.

In Formula 4, 4p and 4q each independently represent an integer of 0 to 2. It is preferable that 4p and 4q each independently represent 0 or 1, because then the mobility and the solubility can be achieved at the same time. It is more preferable that 4p=4q=0 or 4p=4q=1.

In Formula 4, $R^{4a}$ to $R^{4k}$ and $R^{4m}$ each independently represent a hydrogen atom, a halogen atom, or a group represented by Formula W, and at least one of $R^{4a}$, $R^{4b}$, $R^{4c}$, $R^{4d}$, $R^{4e}$, $R^{4f}$, $R^{4g}$, $R^{4h}$, $R^{4i}$, $R^{4j}$, $R^{4k}$, or $R^{4m}$ is a group represented by Formula W. Here, in a case where at least one of $R^{4e}$ or $R^{4f}$ is a group represented by Formula W, in Formula W represented by $R^{4e}$ and $R^{4f}$, $L^W$ is a divalent linking group represented by Formula L-2 or L-3. The definition of a group represented by Formula W is as described above.

The case where at least one of $R^{4e}$ or $R^{4f}$ is a group represented by Formula W corresponds to a case where none of $R^{4e}$ and $R^{4f}$ are a hydrogen atom or a halogen atom.

In a case where at least one of $R^{4e}$ or $R^{4f}$ is a group represented by Formula W, in Formula W represented by $R^{4e}$ and $R^{4f}$, $L^W$ is preferably a divalent linking group represented by Formula L-3.

In a case where at least one of $R^{4e}$ or $R^{4f}$ is a group represented by Formula W, both of $R^{4e}$ and $R^{4f}$ preferably represent a group represented by Formula W.

In a case where both of $R^{4e}$ and $R^{4f}$ represent a hydrogen atom or a halogen atom, $R^{4a}$ to $R^{4d}$, $R^{4g}$ to $R^{4k}$, and $R^{4m}$ each independently represent a hydrogen atom, a halogen atom, or a group represented by Formula W, and at least one or more out of $R^{4a}$, $R^{4b}$, $R^{4c}$, $R^{4d}$, $R^{4g}$, $R^{4h}$, $R^{4i}$, $R^{4j}$, $R^{4k}$, or $R^{4m}$ is a group represented by Formula W.

Examples of the halogen atom represented by $R^{4a}$ to $R^{4k}$ and $R^{4m}$ in Formula 4 include a fluorine atom, a chlorine atom, a bromine atom, and an iodine atom. The halogen atom is preferably a fluorine atom, a chlorine atom, or a bromine atom, more preferably a fluorine atom or a chlorine atom, and particularly preferably a fluorine atom.

Among $R^{4a}$ to $R^{4k}$ and $R^{4m}$ in the compound represented by Formula 4, the number of halogen atoms is preferably 0 to 4, more preferably 0 to 2, even more preferably 0 or 1, and particularly preferably 0.

In the compound represented by Formula 4, among $R^{4a}$ to $R^{4k}$ and $R^{4m}$, the number of groups represented by Formula W is preferably 1 to 4 from the viewpoint of improving the mobility and improving the solubility in an organic solvent, more preferably 1 or 2, and particularly preferably 2.

A group represented by Formula W can be positioned in any of $R^{4a}$ to $R^{4k}$ and $R^{4m}$ without particular limitation. In the present invention, from the viewpoint of improving the mobility and improving the solubility in an organic solvent, it is preferable that, in Formula 4, $R^{4a}$, $R^{4d}$ to $R^{4g}$, $R^{4j}$, $R^{4k}$, and $R^{4m}$ each independently represent a hydrogen atom or a halogen atom, $R^{4b}$, $R^{4c}$, $R^{4h}$, and $R^{4i}$ each independently represent a hydrogen atom, a halogen atom, or a group represented by Formula W, and at least one of $R^{4b}$, $R^{4c}$, $R^{4h}$, or $R^{4i}$ is a group represented by Formula W.

In the present invention, it is more preferable that $R^{4a}$, $R^{4c}$ to $R^{4h}$, and $R^{4j}$ each independently represent a hydrogen atom or a halogen atom, $R^{4b}$ and $R^{4i}$ each independently represent a hydrogen atom, a halogen atom, or a group represented by Formula W, and at least one of $R^{4b}$ or $R^{4i}$ is a group represented by Formula W.

In the present invention, it is even more preferable that both of $R^{4b}$ and $R^{4i}$ represent a group represented by Formula W, both of $R^{4c}$ and $R^{4h}$ represent a hydrogen atom or a halogen atom, or both of $R^{4c}$ and $R^{4h}$ represent a group represented by Formula W, and both of $R^{4b}$ and $R^{4i}$ represent a hydrogen atom or a halogen atom.

In the present invention, it is particularly preferable that both of $R^{4b}$ and $R^{4i}$ represent a group represented by Formula W and both of $R^{4c}$ and $R^{4h}$ represent a hydrogen atom or a halogen atom, or both of $R^{4c}$ and $R^{4h}$ represent a group represented by Formula W and both of $R^{4b}$ and $R^{4i}$ represent a hydrogen atom or a halogen atom.

In Formula 4, 2 or more groups among $R^{4a}$ to $R^{4k}$ and $R^{4m}$ may or may not form a ring by being bonded to each other, but it is preferable that they do not form a ring by being bonded to each other.

The compound represented by Formula 4 is preferably a compound represented by the following Formula 4A or 4B, and particularly preferably a compound represented by Formula 4A from the viewpoint of simultaneously achieving high mobility and high solubility.

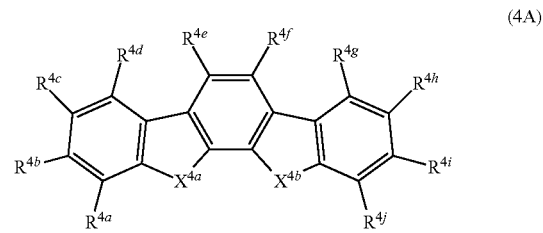

(4A)

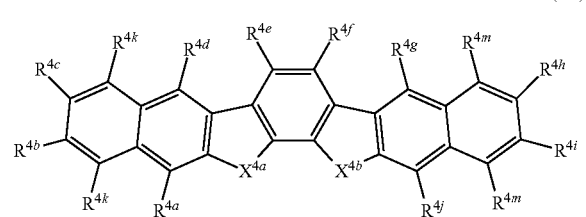

(4B)

In Formula 4A, $X^{4a}$ and $X^{4b}$ each independently represent an O atom, a S atom, or a Se atom, $R^{4a}$, $R^{4c}$ to $R^{4h}$, and $R^{4j}$ each independently represent a hydrogen atom or a halogen atom, $R^{4b}$ and $R^{4i}$ each independently represent a hydrogen atom, a halogen atom, or a group represented by Formula W, and at least one of $R^{4b}$ or $R^{4i}$ is a group represented by Formula W. Here, in a case where the group represented by Formula W is an alkyl group, the group represented by Formula W is limited to a linear alkyl group having 4 to 18 carbon atoms or a branched alkyl group having 4 or more carbon atoms.

In Formula 4B, $X^{4a}$ and $X^{4b}$ each independently represent an O atom, a S atom, or a Se atom, $R^{4a}$, $R^{4d}$ to $R^{4g}$, $R^{4j}$, $R^{4k}$, and $R^{4m}$ each independently represent a hydrogen atom or a halogen atom, $R^{4b}$, $R^{4c}$, $R^{4h}$, and $R^{4i}$ each independently represent a hydrogen atom, a halogen atom, or a group represented by Formula W, and at least one of $R^{4b}$, $R^{4c}$, $R^{4h}$, or $R^{4i}$ represents a group represented by Formula W.

—Compound Represented by Formula 5—

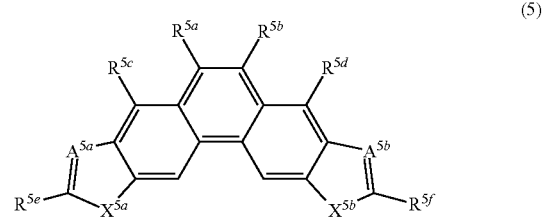

(5)

In Formula 5, $X^{5a}$ and $X^{5b}$ each independently represent $NR^{5i}$, an O atom, or a S atom. From the viewpoint of ease of synthesis, it is preferable that $X^{5a}$ and $X^{5b}$ each independently represent an O atom or a S atom. In contrast, from the viewpoint of improving the mobility, it is preferable that at least one of $X^{5a}$ or $X^{5b}$ is a S atom. It is preferable that $X^{5a}$ and $X^{5b}$ are the same linking groups. It is more preferable that both of $X^{5a}$ and $X^{5b}$ are S atoms.

$R^{5i}$ represents a hydrogen atom, an alkyl group, an alkenyl group, an alkynyl group, an acyl group, an aryl group, or a heteroaryl group. $R^{5i}$ is preferably a hydrogen atom, an alkyl group, an alkenyl group, an alkynyl group, or an acyl group, more preferably a hydrogen atom or an alkyl group, even more preferably an alkyl group having 1 to 14 carbon atoms, and preferably an alkyl group having 1 to 4 carbon atoms.

In a case where $R^{5i}$ is an alkyl group, the alkyl group may be linear, branched, or cyclic. It is preferable that $R^{5i}$ is a linear alkyl group, because then the linearity of the molecule is improved, and hence the mobility can be improved.

In Formula 5, $A^{5a}$ represents $CR^{5g}$ or a N atom, $A^{5b}$ represents $CR^{5h}$ or a N atom, and $R^{5g}$ and $R^{5h}$ each independently represent a hydrogen atom or a substituent. It is preferable that $A^{5a}$ represents $CR^{5g}$ or $A^{5b}$ represents $CR^{5h}$. It is more preferable that $A^{5a}$ represents $CR^{5g}$ and $A^{5b}$ represents $CR^{5h}$. $A^{5a}$ and $A^{5b}$ may be the same as or different from each other, but it is preferable that they are the same as each other.

In Formula 5, $R^{5e}$ and $R^{5g}$ may or may not form a ring by being bonded to each other, but it is preferable that they do not form a ring by being bonded to each other.

In Formula 5, $R^{5e}$ and $R^{5i}$ may or may not form a ring by being bonded to each other, but it is preferable that they do not form a ring by being bonded to each other.

In Formula 5, $R^{5f}$ and $R^{5h}$ may or may not form a ring by being bonded to each other, but it is preferable that they do not form a ring by being bonded to each other.

In Formula 5, $R^{5f}$ and $R^{5i}$ may or may not form a ring by being bonded to each other, but it is preferable that they do not form a ring by being bonded to each other.

In Formula 5, $R^{5a}$ to $R^{5h}$ each independently represent a hydrogen atom or a substituent, and at least one of $R^{5a}$, $R^{5b}$, $R^{5c}$, $R^{5d}$, $R^{5e}$, $R^{5f}$, $R^{5g}$, or $R^{5h}$ is a group represented by Formula W.

Examples of the substituent represented by $R^{5a}$ to $R^{5h}$ include the substituent X described above. The definition of a group represented by Formula W is as described above.

In the compound represented by Formula 5, among $R^{5a}$ to $R^{5h}$, the number of groups represented by Formula W is preferably 1 to 4 from the viewpoint of improving the mobility and improving the solubility in an organic solvent, more preferably 1 or 2, and particularly preferably 2.

A group represented by Formula W can be positioned in any of $R^{5a}$ to $R^{5h}$ without particular limitation. From the viewpoint of improving the mobility and improving the solubility in an organic solvent, the group represented by Formula W is preferably positioned in $R^{5e}$ or $R^{5f}$.

Among $R^{5a}$ to $R^{5h}$, the number of substituents other than a group represented by Formula W is preferably 0 to 4, more preferably 0 to 2, even more preferably 0 or 1, and particularly preferably 0.

In a case where $R^{5a}$ to $R^{5h}$ represent substituents other than a group represented by Formula W, each of the substituents is preferably a group having a chain length of a linking group of equal to or less than 3.7 Å, more preferably a group having a chain length of a linking group of 1.0 to 3.7 Å, even more preferably a group having a chain length of a linking group of 1.0 to 2.1 Å. The definition of a chain length of a linking group is as described above.

In a case where $R^{5a}$ to $R^{5h}$ represent substituents other than a group represented by Formula W, the substituents preferably each independently represent a substituted or unsubstituted alkyl group having 2 or less carbon atoms, a substituted or unsubstituted alkynyl group having 2 or less carbon atoms, a substituted or unsubstituted alkenyl group having 2 or less carbon atoms, or a substituted or unsubstituted acyl group having 2 or less carbon atoms, and more preferably each independently represent a substituted or unsubstituted alkyl group having 2 or less carbon atoms.

In a case where $R^{5a}$ to $R^{5h}$ represent substituents other than a group represented by Formula W, and the substituents each independently represent a substituted alkyl group having 2 or less carbon atoms, examples of substituents that the alkyl group can have include a cyano group, a fluorine atom, a deuterium atom, and the like. Among these, a cyano group is preferable. In a case where $R^{5a}$ to $R^{5h}$ represent substituents other than a group represented by Formula W, the substituted or unsubstituted alkyl group having 2 or less carbon atoms that is represented by each of the substituents is preferably a methyl group, an ethyl group, or a methyl group substituted with a cyano group, more preferably a methyl group or a methyl group substituted with a cyano group, and particularly preferably a methyl group substituted with a cyano group.

In a case where $R^{5a}$ to $R^{5h}$ represent substituents other than a group represented by Formula W, and the substituents each independently represent a substituted alkynyl group having 2 or less carbon atoms, examples of substituents that the alkynyl group can have include a deuterium atom and the like. In a case where $R^{5a}$ to $R^{5h}$ represent substituents other than a substituent represented by Formula W, examples of the substituted or unsubstituted alkynyl group having 2 or less carbon atoms that is represented by each of the substituents include an ethynyl group or an acetylene group substituted with a deuterium atom. Between these, an ethynyl group is preferable.

In a case where $R^{5a}$ to $R^{5h}$ represent substituents other than a group represented by Formula W, and the substituents each independently represent a substituted alkenyl group having 2 or less carbon atoms, examples of substituents that the alkenyl group can have include deuterium atom and the like. In a case where $R^{5a}$ to $R^{5h}$ represent substituents other than a group represented by Formula W, examples of the substituted or unsubstituted alkenyl group having 2 or less carbon atoms that is represented by each of the substituents include an ethenyl group and an ethenyl group substituted with a deuterium atom. Between these, an ethenyl group is preferable.

In a case where $R^{5a}$ to $R^{5h}$ represent substituents other than a group represented by Formula W, and the substituents each independently represent a substituted acyl group having 2 or less carbon atoms, examples of substituents that the acyl group can have include a fluorine atom and the like. In a case where $R^{5a}$ to $R^{5h}$ represent substituents other than a group represented by Formula W, examples of the substituted or unsubstituted acyl group having 2 or less carbon atoms that is represented by each of the substituents include a formyl group, an acetyl group, and an acetyl group substituted with a fluorine atom. Among these, a formyl group is preferable.

The compound represented by Formula 5 is preferably a compound represented by the following Formula 5A or 5B, and particularly preferably a compound represented by Formula 5A from the viewpoint of high mobility.

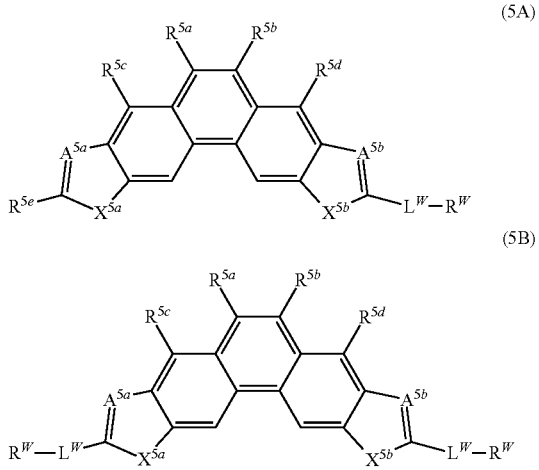

(5A)

(5B)

In Formula 5A, $X^{5a}$ and $X^{5b}$ each independently represent an O atom or a S atom. $A^{5a}$ represents $CR^{5g}$ or a N atom, and $A^{5b}$ represents $CR^{5h}$ or a N atom. The definition of each of $A^{5a}$, $A^{5b}$, $R^{5g}$, and $R^{5h}$ in Formula 5A is the same as the definition of each of $A^{5a}$, $A^{5b}$, $R^{5g}$, and $R^{5h}$ in Formula 5.

In Formula 5A, $R^{5a}$ to $R^{5e}$, $R^{5g}$, and $R^{5h}$ each independently represent a hydrogen atom or a substituent, and $R^{5e}$ is not a group represented by Formula W.

In a case where $R^{5a}$ to $R^{5e}$, $R^{5g}$, and $R^{5h}$ in Formula 5A represent a substituent, a preferred range of the substituent is the same as the preferred range established in a case where $R^{5a}$ to $R^{5h}$ in Formula 5 represent a substituent other than a group represented by Formula W.

The definition of each of $L^W$ and $R^W$ in Formula 5A is the same as the definition of each of $L^W$ and $R^W$ in Formula W described above.

In Formula 5B, $X^{5a}$ and $X^{5b}$ each independently represent an O atom or a S atom. $A^{5a}$ represents $CR^{5g}$ or a N atom, and $A^{5b}$ represents $CR^{5h}$ or a N atom. The definition of each of $A^{5a}$, $A^{5b}$, $R^{5g}$, and $R^{5h}$ in Formula 5B is the same as the definition of each of $A^{5a}$, $A^{5b}$, $R^{5g}$, and $R^{5h}$ in Formula 5.

In Formula 5B, $R^{5a}$ to $R^{5d}$, $R^{5g}$, and $R^{5h}$ each independently represent a hydrogen atom or a substituent. In a case where $R^{5a}$ to $R^{5d}$, $R^{5g}$, and $R^{5h}$ in Formula 5B represent a substituent, a preferred range of the substituent is the same as the preferred range established in a case where $R^{5a}$ to $R^{5h}$ in Formula 5 represent a substituent other than a group represented by Formula W.

The definition of each of $L^W$ and $R^W$ in Formula 5B is the same as the definition of each of $L^W$ and $R^W$ in Formula W described above. Furthermore, two $L^W$'s and two $R^W$'s in Formula 5B may be the same as or different from each other.

—Compound Represented by Formula 6—

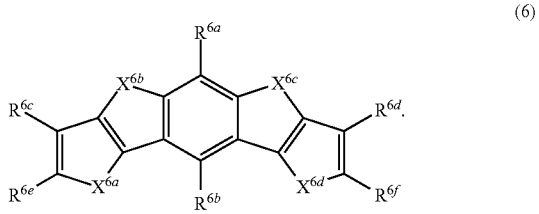

(6)

In Formula 6, $X^{6a}$ to $X^{6d}$ each independently represent $NR^{6g}$, an O atom, or a S atom, and $R^{6g}$ represents a hydrogen atom, an alkyl group, an alkenyl group, an alkynyl group, an acyl group, an aryl group, or a heteroaryl group.

From the viewpoint of ease of synthesis, it is preferable that $X^{6a}$ to $X^{6d}$ each independently represent an O atom or a S atom. In contrast, from the viewpoint of improving the mobility, at least one of $X^{6a}$, $X^{6b}$, $X^{6c}$, or $X^{6d}$ is preferably a S atom. It is preferable that $X^{6a}$ to $X^{6d}$ are the same linking groups. It is more preferable that all of $X^{6a}$ to $X^{6d}$ are S atoms.

$R^{6g}$ represents a hydrogen atom, an alkyl group, an alkenyl group, an alkynyl group, an acyl group, an aryl group, or a heteroaryl group. $R^{6g}$ is preferably a hydrogen atom, an alkyl group, an alkenyl group, an alkynyl group, or an acyl group, more preferably a hydrogen atom or an alkyl group, even more preferably an alkyl group having 1 to 14 carbon atoms, and particularly preferably an alkyl group having 1 to 4 carbon atoms.

In a case where $R^{6g}$ represents an alkyl group, the alkyl group may be linear, branched, or cyclic. However, it is preferable that $R^{6g}$ is a linear alkyl group, because then the linearity of the molecule is improved, and hence the mobility can be improved.

In Formula 6, $R^{6a}$ to $R^{6f}$ each independently represent a hydrogen atom or a substituent, and at least one of $R^{6a}$, $R^{6b}$, $R^{6c}$, $R^{6d}$, $R^{6e}$, or $R^{6f}$ represents a group represented by Formula W.

Examples of the substituents represented by $R^{6a}$ to $R^{6f}$ include the substituent X described above. The definition of a group represented by Formula W is as described above.

Among the substituents, the substituent that $R^{6a}$ to $R^{6f}$ can each independently adopt is preferably an alkyl group, an aryl group, an alkenyl group, an alkynyl group, a heterocyclic group, an alkoxy group, an alkylthio group, or a group represented by Formula W, more preferably an alkyl group having 1 to 12 carbon atoms, an aryl group having 6 to 20 carbon atoms, an alkenyl group having 2 to 12 carbon atoms, an alkynyl group having 2 to 12 carbon atoms, an alkoxy group having 1 to 11 carbon atoms, a heterocyclic group having 5 to 12 carbon atoms, an alkylthio group having 1 to 12 carbon atoms, or a group represented by Formula W, even more preferably a group, which will be described later, having a chain length of a linking group of equal to or less than 3.7 Å or a group represented by Formula W, and particularly preferably a group represented by Formula W.

In the compound represented by Formula 6, among $R^{6a}$ to $R^{6f}$, the number of groups represented by Formula W is preferably 1 to 4 from the viewpoint of improving the mobility and improving the solubility in an organic solvent, more preferably 1 or 2, and particularly preferably 2.

A group represented by Formula W can be positioned in any of $R^{6a}$ to $R^{6f}$ without particular limitation, but the group represented by Formula W is preferably positioned in $R^{6c}$ to $R^{6f}$. From the viewpoint of improving the mobility and improving the solubility in an organic solvent, the group represented by Formula W is more preferably positioned in $R^{6e}$ or $R^{6f}$.

Among $R^{6a}$ to $R^{6f}$, the number of substituents other than a group represented by Formula W is preferably 0 to 4, more preferably 0 to 2, even more preferably 0 or 1, and particularly preferably 0.

In a case where $R^{6a}$ to $R^{6f}$ represent substituents other than a group represented by Formula W, each of the substituents is preferably a group having a chain length of a linking group of equal to or less than 3.7 Å, more preferably a group having a chain length of a linking group of 1.0 to 3.7 Å, and even more preferably a group having a chain length of a linking group of 1.0 to 2.1 Å. The definition of a chain length of a linking group is as described above.

In a case where $R^{6a}$ to $R^{6f}$ represent substituents other than a group represented by Formula W, the substituents preferably each independently represent a substituted or unsubstituted alkyl group having 2 or less carbon atoms, a substituted or unsubstituted alkynyl group having 2 or less carbon atoms, a substituted or unsubstituted alkenyl group having 2 or less carbon atoms, or a substituted or unsubstituted acyl group having 2 or less carbon atoms, and more preferably each independently represent a substituted or unsubstituted alkyl group having 2 or less carbon atoms.

In a case where $R^{6a}$ to $R^{6f}$ represent substituents other than a group represented by Formula W, and the substituents each independently represent a substituted alkyl group having 2 or less carbon atoms, examples of substituents that the alkyl group can have include a cyano group, a fluorine atom, a deuterium atom, and the like. Among these, a cyano group is preferable. In a case where $R^{6a}$ to $R^{6f}$ represent substituents other than a group represented by Formula W, the substituted or unsubstituted alkyl group having 2 or less carbon atoms that is represented by each of the substituents is preferably a methyl group, an ethyl group, or a methyl group substituted with a cyano group, more preferably a methyl group or a methyl group substituted with a cyano group, and particularly preferably a methyl group substituted with a cyano group.

In a case where $R^{6a}$ to $R^{6f}$ represent substituents other than a group represented by Formula W, and the substituents each independently represent a substituted alkynyl group having 2 or less carbon atoms, examples of substituents that the alkynyl group can have include a deuterium atom and the like. In a case where $R^{6a}$ to $R^{6f}$ represent substituents other than a group represented by Formula W, examples of the substituted or unsubstituted alkynyl group having 2 or less carbon atoms that is represented by each of the substituents include an ethynyl group and an acetylene group substituted with a deuterium atom. Between these, an ethynyl group is preferable.

In a case where $R^{6a}$ to $R^{6f}$ represent substituents other than a group represented by Formula W, and the substituents each independently represent a substituted alkenyl group having 2 or less carbon atoms, examples of substituents that the alkenyl group can have include a deuterium atom and the like. In a case where $R^{6a}$ to $R^{6f}$ represent substituents other than a group represented by Formula W, examples of the substituted or unsubstituted alkenyl group having 2 or less carbon atoms that is represented by each of the substituents include an ethenyl group and an ethenyl group substituted with a deuterium atom. Between these, an ethenyl group is preferable.

In a case where $R^{6a}$ to $R^{6f}$ represent substituents other than a group represented by Formula W, and the substituents each independently represent a substituted acyl group having 2 or less carbon atoms, examples of substituents that the acyl group can have include a fluorine atom and the like. In a case where $R^{6a}$ to $R^{6f}$ represent substituents other than a group represented by Formula W, examples of the substituted or unsubstituted acyl group having 2 or less carbon atoms that is represented by each of the substituents include a formyl group, an acetyl group, and an acetyl group substituted with a fluorine atom. Among these, a formyl group is preferable.

The compound represented by Formula 6 is preferably a compound represented by the following Formula 6A or 6B, and particularly preferably a compound represented by Formula 6A from the viewpoint of high mobility.

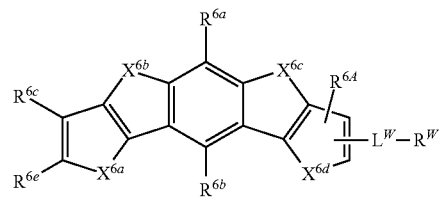

(6A)

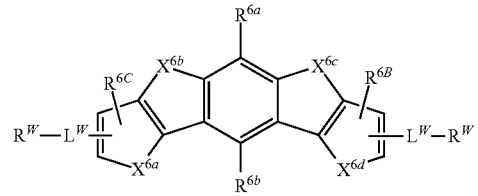

(6B)

In Formula 6A, $X^{6a}$ to $X^{6d}$ each independently represent an O atom or a S atom, $R^{6a}$ to $R^{6c}$, $R^{6A}$, and $R^{6e}$ each independently represent a hydrogen atom or a substituent, $R^{6a}$ to $R^{6c}$, $R^{6A}$, and $R^{6e}$ are not a group represented by Formula W, $R^W$ represents an alkyl group having 5 to 19 carbon atoms, and $L^W$ represents a divalent linking group represented by any one of Formulae L-1 to L-25 or a divalent linking group in which 2 or more divalent linking groups represented by any one of Formulae L-1 to L-25 are bonded to each other.

In Formula 6B, $X^{6a}$ to $X^{6d}$ each independently represent an O atom or a S atom, $R^{6a}$, $R^{6c}$, $R^{6B}$, and $R^{6C}$ each independently represent a hydrogen atom or a substituent, $R^W$ each independently represents an alkyl group having 5 to 19 carbon atoms, and $L^W$ each independently represent a divalent linking group represented by any one of Formulae L-1 to L-25 or a divalent linking group in which 2 or more divalent linking groups represented by any one of Formulae L-1 to L-25 are bonded to each other.

Examples of the aforementioned substituents include the substituents described above.

—Compound Represented by Formula 7—

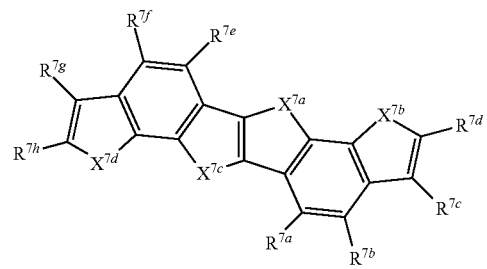

(7)

In Formula 7, $X^{7a}$ and $X^{7c}$ each independently represent a S atom, an O atom, a Se atom, or $NR^{7i}$ ($>$N—$R^{7i}$), and $X^{7b}$ and $X^{7d}$ each independently represent a S atom, an O atom, or a Se atom. From the viewpoint of ease of synthesis, it is preferable that $X^{7a}$ to $X^{7d}$ each independently represent an O atom or a S atom. In contrast, from the viewpoint of improving the carrier mobility, it is preferable that at least one of $X^{7a}$, $X^{7b}$, $X^{7c}$, or $X^{7d}$ is a S atom. It is preferable that $X^{7a}$ to $X^{7d}$ are the same linking groups. It is more preferable that all of $X^{7a}$ to $X^{7d}$ are S atoms.

In Formula 7, $R^{7a}$ to $R^{7i}$ each independently represent a hydrogen atom or a substituent, and at least one of $R^{7a}$, $R^{7b}$, $R^{7c}$, $R^{7d}$, $R^{7e}$, $R^{7f}$, $R^{7g}$, $R^{7h}$, or $R^{7i}$ is a group represented by Formula W.

Examples of the substituent represented by $R^{7a}$ to $R^{7i}$ include the substituent X described above. The definition of a group represented by Formula W is as described above.

$R^{7i}$ is preferably a hydrogen atom or an alkyl group, more preferably an alkyl group having 5 to 12 carbon atoms, and particularly preferably an alkyl group having 8 to 10 carbon atoms.

In a case where $R^{7i}$ represents an alkyl group, the alkyl group may be linear, branched, or cyclic. However, from the viewpoint of overlapping of HOMO, it is preferable that $R^{7i}$ is a linear alkyl group.

In the compound represented by Formula 7, among $R^{7a}$ to $R^{7i}$, the number of substituents represented by Formula W is preferably 1 to 4 from the viewpoint of improving the mobility and improving the solubility in an organic solvent, more preferably 1 or 2, and particularly preferably 2.

A group represented by Formula W can be positioned in any of $R^{7a}$ to $R^{7i}$ without particular limitation. The group represented by Formula W is preferably positioned in $R^{7d}$ or $R^{7h}$ from the viewpoint of improving the mobility and improving the solubility in an organic solvent, and more preferably positioned in $R^{7d}$ and $R^{7h}$.

Among $R^{7a}$ to $R^{7i}$ of Formula 7, the number of substituents other than a group represented by Formula W is preferably 0 to 4, more preferably 0 to 2, even more preferably 0 or 1, and particularly preferably 0.

In a case where $R^{7a}$ to $R^{7i}$ are substituents other than a group represented by Formula W, each of the substituents is preferably a group having a chain length of a linking group of equal to or less than 3.7 Å, more preferably a group having a chain length of a linking group of 1.0 to 3.7 Å, and even more preferably a group having a chain length of a linking group of 1.0 to 2.1 Å. The definition of a chain length of a linking group is as described above.

In a case where $R^{7a}$ to $R^{7i}$ are substituents other than a group represented by Formula W, the substituents preferably each independently represent a substituted or unsubstituted alkyl group having 2 or less carbon atoms, a substituted or unsubstituted alkynyl group having 2 or less carbon atoms, a substituted or unsubstituted alkenyl group having 2 or less carbon atoms, or a substituted or unsubstituted acyl group having 2 or less carbon atoms, and more preferably each independently represent a substituted or unsubstituted alkyl group having 2 or less carbon atoms.

In a case where $R^{7a}$ to $R^{7i}$ are substituents other than a group represented by Formula W, and the substituents each independently represent a substituted alkyl group having 2 or less carbon atoms, examples of substituents that the alkyl group can have include a cyano group, a fluorine atom, a deuterium atom, and the like. Among these, a cyano group is preferable.

In a case where $R^{7a}$ to $R^{7i}$ are substituents other than a group represented by Formula W, the substituted or unsubstituted alkyl group having 2 or less carbon atoms that is represented by each of the substituents is preferably a methyl group, an ethyl group, or a methyl group substituted with a cyano group, more preferably a methyl group or a methyl group substituted with a cyano group, and particularly preferably a methyl group substituted with a cyano group.

In a case where $R^{7a}$ to $R^{7i}$ are substituents other than a group represented by Formula W, and the substituents each independently represent a substituted alkynyl group having 2 or less carbon atoms, examples of substituents that the alkynyl group can have include a deuterium atom and the like. In a case where $R^{7a}$ to $R^{7i}$ are substituents other than a substituent represented by Formula W, examples of the substituted or unsubstituted alkynyl group having 2 or less carbon atoms that is represented by each of the substituents include an ethynyl group and an acetylene group substituted with a deuterium atom. Between these, an ethynyl group is preferable.

In a case where $R^{7a}$ to $R^{7i}$ are substituents other than a group represented by Formula W, and the substituents each independently represent a substituted alkenyl group having 2 or less carbon atoms, examples of substituents that the alkenyl group can have include a deuterium atom and the like. In a case where $R^{7a}$ to $R^{7i}$ are substituents other than a substituent represented by Formula W, examples of the substituted or unsubstituted alkenyl group having 2 or less carbon atoms that is represented by each of the substituents include an ethenyl group and an ethenyl group substituted with a deuterium atom. Between these, an ethenyl group is preferable.

In a case where $R^{7a}$ to $R^{7i}$ are substituents other than a group represented by Formula W, and the substituents each independently represent a substituted acyl group having 2 or less carbon atoms, examples of substituents that the acyl group can have include a fluorine atom and the like. In a case where $R^{7a}$ to $R^{7i}$ are substituents other than a substituent represented by Formula W, examples of the substituted or unsubstituted acyl group having 2 or less carbon atoms that is represented by each of the substituents include a formyl group, an acetyl group, and an acetyl group substituted with a fluorine atom. Among these, a formyl group is preferable.

The compound represented by Formula 7 is preferably a compound represented by the following Formula 7A or 7B, and particularly preferably a compound represented by Formula 7B from the viewpoint of high mobility.

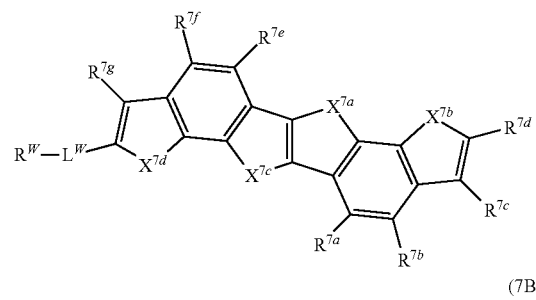

(7A)

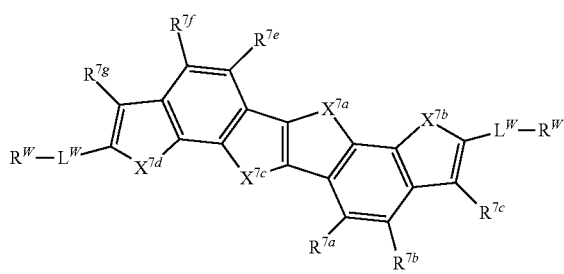

(7B)

In Formula 7A, $X^{7a}$ and $X^{7c}$ each independently represent a S atom, an O atom, a Se atom, or $NR^{7i}$, $X^{7b}$ and $X^{7d}$ each independently represent a S atom, an O atom, or a Se atom, and $R^{7a}$ to $R^{7g}$ and $R^{7i}$ each independently represent a hydrogen atom or a substituent. Here, $R^{7d}$ is not a group represented by Formula W. The definition of each of $L^W$ and $R^W$ in Formula 7A is the same as the definition of each of $L^W$ and $R^W$ in Formula W described above.

In Formula 7B, $X^{7a}$ and $X^{7c}$ each independently represent a S atom, an O atom, a Se atom, or $NR^{7i}$, $X^{7b}$ and $X^{7d}$ each independently represent a S atom, an O atom, or a Se atom, and $R^{7a}$ to $R^{7c}$, $R^{7e}$ to $R^{7g}$, and $R^{7i}$ each independently represent a hydrogen atom or a substituent. The definition of each of $L^W$ and $R^W$ in Formula 7B is the same as the definition of each of $L^W$ and $R^W$ in Formula W described above. Furthermore, two $L^W$'s and two $R^W$'s in Formula 7B may be the same as or different from each other.

—Compound Represented by Formula 8—

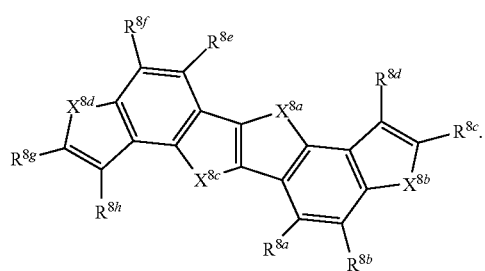

(8)

In Formula 8, $X^{8a}$ and $X^{8c}$ each independently represent a S atom, an O atom, a Se atom, or $NR^{8i}$, and $X^{8b}$ and $X^{8d}$ each independently represent a S atom, an O atom, or a Se atom. From the viewpoint of ease of synthesis, it is preferable that $X^{8a}$ to $X^{8d}$ each independently represent an O atom or a S atom. In contrast, from the viewpoint of improving the carrier mobility, it is preferable that at least one of $X^{8a}$, $X^{8b}$, $X^{8c}$, or $X^{8d}$ is a S atom. It is preferable that $X^{8a}$ to $X^{8d}$ are the same linking groups. It is more preferable that all of $X^{8a}$ to $X^{8d}$ are S atoms.

In Formula 8, $R^{8a}$ to $R^{8i}$ each independently represent a hydrogen atom or a substituent, and at least one of $R^{8a}$, $R^{8b}$, $R^{8c}$, $R^{8d}$, $R^{8e}$, $R^{8f}$, $R^{8g}$, $R^{8h}$, or $R^{8i}$ is a group represented by Formula W.

Examples of the substituent represented by $R^{8a}$ to $R^{8i}$ include the substituent X described above. The definition of a group represented by Formula W is as described above.

$R^{8i}$ is preferably a hydrogen atom or an alkyl group, more preferably an alkyl group having 5 to 12 carbon atoms, and particularly preferably an alkyl group having 8 to 10 carbon atoms.

In a case where $R^{8i}$ is an alkyl group, the alkyl group may be linear, branched, or cyclic. From the viewpoint of the overlapping of HOMO, $R^{8i}$ is preferably a linear alkyl group.

In the compound represented by Formula 8, among $R^{8a}$ to $R^{8i}$, the number of substituents represented by Formula W is preferably 1 to 4 from the viewpoint of improving the mobility and improving the solubility in an organic solvent, more preferably 1 or 2, and particularly preferably 2.

A group represented by Formula W can be positioned in any of $R^{8a}$ to $R^{8i}$ without particular limitation. The group represented by Formula W is preferably positioned in $R^{8c}$ or $R^{8g}$ from the viewpoint of improving the mobility and improving the solubility in an organic solvent, and more preferably positioned in $R^{8c}$ and $R^{8g}$.

Among $R^{8a}$ to $R^{8i}$ of Formula 8, the number of substituents other than a group represented by Formula W is preferably 0 to 4, more preferably 0 to 2, even more preferably 0 or 1, and particularly preferably 0.

In a case where $R^{8a}$ to $R^{8i}$ are substituents other than a group represented by Formula W, each of the substituents is preferably a group having a chain length of a linking group of equal to or less than 3.7 Å, more preferably a group having a chain length of a linking group of 1.0 to 3.7 Å, and even more preferably a group having a chain length of a linking group of 1.0 to 2.1 Å. The definition of a chain length of a linking group is as described above.

In a case where $R^{8a}$ to $R^{8i}$ are substituents other than a group represented by Formula W, the substituents preferably each independently represent a substituted or unsubstituted alkyl group having 2 or less carbon atoms, a substituted or unsubstituted alkynyl group having 2 or less carbon atoms, a substituted or unsubstituted alkenyl group having 2 or less carbon atoms, or a substituted or unsubstituted acyl group having 2 or less carbon atoms, and more preferably each independently represent a substituted or unsubstituted alkyl group having 2 or less carbon atoms.

In a case where $R^{8a}$ to $R^{8i}$ are substituents other than a group represented by Formula W, and the substituents each independently represent a substituted alkyl group having 2 or less carbon atoms, examples of substituents that the alkyl group can have include a cyano group, a fluorine atom, a deuterium atom, and the like. Among these, a cyano group is preferable. In a case where $R^{8a}$ to $R^{8i}$ are substituents other than a group represented by Formula W, the substituted or unsubstituted alkyl group having 2 or less carbon atoms that is represented by each of the substituents is preferably methyl group, an ethyl group, or a methyl group substituted with a cyano group, more preferably a methyl group or a methyl group substituted with a cyano group, and particularly preferably a methyl group substituted with a cyano group.

In a case where $R^{8a}$ to $R^{8i}$ are substituents other than a group represented by Formula W, and the substituents each independently represent a substituted alkynyl group having 2 or less carbon atoms, examples of substituents that the alkynyl group can have include a deuterium atom and the like. In a case where $R^{8a}$ to $R^{8i}$ are substituents other than a group represented by Formula W, examples of the substituted or unsubstituted alkynyl group having 2 or less carbon atoms that is represented by each of the substituents include an ethynyl group and an acetylene group substituted with a deuterium atom. Between these, an ethynyl group is preferable.

In a case where $R^{8a}$ to $R^{8i}$ are substituents other than a group represented by Formula W, and the substituents each independently represent a substituted alkenyl group having 2 or less carbon atoms, examples of substituents that the alkenyl group can have include a deuterium atom and the like. In a case where $R^{8a}$ to $R^{8i}$ are substituents other than a group represented by Formula W, examples of the substituted or unsubstituted alkenyl group having 2 or less carbon atoms that is represented by each of the substituents include an ethenyl group and an ethenyl group substituted with a deuterium atom. Between these, an ethenyl group is preferable.

In a case where $R^{8a}$ to $R^{8i}$ are substituents other than a group represented by Formula W, and the substituents each independently represent a substituted acyl group having 2 or less carbon atoms, examples of substituents that the acyl group can have include a fluorine atom and the like. In a case where $R^{8a}$ to $R^{8i}$ are substituents other than a group represented by Formula W, examples of the substituted or unsubstituted acyl group having 2 or less carbon atoms that is represented by each of the substituents include a formyl group, an acetyl group, and an acetyl group substituted with a fluorine atom. Among these, a formyl group is preferable.

The compound represented by Formula 8 is preferably a compound represented by the following Formula 8A or 8B, and particularly preferably a compound represented by Formula 8B from the viewpoint of high mobility.

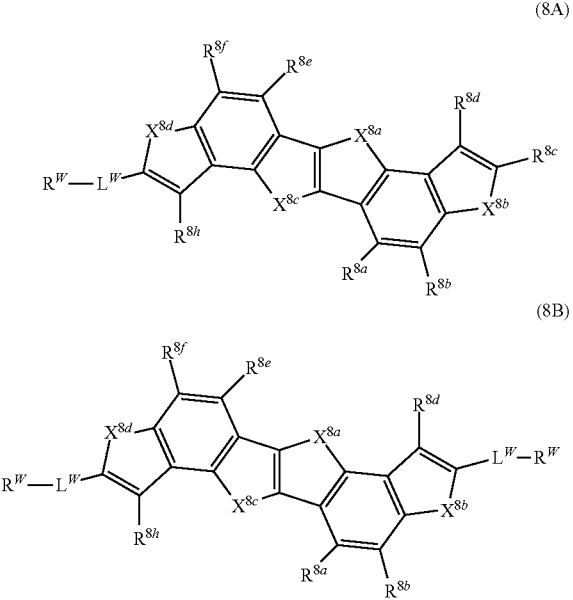

In Formula 8A, $X^{8a}$ and $X^{8c}$ each independently represent a S atom, an O atom, a Se atom, or $NR^{8i}$, $X^{8b}$ and $X^{8d}$ each independently represent a S atom, an O atom, or a Se atom, and $R^{8a}$ to $R^{8f}$ and $R^{8h}$ each independently represent a hydrogen atom or a substituent. Here, $R^{8c}$ is not a group represented by Formula W. The definition of each of $L^W$ and $R^W$ in Formula 8A is the same as the definition of each of $L^W$ and $R^W$ in Formula W described above.

In Formula 8B, $X^{8a}$ and $X^{8c}$ each independently represent a S atom, an O atom, a Se atom, or $NR^{8i}$, $X^{8b}$ and $X^{8d}$ each independently represent a S atom, an O atom, or a Se atom, and $R^{8a}$, $R^{8b}$, $R^{8d}$ to $R^{8f}$, and $R^{8h}$ each independently represent a hydrogen atom or a substituent. The definition of each of $L^W$ and $R^W$ in Formula 8B is the same as the definition of each of $L^W$ and $R^W$ in Formula W described above. Furthermore, two $L^W$'s and two $R^W$'s in Formula 8B may be the same as or different from each other.

—Compound Represented by Formula 9—

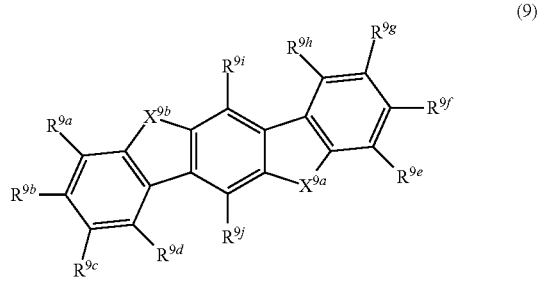

In Formula 9, $X^{9a}$ and $X^{9b}$ each independently represent an O atom, a S atom, or a Se atom. Among these, a S atom is preferable.

$R^{9c}$, $R^{9d}$, and $R^{9g}$ to $R^{9j}$ each independently represent a hydrogen atom, a halogen atom, or a substituent represented by Formula W. The definition of a group represented by Formula W is as described above.

$R^{9a}$, $R^{9b}$, $R^{9e}$, and $R^{9f}$ each independently represent a hydrogen atom or a substituent. Examples of the substituent represented by $R^{9a}$, $R^{9b}$, $R^{9e}$, and $R^{9f}$ include the substituent X described above.

It is preferable that $R^{9c}$, $R^{9d}$, and $R^{9g}$ to $R^{9j}$ each independently represent a hydrogen atom, a halogen atom, or a group represented by Formula W (here, $L^W$ is a group represented by any one of Formulae L-3, L-5, L-7 to L-9, and L-12 to L-24). Among these, $R^{9c}$, $R^{9d}$, and $R^{9g}$ to $R^{9j}$ more preferably represent a hydrogen atom.

$L^W$ is preferably a group represented by any one of Formulae L-3, L-5, L-13, L-17, and L-18.

It is preferable that at least one of $R^{9a}$, $R^{9b}$, $R^{9c}$, $R^{9d}$, $R^{9e}$, $R^{9f}$, $R^{9g}$, $R^{9h}$, or $R^{9i}$ is a group represented by Formula W.

In the compound represented by Formula 9, among $R^{9a}$ to $R^{9i}$, the number of substituents represented by Formula W is preferably 1 to 4 from the viewpoint of improving the mobility and improving the solubility in an organic solvent, more preferably 1 or 2, and particularly preferably 2.

A group represented by Formula W can be positioned in any of $R^{9a}$ to $R^{9i}$ without particular limitation. The group represented by Formula W is preferably positioned in $R^{9b}$ or $R^{9f}$ from the viewpoint of improving the mobility and improving the solubility in an organic solvent, and more preferably positioned in $R^{9b}$ and $R^{9f}$.

Among $R^{9a}$ to $R^{9i}$ of Formula 9, the number of substituents other than a group represented by Formula W is preferably 0 to 4, more preferably 0 to 2, particularly preferably 0 or 1, and more particularly preferably 0.

—Compound Represented by Formula 10—

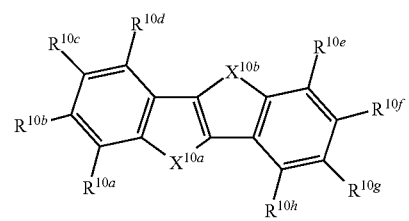

In Formula 10, $R^{10a}$ to $R^{10h}$ each independently represent a hydrogen atom or a substituent, and at least one of $R^{10a}$, $R^{10b}$, $R^{10c}$, $R^{10d}$, $R^{10e}$, $R^{10f}$, $R^{10g}$, or $R^{10h}$ represents a group represented by Formula W. Examples of the substituent represented by $R^{10a}$ to $R^{10h}$ include the substituent X described above. The definition of a substituent represented by Formula W is as described above.

It is preferable that $R^{10a}$ to $R^{10h}$ each independently represent a hydrogen atom, a halogen atom, or a substituent, and at least one of $R^{10a}$, $R^{10b}$, $R^{10c}$, $R^{10d}$, $R^{10e}$, $R^{10f}$, $R^{10g}$, or $R^{10h}$ is a substituted or unsubstituted arylthio group, a substituted or unsubstituted heteroarylthio group, a substituted or unsubstituted alkyloxycarbonyl group, a substituted or unsubstituted aryloxycarbonyl group, or a substituted or unsubstituted alkylamino group.

Among $R^{10a}$ to $R^{10h}$ of Formula 10, at least one of $R^{10b}$ or $R^{10f}$ is preferably a substituted or unsubstituted arylthio group, a substituted or unsubstituted heteroarylthio group, a substituted or unsubstituted alkyloxycarbonyl group, a substituted or unsubstituted aryloxycarbonyl group, or a substituted or unsubstituted alkylamino group, and more preferably a substituted or unsubstituted arylthio group or a substituted or unsubstituted heteroarylthio group. It is even more preferable that both of $R^{10b}$ and $R^{10f}$ represent a substituted or unsubstituted arylthio group or a substituted or unsubstituted heteroarylthio group. It is particularly preferable that both of $R^{10b}$ and $R^{10f}$ represent a substituted or unsubstituted phenylthio group or a heteroarylthio group selected from the following group A. It is most preferable that both of $R^{10b}$ and $R^{10f}$ represent a substituted or unsubstituted phenylthio group or a heteroarylthio group represented by the following Formula A-17, A-18, or A-20.

The arylthio group is preferably a group in which a sulfur atom is linked to an aryl group having 6 to 20 carbon atoms, more preferably a naphthylthio group or a phenylthio group, and particularly preferably a phenylthio group.

The heteroarylthio group is preferably a group in which a sulfur atom is linked to a 3- to 10-membered heteroaryl group, more preferably a group in which a sulfur atom is linked to a 5- or 6-membered heteroaryl group, and particularly preferably the following group A.

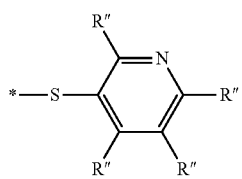
(A-14)

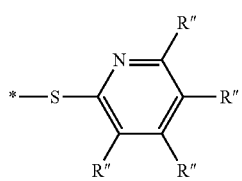
(A-15)

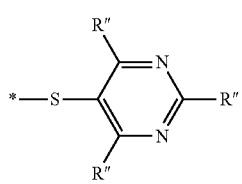
(A-16)

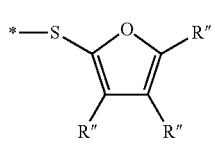
(A-17)

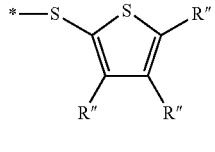
(A-18)

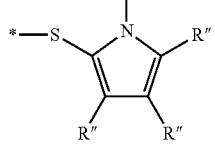
(A-20)

-continued

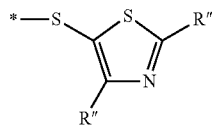
(A-21)

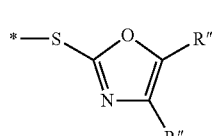
(A-23)

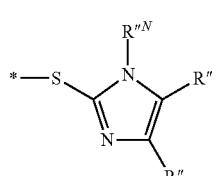
(A-24)

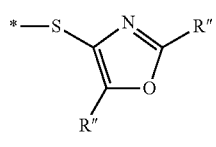
(A-26)

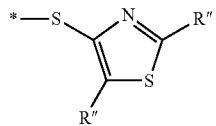
(A-27)

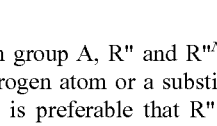

In group A, R" and $R''^N$ each independently represent a hydrogen atom or a substituent.

It is preferable that R" in group A each independently represents a hydrogen atom or a group represented by Formula W.

$R''^N$ in group A preferably represents a substituent, more preferably represents an alkyl group, an aryl group, or a heteroaryl group, even more preferably represents an alkyl group, an aryl group substituted with an alkyl group, or a heteroaryl group substituted with an alkyl group, and particularly preferably represents an alkyl group having 1 to 4 carbon atoms, a phenyl group substituted with an alkyl group having 1 to 4 carbon atoms, or a 5-membered heteroaryl group substituted with an alkyl group having 1 to 4 carbon atoms.

As the alkyloxycarbonyl group, a group in which a carbonyl group is linked to an alkyl group having 1 to 20 carbon atoms is preferable. The number of carbon atoms in the alkyl group is more preferably 2 to 15, and particularly preferably 5 to 10.

As the aryloxycarbonyl group, a group in which a carbonyl group is linked to an aryl group having 6 to 20 carbon atoms is preferable. The number of carbon atoms in the aryl group is more preferably 6 to 15, and particularly preferably 8 to 12.

As the alkylamino group, a group in which an amino group is linked to an alkyl group having 1 to 20 carbon atoms is preferable. The number of carbon atoms in the alkyl group is more preferably 2 to 15, and particularly preferably 5 to 10.

Among $R^{10a}$ to $R^{10h}$, the number of substituents (hereinafter, referred to as other substituents as well) other than a substituted or unsubstituted arylthio group, a substituted or unsubstituted heteroarylthio group, a substituted or unsubstituted alkyloxycarbonyl group, a substituted or unsubstituted aryloxycarbonyl group, or a substituted or unsubstituted alkylamino group is preferably 0 to 4, more preferably 0 to 2, even more preferably 0 or 1, and more particularly preferably 0.

$X^{10a}$ and $X^{10b}$ each independently represent a S atom, an O atom, a Se atom, or $NR^x$ (>N—$R^x$). From the viewpoint of improving the mobility, it is preferable that at least one of $X^{10a}$ or $X^{10b}$ is a S atom. It is preferable that $X^{10a}$ and $X^{10b}$ are the same linking groups. It is more preferable that both of $X^{10a}$ and $X^{10b}$ are S atoms.

$R^x$ each independently represents a hydrogen atom or a group represented by Formula W. The definition of a group represented by Formula W is as described above.

—Compound Represented by Formula 11—

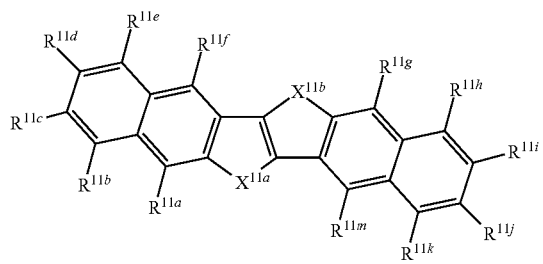

(11)

In Formula 11, $X^{11a}$ and $X^{11b}$ each independently represent a S atom, an O atom, a Se atom, or $NR^{11n}$, $R^{11a}$ to $R^{11k}$, $R^{11m}$, and $R^{11n}$ each independently represent a hydrogen atom or a substituent, and at least one of $R^{11a}$, $R^{11b}$, Rue, $R^{11d}$, $R^{11e}$, $R^{11f}$, $R^{11g}$, $R^{11h}$, $R^{11i}$, $R^{11j}$, $R^{11k}$, $R^{11m}$, or $R^{11n}$ represents a group represented by Formula W. Examples of the substituent include the substituent X described above. The definition of a substituent represented by Formula W is as described above.

In Formula 11, from the viewpoint of improving the mobility, at least one of $X^{11a}$ or $X^{11b}$ is a S atom. It is preferable that $X^{11a}$ and $X^{11b}$ are the same linking groups. It is more preferable that both of $X^{11a}$ and $X^{11b}$ are S atoms.

Among $R^{11a}$ to $R^{11k}$ and $R^{11m}$ of Formula 11, at least one of $R^{11c}$ or $R^{11i}$ is preferably a substituted or unsubstituted alkyl group, a substituted or unsubstituted arylthio group, a substituted or unsubstituted heteroarylthio group, a substituted or unsubstituted alkyloxycarbonyl group, a substituted or unsubstituted aryloxycarbonyl group, or a substituted or unsubstituted alkylamino group, and more preferably a substituted or unsubstituted alkyl group. It is even more preferable that both of $R^{11c}$ and $R^{11i}$ represent a substituted or unsubstituted alkyl group.

—Compound represented by Formula 12—

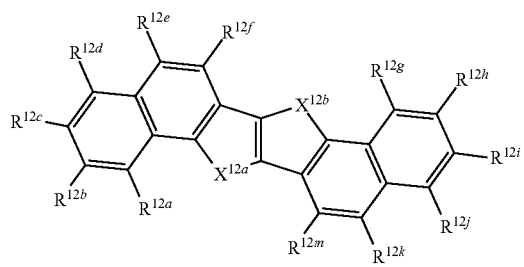

(12)

In Formula 12, $X^{12a}$ and $X^{12b}$ each independently represent a S atom, an O atom, a Se atom, or $NR^{12n}$, $R^{12a}$ to $R^{12k}$, $R^{12m}$ and $R^{12n}$ each independently represent a hydrogen atom or a substituent, and at least one of $R^{12a}$, $R^{12b}$, $R^{12c}$, $R^{12d}$, $R^{12e}$, $R^{12f}$, $R^{12g}$, $R^{12h}$, $R^{12i}$, $R^{12j}$, $R^{12k}$, $R^{12m}$, or $R^{12n}$ represents a group represented by Formula W. Examples of the substituent include the substituent X described above. The definition of a substituent represented by Formula W is as described above.

In Formula 12, from the viewpoint of improving the mobility, at least one of $X^{12a}$ or $X^{12b}$ is preferably a S atom. It is preferable that $X^{12a}$ and $X^{12b}$ are the same linking groups. It is more preferable that both of $X^{12a}$ and $X^{12b}$ are S atoms.

Among $R^{12a}$ to $R^{12k}$ and $R^{12m}$ of Formula 12, at least one of $R^{12c}$ or $R^{12i}$ is preferably a substituted or unsubstituted alkyl group, a substituted or unsubstituted arylthio group, a substituted or unsubstituted heteroarylthio group, a substituted or unsubstituted alkyloxycarbonyl group, a substituted or unsubstituted aryloxycarbonyl group, or a substituted or unsubstituted alkylamino group, and more preferably a substituted or unsubstituted alkyl group. It is even more preferable that both of $R^{12c}$ and $R^{12i}$ represent a substituted or unsubstituted alkyl group.

—Compound Represented by Formula 13—

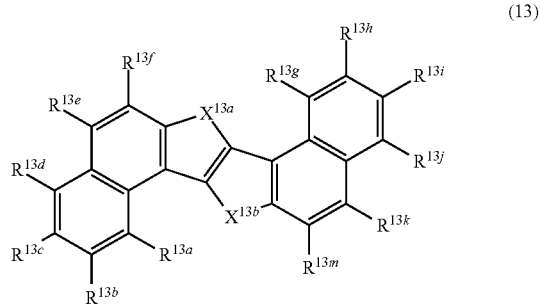

(13)

In Formula 13, $X^{13a}$ and $X^{13b}$ each independently represent a S atom, an O atom, a Se atom, or $NR^{13n}$, $R^{13a}$ to $R^{13k}$, $R^{13m}$, and $R^{13n}$ each independently represent a hydrogen atom or a substituent, and at least one of $R^{13a}$, $R^{13b}$, $R^{13c}$, $R^{13d}$, $R^{13e}$, $R^{13f}$, $R^{13g}$, $R^{13h}$, $R^{13i}$, $R^{13j}$, $R^{13k}$, $R^{13m}$, or $R^{13n}$ represents a group represented by Formula W. Examples of the substituent include the substituent X described above. The definition of a group represented by Formula W is as described above.

In Formula 13, from the viewpoint of improving the mobility, at least one of $X^{13a}$ or $X^{13b}$ is preferably a S atom. It is preferable that $X^{13a}$ and $X^{13b}$ are the same linking groups. It is more preferable that both of $X^{13a}$ and $X^{13b}$ are S atoms.

Among $R^{13a}$ to $R^{13k}$ and $R^{13m}$ of Formula 13, at least one of $R^{13c}$ or $R^{13i}$ is preferably a substituted or unsubstituted alkyl group, a substituted or unsubstituted arylthio group, a substituted or unsubstituted heteroarylthio group, a substituted or unsubstituted alkyloxycarbonyl group, a substituted or unsubstituted aryloxycarbonyl group, or a substituted or unsubstituted alkylamino group, and more preferably a substituted or unsubstituted alkyl group. It is even more preferable that both of $R^{13c}$ and $R^{13i}$ represent a substituted or unsubstituted alkyl group.

—Compound Represented by Formula 14—

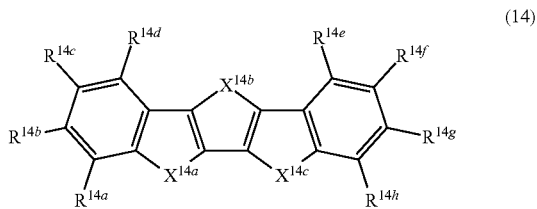

(14)

In Formula 14, $X^{14a}$ to $X^{14c}$ each independently represent a S atom, an O atom, a Se atom, or $NR^{14i}$, $R^{14a}$ to $R^{14i}$ each independently represent a hydrogen atom or a substituent, and at least one of $R^{14a}$, $R^{14b}$, $R^{14c}$, $R^{14d}$, $R^{14e}$, $R^{14f}$, $R^{14g}$, $R^{14h}$, or $R^{14i}$ represents a group represented by Formula W. Examples of the substituent include the substituent X described above. The definition of a group represented by Formula W is as described above.

In a case where at least one of $R^{14a}$, $R^{14b}$, $R^{14c}$, $R^{14d}$, $R^{14e}$, $R^{14f}$, $R^{14g}$ or $R^{14h}$ is a group represented by Formula W, and $R^W$ is an alkyl group, $L^W$ is preferably a group represented by any one of Formulae L-2 to L-25.

In Formula 14, from the viewpoint of improving the mobility, it is preferable that at least one of $X^{14a}$, $X^{14b}$, or $X^{14c}$ is a S atom. It is preferable that $X^{14a}$ to $X^{14c}$ are the same linking groups. It is more preferable that all of $X^{14a}$ to $X^{14c}$ are S atoms.

In a case where $R^W$ is an alkyl group, $L^W$ is preferably a group represented by any one of Formulae L-2 to L-5, L-13, L-17, and L-18, and more preferably a group represented by any one of Formulae L-3, L-13, and L-18.

Among $R^{14a}$ to $R^{14h}$ of Formula 14, at least one of $R^{14b}$ or $R^{14g}$ is preferably a group represented by Formula W. It is more preferable that both of $R^{14b}$ and $R^{14g}$ represent a group represented by Formula W.

—Compound Represented by Formula 15—

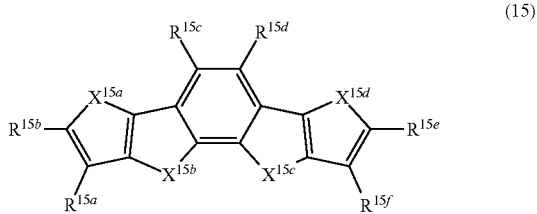

(15)

In Formula 15, $X^{15a}$ to $X^{15d}$ each independently represent a S atom, an O atom, a Se atom, or $NR^{15g}$, $R^{15a}$ to $R^{15g}$ each independently represent a hydrogen atom or a substituent, and at least one of $R^{15a}$, $R^{15b}$, $R^{15c}$, $R^{15d}$, $R^{15e}$, $R^{15f}$, or $R^{15g}$ represents a group represented by Formula W. Examples of the substituent include the substituent X described above. The definition of a group represented by Formula W is as described above.

In Formula 15, from the viewpoint of improving the mobility, at least one of $X^{15a}$, $X^{15b}$, $X^{15c}$, or $X^{15d}$ is preferably a S atom. It is preferable that $X^{15a}$ to $X^{15d}$ are the same linking groups. It is more preferable that all of $X^{15a}$ to $X^{15d}$ are S atoms.

Among $R^{15a}$ to $R^{15f}$ of Formula 15, at least one of $R^{15b}$ or $R^{15e}$ is preferably a group represented by Formula W. It is more preferable that both of $R^{15b}$ and $R^{15e}$ represent a group represented by Formula W.

—Compound Represented by Formula 16—

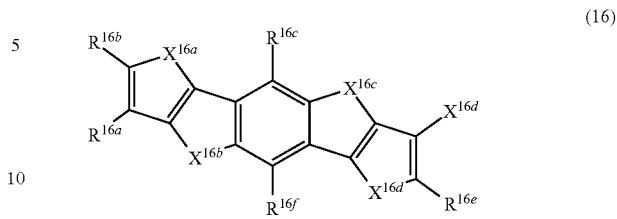

(16)

In Formula 16, $X^{16a}$ to $X^{16d}$ each independently represent a S atom, an O atom, a Se atom, or $NR^{16g}$. $R^{16a}$ to $R^{16g}$ each independently represent a hydrogen atom or a substituent, and at least one of $R^{16a}$, $R^{16b}$, $R^{16c}$, $R^{16d}$, $R^{16e}$, $R^{16f}$, or $R^{16g}$ represents a group represented by Formula W. Examples of the substituent include the substituent X described above. The definition of a group represented by Formula W is as described above.

$R^{16c}$ and $R^{16f}$ preferably represent a hydrogen atom, a halogen atom, or a group represented by Formula W (here, $L^W$ is a group represented by any one of Formulae L-3, L-5, L-7 to L-9, and L-12 to L-24). It is preferable that $R^{16a}$, $R^{16b}$, $R^{16d}$, $R^{16e}$, and $R^{16g}$ each independently represent a hydrogen atom or a substituent.

In Formula 16, $L^W$ is a group represented by any one of Formulae L-3, L-5, L-7 to L-9, and L-12 to L-24. In a case where $R^{16c}$ and $R^{16f}$ each represent a group represented by Formula W, $L^W$ is preferably a group represented by any one of Formulae L-3, L-5, L-13, L-17, and L-18.

In Formula 16, from the viewpoint of improving the mobility, at least one of $X^{16a}$, $X^{16b}$, $X^{16c}$, or $X^{16d}$ is a S atom. It is preferable that $X^{16a}$ to $X^{16d}$ are the same linking groups. It is more preferable that all of $X^{16a}$ to $X^{16d}$ are S atoms.

It is preferable that at least one of $R^{16a}$ or $R^{16d}$ among $R^{16a}$ to $R^{16f}$ of Formula 16 represents a group represented by Formula W. It is more preferable that both of $R^{16a}$ and $R^{16d}$ represent a group represented by Formula W.

Furthermore, it is preferable that $R^{16c}$ and $R^{16f}$ represent a hydrogen atom.

Component A-1 preferably has an alkyl group, more preferably has an alkyl group having 6 to 20 carbon atoms, and even more preferably has an alkyl group having 7 to 14 carbon atoms, on a condensed polycyclic aromatic ring in the aforementioned condensed polycyclic aromatic group. In a case where the above aspect is adopted, the mobility and the heat stability of the obtained organic semiconductor are further improved.

Furthermore, Component A-1 preferably has 1 or more alkyl groups, more preferably has 2 to 4 alkyl groups, and even more preferably has 2 alkyl groups, on a condensed polycyclic aromatic ring in the aforementioned condensed polycyclic aromatic group. In a case where the above aspect is adopted, the mobility and the heat stability of the obtained organic semiconductor are further improved.

The method for synthesizing Component A-1 is not particularly limited, and Component A-1 can be synthesized with reference to known methods. Examples of methods for synthesizing the compounds represented by Formulae 1 to 16 include the methods disclosed in Journal of American Chemical Society, 116, 925 (1994), Journal of Chemical Society, 221 (1951), Org. Lett., 2001, 3, 3471, Macromolecules, 2010, 43, 6264, Tetrahedron, 2002, 58, 10197, JP2012-513459A, JP2011-46687A, Journal of Chemical Research. Miniprint, 3, 601-635 (1991), Bull. Chem. Soc.

Japan, 64, 3682-3686 (1991), Tetrahedron Letters, 45, 2801-2803 (2004), EP2251342A, EP2301926A, EP2301921A, KR10-2012-0120886A, J. Org. Chem., 2011, 696, Org. Lett., 2001, 3, 3471, Macromolecules, 2010, 43, 6264, J. Org. Chem., 2013, 78, 7741, Chem. Eur. J., 2013, 19, 3721, Bull. Chem. Soc. Jpn., 1987, 60, 4187, J. Am. Chem. Soc., 2011, 133, 5024, Chem. Eur. J. 2013, 19, 3721, Macromolecules, 2010, 43, 6264-6267, J. Am. Chem. Soc., 2012, 134, 16548-16550, and the like.

From the viewpoint of the mobility of the organic semiconductor, Component A preferably contains at least one kind of compound represented by any one of Formulae 1 to 9, 14, and 15, and more preferably contains at least one kind of compound represented by any one of Formulae 1 to 9 and 15.

Specific preferred examples of Component A will be shown below, but it goes without saying that the present invention is not limited thereto. Herein, Et represents an ethyl group.

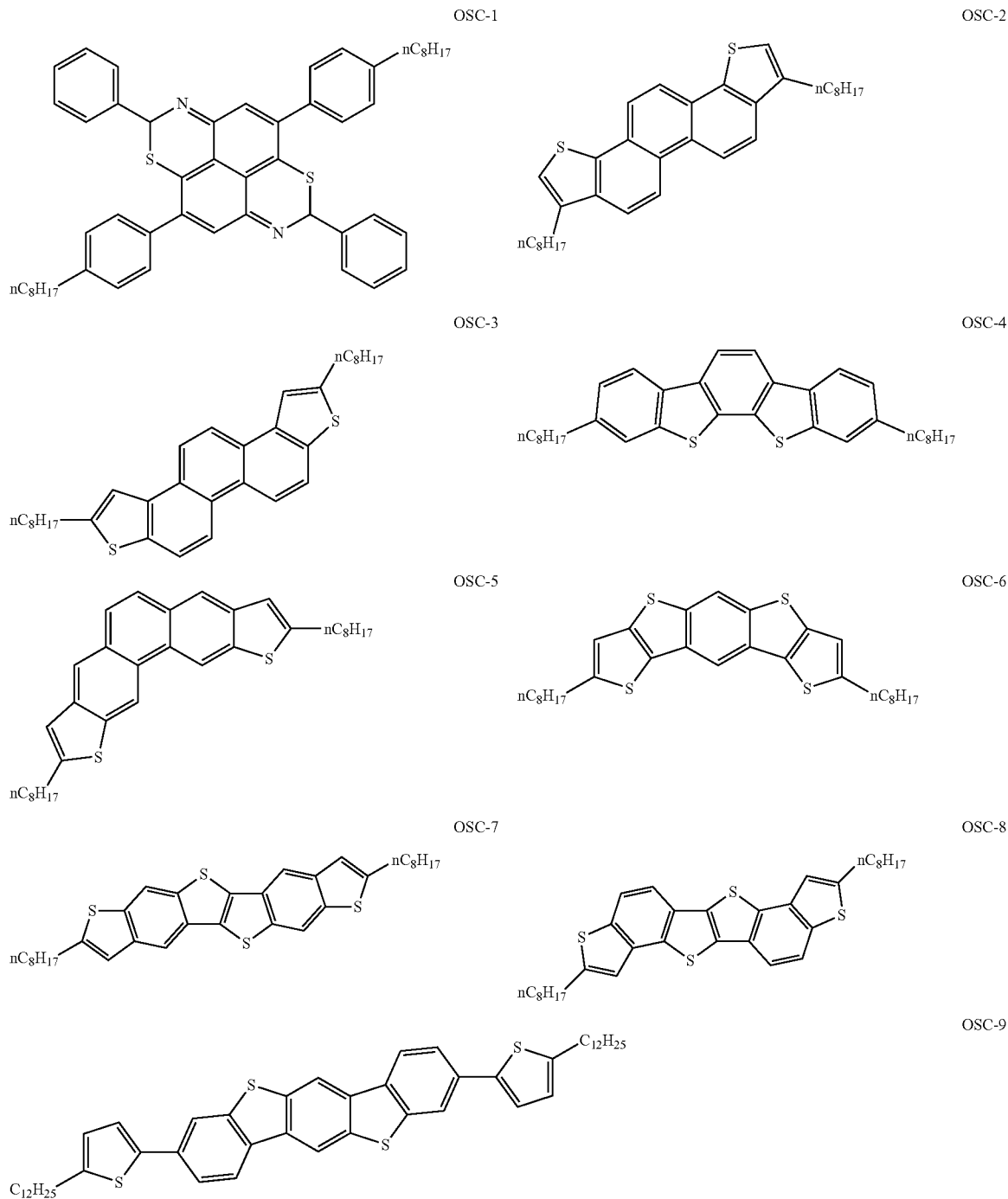

-continued
OSC-10
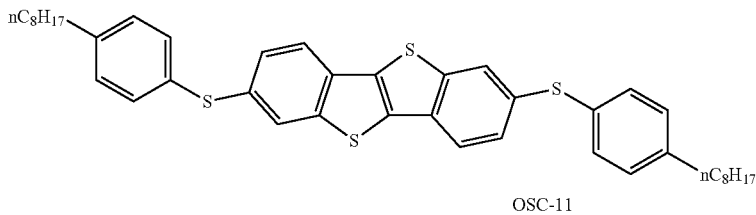
OSC-11
OSC-12
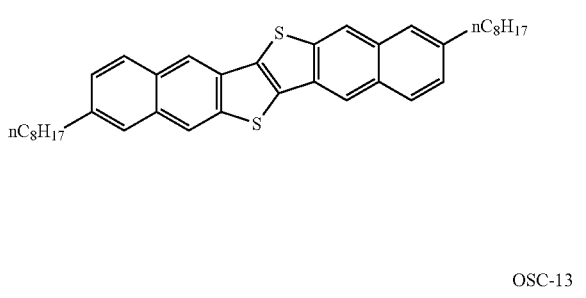
OSC-13
OSC-14
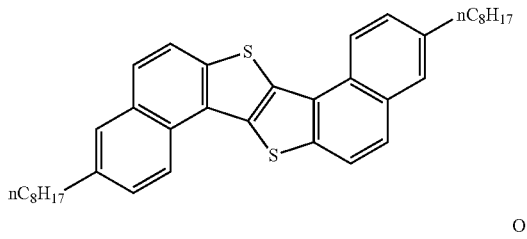
OSC-15
OSC-16
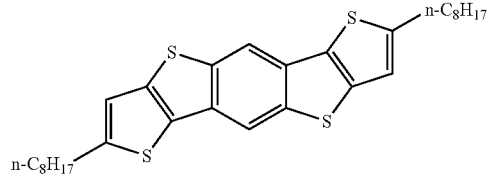
OSC-17
OSC-18
OSC-19
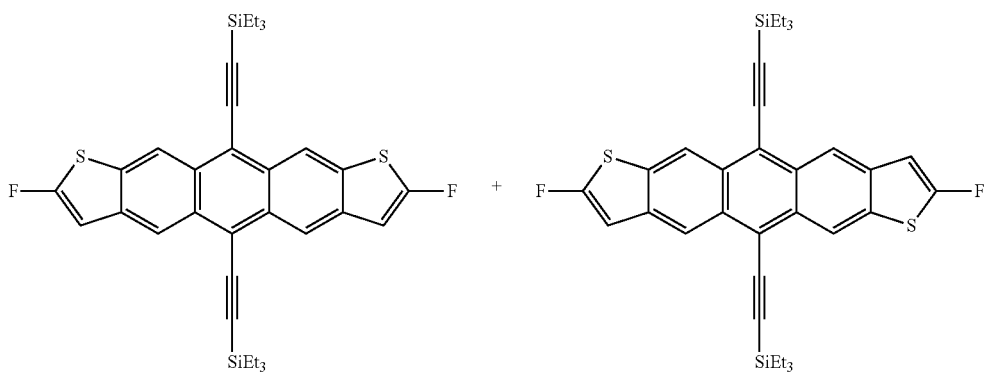

The molecular weight of Component A is not particularly limited, but is preferably equal to or less than 3,000, more preferably equal to or less than 2,000, even more preferably equal to or less than 1,000, and particularly preferably equal to or less than 850. In a case where the molecular weight is equal to or less than the aforementioned upper limit, the solubility in a solvent can be improved. In contrast, from the viewpoint of film uniformity of a thin film, the molecular weight is preferably equal to or greater than 300, more preferably equal to or greater than 350, and even more preferably equal to or greater than 400.

The content of Component A in the organic semiconductor composition of the present invention is, with respect to the total mass of the composition, preferably 0.01% to 20% by mass, more preferably 0.05% to 10% by mass, and even more preferably 0.2% to 5% by mass. In a case where the content is within the above range, the film formability becomes excellent, and an organic semiconductor film can be easily formed.

Component B: organic solvent which is represented by Formula B-1 and has melting point of equal to or lower than 25° C. and boiling point of equal to or higher than 150° C. and equal to or lower than 280° C.

The organic semiconductor composition of the present invention contains, as Component B, an organic solvent which is represented by Formula B-1 and has a melting point of equal to or lower than 25° C. and a boiling point of equal to or higher than 150° C. and equal to or lower than 280° C.

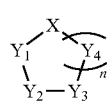

(B-1)

In Formula B-1, X represents O, S, S=O, O=S=O, or NR; $Y_1$ to $Y_4$ each independently represent $NR_1$ or $CR_{10}R_{11}$; R, $R_1$, $R_{10}$, and $R_{11}$ each independently represent a hydrogen atom or a substituent; n represents 1 or 2; in a case where n is 2, two $Y_4$'s may be the same as or different from each other; in a case where X is NR, a substituent on $Y_1$ or $Y_4$ and the substituent R on N may form a ring or may form a double bond in a 5-membered or 6-membered ring containing X by being bonded to each other; substituents of $Y_1$ to $Y_4$ adjacent to each other may form a ring or may form a double bond in a 5-membered or 6-membered ring containing X by being bonded to each other; and in a case where X is O, a substituent of $Y_1$ and a substituent of $Y_2$ do not form a double bond by being bonded to each other.

The boiling point of Component B is equal to or higher than 150° C. and equal to or lower than 280° C. In a case where the boiling point is less than 150° C., high water resistance deteriorates, and as a result, the film uniformity deteriorates. In a case where the boiling point is higher than 280° C., it is difficult to remove Component B, and an element with high mobility is not easily obtained.

The boiling point of Component B is preferably 160° C. to 250° C., more preferably 180° C. to 240° C., even more preferably 200° C. to 240° C., and particularly preferably 200° C. to 220° C.

The boiling point of Component B is measured under 1 atm (760 mmHg, $1.013 \times 10^5$ Pa) according to a common method. Furthermore, as the boiling point of Component B, the value described in various documents can be adopted.

In the present invention, Component B is a liquid at room temperature (25° C.) under 1 atm. That is, the melting point of Component B is equal to or lower than 25° C., preferably equal to or lower than 20° C., and more preferably equal to or lower than 10° C.

X in Formula B-1 is preferably O, S, S=O, or NR, more preferably O, S, or NR, and even more preferably S.

Three out of $Y_1$ to $Y_4$ preferably each independently represent $CR_{10}CR_{11}$. It is more preferable that $Y_1$ to $Y_4$ each independently represent $CR_{10}CR_{11}$.

The substituent represented by R, $R_1$, $R_{10}$, and $R_{11}$ is preferably a halogen atom, a saturated or unsaturated hydrocarbon group, an alkylthio group, or an alkyloxycarbonyl group, and more preferably a halogen atom or a saturated or unsaturated hydrocarbon group.

The number of carbon atoms in the substituent represented by R, $R_1$, $R_{10}$, and $R_{11}$ is preferably 0 to 20, more preferably 0 to 12, and even more preferably 0 to 5.

The ring formed in a case where the substituent on $Y_1$ or $Y_4$ and the substituent R on N are bonded to each other and the ring formed in a case where the substituents of $Y_1$ to $Y_4$ adjacent to each other are bonded to each other may be a saturated aliphatic ring, an unsaturated aliphatic ring, an aromatic ring, or a heterocyclic aromatic ring.

The substituent on $Y_1$ or $Y_4$ and the substituent R on N may form a double bond in a 5-membered or 6-membered ring containing X by being bonded to each other, or the substituents of $Y_1$ to $Y_4$ adjacent to each other may form a double bond in a 5-membered or 6-membered ring containing X by being bonded to each other. Here, in a case where X is O, the substituent of $Y_1$ and the substituent of $Y_2$ do not form a double bond by being bonded to each other.

Component B is preferably an organic solvent which is represented by the following Formula B-2 and has a melting point of equal to or lower than 25° C. and a boiling point of equal to or higher than 150° C. and equal to or lower than 280° C.

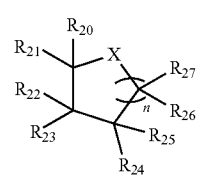

(B-2)

In Formula B-2, X represents O, S, S=O, O=S=O, or NR; n represents 1 or 2; R and $R_{20}$ to $R_{27}$ each independently represent a hydrogen atom or a substituent; in a case where n is 2, two $R_{26}$'s and two $R_{27}$'s may be the same as or different from each other; two out of R and $R_{20}$ to $R_{27}$ may form a ring by being bonded to each other; R and $R_{20}$, $R_{20}$ and $R_{22}$, $R_{22}$ and $R_{24}$, and $R_{24}$ and $R_{26}$ may form a double bond in a 5-membered or 6-membered ring containing X by being bonded to each other; and in a case where X is O, $R_{20}$ and $R_{22}$ do not form a double bond by being bonded to each other.

X in Formula B-2 is preferably O, S, S=O, or NR, more preferably O, S, or NR, and even more preferably S.

The substituent represented by R and $R_{20}$ to $R_{27}$ is preferably a halogen atom, a saturated or unsaturated hydrocarbon group, an alkylthio group, or an ester group (alkyloxycarbonyl group), more preferably a halogen atom or a saturated or unsaturated hydrocarbon group, and even more preferably a halogen atom.

The number of carbon atoms in the substituent represented by R and $R_{20}$ to $R_{27}$ is preferably 0 to 20, more preferably 0 to 12, and even more preferably 0 to 5.

The ring formed in a case where two out of R and $R_{20}$ to $R_{27}$ are bonded to each other may be a saturated aliphatic ring, an unsaturated aliphatic ring, an aromatic ring, or a heterocyclic aromatic ring, but is preferably a saturated or unsaturated hydrocarbon ring or an aromatic ring.

R and $R_{20}$, $R_{20}$ and $R_{22}$, $R_{22}$ and $R_{24}$, and $R_{24}$ and $R_{26}$ may form a double bond in a 5-membered or 6-membered ring containing X by being bonded to each other. Here, in a case where X is O, $R_{20}$ and $R_{22}$ do not form a double bond by being bonded to each other.

Component B is more preferably an organic solvent which is represented by any one of the following Formulae B-3 to B-6 and has a melting point of equal to or lower than 25° C. and a boiling point of equal to or higher than 150° C. and equal to or lower than 280° C.

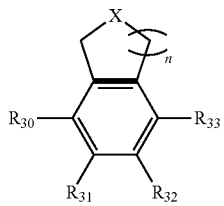

(B-3)

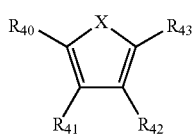

(B-4)

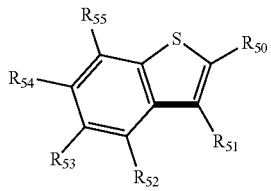

(B-5)

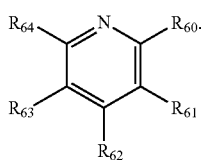

(B-6)

In Formulae B-3 to B-6, X represents an oxygen atom or a sulfur atom; n represents 1 or 2; $R_{30}$ to $R_{33}$, $R_{40}$ to $R_{43}$, $R_{50}$ to $R_{55}$, and $R_{60}$ to $R_{64}$ each independently represent a hydrogen atom or a substituent; at least one of $R_{40}$, $R_{41}$, $R_{42}$, or $R_{43}$ represents a halogen atom; and $R_{60}$ and $R_{61}$ and $R_{61}$ and $R_{62}$ may form a ring by being linked to each other.

$R_{30}$ to $R_{33}$, $R_{40}$ to $R_{43}$, $R_{50}$ to $R_{55}$, and $R_{60}$ to $R_{64}$ in Formulae B-3 to B-6 preferably each independently represent a hydrogen atom, a halogen atom, or an alkyl group.

The number of carbon atoms in the substituent in $R_{30}$ to $R_{33}$, $R_{40}$ to $R_{43}$, $R_{50}$ to $R_{55}$, and $R_{60}$ to $R_{64}$ in Formulae B-3 to B-6 is preferably 0 to 20, more preferably 0 to 12, and even more preferably 0 to 5.

X in Formula B-3 is preferably an oxygen atom.

$R_{30}$ to $R_{33}$ in Formula B-3 preferably each independently represent a hydrogen atom or an alkyl group, and more preferably each independently represent a hydrogen atom.

X in Formula B-4 is preferably a sulfur atom.

$R_{40}$ to $R_{43}$ in Formula B-4 preferably each independently represent a hydrogen atom, a halogen atom, an alkyl group, or an ester group, more preferably each independently represent a hydrogen atom, a chlorine atom, a bromine atom, an alkyl group, or an ester group, even more preferably each independently represent a hydrogen atom, a chlorine atom, a bromine atom, or an ester group, and particularly preferably each independently represent a hydrogen atom or a bromine atom.

In Formula B-4, at least two out of $R_{40}$ to $R_{43}$ are preferably halogen atoms. It is more preferable that $R_{40}$ and $R_{43}$ each independently represent a halogen atom.

$R_{50}$ to $R_{55}$ in Formula B-5 preferably represent a hydrogen atom or an alkyl group.

At least one of $R_{50}$ or $R_{51}$ in Formula B-5 is more preferably an alkyl group.

$R_{60}$ to $R_{64}$ in Formula B-6 preferably each independently represent a hydrogen atom, a halogen atom, or an alkyl group.

In Formula B-6, $R_{60}$ and $R_{61}$ or $R_{61}$ and $R_{62}$ preferably form a ring by being bonded to each other, more preferably form a hydrocarbon ring, and particularly preferably form a cyclohexene ring including an unsaturated bond of a pyridine ring.

Particularly, Component B is even more preferably an organic solvent represented by any one of Formulae B-3 to B-5 and particularly preferably an organic solvent represented by Formula B-4 from the viewpoint of excellent solubility of Component A.

Preferred specific examples of Component B will be shown below, but it goes without saying that the present invention is not limited thereto. All of the following compounds have a melting point of equal to or lower than 25° C. and a boiling point of equal to or higher than 150° C. and equal to or lower than 280° C.

Compounds containing S atom: 2-n-octylthiophene, 3-butylthiophene, ethylenedioxythiophene, 2-acetylthiophene, 2,5-dibromothiophene, 3,4-dibromothiophene, 2,3-dibromothiophene, 3-methylbenzo[b]thiophene, 2,5-dichlorothiophene, 2,5-dichloro-3-methylthiophene, 3-acetyl-2,5-dimethylthiophene, 5-bromo-2-chlorothiophene, 3-bromo-2-chlorothiophene, 2-tert-butylthiophene, 3-tert-butylthiophene, 2-methyl-3,5-dibromothiophene, thieno[2,3-b]thiophene, 2,3,4,5-tetramethylthiophene, 2,3,4-trimethylthiophene, 2,3-dichlorothiophene, 2,3,5-trichlorothiophene, 2,3,4-trichlorothiophene, 2-bromo-3-methylthiophene, 2,5-dibromo-3-methylthiophene, 2-bromo-5-methylthiophene, methyl 2-thiophene carboxylate, ethyl 2-thiophene carboxylate, 3-cyanothiophene, thiophene-2-acetonitrile, thiophene-3-acetonitrile, 2-(2-thienyl)-1,3-dioxolane, 3-(2-thienyl)-1,3-dioxolane, tetramethylene sulfoxide, 2,3-dihydrobenzo[b]thiophene, 3-methylbenzo[b]thiophene, 3-methyl-2,2'-bithiophene Compounds containing O atom: 2,3-dihydrobenzofuran, 2,3-dihydro-2-methylbenzofuran, 1,3-dihydroisobenzofuran, 1,4-cineole, 3,4-dihydro-1H-2-benzopyran, 3,4-dihydro-1H-1-benzopyran Compounds containing nitrogen atom: 2-bromopyridine, 2-bromo-4-methylpyridine, 2-bromo-4-fluoropyridine, 2-bromo-5-fluoropyridine, 2-bromo-6-fluoropyridine, 2-bromo-6-methoxypyridine, 3-bromopyridine, 3-bromo-2-methylpyridine, 4-bromo-2-methylpyridine, 2,4,6-trimethylpyridine, phenyl tetrahydropyridine, 1,3,5-trimethylhexahydro-1,3,5-triazine, 1,2-di(piperidin-1-yl)ethane, 4-phenyl-1-methyl-piperidine, 4-isobutylmorpholine, 4-butylmorpholine, 1-morpholino-1-cyclopentene, 1-morpholino-1-cyclohexene Among these, 2,5-dichlorothiophene, 2,5-dibromothiophene, 3,4-dibromothiophene, 2,5-dichloro-3-methylthiophene, 5-bromo-2-chlorothiophene, 3-bromo-2-chlorothiophene, 2-thiophene carboxylate, 3-methylbenzo[b]thiophene, thieno[2,3-b]thiophene, 1,3-dihydroisobenzofuran and/or 3,4-dihydro-1H-2-benzofurane are preferable, 2,5-dichlorothiophene, 2,5-dibromothiophene, 3,4-dibromothiophene, 2,5-dichloro-3-methylthiophene, 5-bromo-2-chlorothiophene, and/or 3-bromo-2-chlorothiophene are more preferable, and dibromothiophene is even more preferable.

One kind of Component B may be used singly, or two or more kinds thereof may be used in combination.

The content of Component B in the composition of the present invention is, with respect to the total mass of the composition, preferably 80% to 99.9% by mass, more preferably 90% to 99.5% by mass, and even more preferably 95% to 99.0% by mass.

In the present invention, other solvents that do not correspond to Component B may be used in combination with Component B.

Provided that the content of Component B in the composition is 100 parts by mass, the content of other solvents is less than 100 parts by mass, preferably equal to or less than 50 parts by mass, more preferably equal to or less than 25 parts by mass, even more preferably equal to or less than 10 parts by mass, and particularly preferably equal to or less than 3 parts by mass. It is most preferable that the composition of the present invention does not contain other solvents.

As other solvents, known solvents can be used.

Specific examples thereof include a hydrocarbon-based solvent such as hexane, octane, decane, toluene, xylene, mesitylene, ethylbenzene, decalin, or 1-methylnaphthalene, a ketone-based solvent such as acetone, methyl ethyl ketone, methyl isobutyl ketone, or cyclohexanone, a halogenated hydrocarbon-based solvent such as dichloromethane, chloroform, tetrachloromethane, dichloroethane, trichloroethane, tetrachloroethane, chlorobenzene, dichlorobenzene, or chlorotoluene, an ester-based solvent such as ethyl acetate, butyl acetate, or amyl acetate, an alcohol-based solvent such as methanol, propanol, butanol, pentanol, hexanol, cyclohexanol, methyl cellosolve, ethyl cellosolve, or ethylene glycol, an ether-based solvent such as dibutyl ether, tetrahydrofuran, dioxane, or anisole, an amide.imide-based solvent such as N,N-dimethylformamide, N,N-dimethylacetamide, 1-methyl-2-pyrrolidone, or 1-methyl-2-imidazolidinone, a sulfoxide-based solvent such as dimethyl sulfoxide, and a nitrile-based solvent such as acetonitrile.

One kind of other solvents may be used singly, or a plurality of other solvents may be used in combination.

Among the solvents, as other solvents, a hydrocarbon-based solvent, a halogenated hydrocarbon solvent, and/or an ether-based solvent are preferable, toluene, xylene, mesitylene, tetralin, dichlorobenzene, or anisole is even more preferable, and o-dichlorobenzene is particularly preferable.

Component C: Polymer Compound

The organic semiconductor composition of the present invention preferably contains a polymer compound as Component C.

The type of the polymer compound is not particularly limited, and examples thereof include known polymer compounds. As the polymer compound, a polymer compound having a benzene ring (polymer having benzene ring group-containing monomer unit) is preferable. The content of the benzene ring group-containing monomer unit is not particularly limited, but is, with respect to all the monomer units, preferably equal to or greater than 50 mol %, more preferably equal to or greater than 70 mol %, and even more preferably equal to or greater than 90 mol %. The upper limit of the content of the benzene ring group-containing monomer unit is not particularly limited, and is 100 mol % for example.

Examples of the polymer compound include polystyrene (PS), poly(a-methylstyrene) (PaMS), poly(methylmethacrylate) (PMMA), polyvinyl phenol (PVP), poly(vinylalcohol) (PVA), poly(vinylacetate) (PVAc), polyvinyl chloride (PVC), polyvinylidene fluoride (PVDF), cyanoethyl pullulan (CYPEL), poly(divinyltetramethyldisiloxane-bis(benzocyclobutene)) (BCB), ethylene-propylene rubber, acrylonitrile-butadiene rubber, and the like, but the present invention is not limited to these.

Among these, polystyrene, poly(a-methylstyrene), polyvinyl cinnamate, poly(4-vinylphenyl), and poly(4-methylstyrene) are preferable.

The number-average molecular weight of the polymer compound is not particularly limited, but is preferably 10,000 to 5,000,000, more preferably 100,000 to 2,500,000, and even more preferably 200,000 to 2,000,000. In the present invention, the number-average molecular weight and the weight-average molecular weight are measured by gel permeation chromatography (GPC) and expressed in terms of polystyrene of which the molecular weight is known.

One kind of Component C may be used singly, or two or more kinds thereof may be used in combination.

The content of Component C is, with respect to the total mass of the organic semiconductor composition, preferably 0.001% to 10% by mass, more preferably 0.005% to 5.0% by mass, and even more preferably 0.01% to 3.0% by mass.

The content of component C is, with respect to the content of Component A, preferably 10% to 1,000% by mass, more preferably 10% to 800% by mass, and even more preferably 30% to 500% by mass.

<Other Components>

The organic semiconductor composition of the present invention may contain other components in addition to components A to C.

As other components, known additives and the like can be used.

In the organic semiconductor composition of the present invention, the content of components other than components A to C is preferably equal to or less than 10% by mass, more preferably equal to or less than 5% by mass, even more preferably equal to or less than 1% by mass, and particularly preferably equal to or less than 0.1% by mass. In a case where the content of other components is within the above range, the film formability becomes excellent, and the mobility and heat stability of the obtained organic semiconductor are further improved.

The method for manufacturing the organic semiconductor composition of the present invention is not particularly limited, and known methods can be adopted. For example, by simultaneously or sequentially adding Component A and Component C, which is added if necessary, in a predetermined amount to the solvent containing Component B, and appropriately stirring the solution, a desired composition can be obtained.

The viscosity of the organic semiconductor composition of the present invention is not particularly limited. In view of further improving coating properties, the viscosity of the composition at 25° C. is preferably 1 to 100 mPa·s, more preferably 2 to 50 mPa·s, even more preferably 5 to 40 mPa·s, and particularly preferably 10 to 30 mPa·s.

The viscosity is preferably measured by the method based on JIS Z8803.

(Organic Semiconductor Film, Organic Semiconductor Element, and Method for Manufacturing these)

The organic semiconductor film of the present invention and the organic semiconductor element of the present invention are preferably manufactured using the organic semiconductor composition of the present invention.

The method for manufacturing the organic semiconductor film and the organic semiconductor element by using the organic semiconductor composition of the present invention is not particularly limited, and known methods can be adopted. Examples of the method include a method of manufacturing an organic semiconductor film by applying the composition onto a predetermined base material and performing a drying treatment for removing at least a portion of the solvent contained in Component B.

The method for applying the composition onto a base material is not particularly limited, and known methods can be adopted. Examples thereof include an ink jet printing method, a flexographic printing method, a bar coating method, a spin coating method, a knife coating method, a doctor blade method, and the like. Among these, an ink jet printing method and a flexographic printing method are preferable.

As the flexographic printing method, an aspect in which a photosensitive resin plate is used as a flexographic printing plate is suitably exemplified. By the aforementioned aspect, it is possible to easily form a pattern by printing the composition onto a substrate.

Particularly, the method for manufacturing an organic semiconductor film of the present invention and the method for manufacturing an organic semiconductor element of the present invention preferably includes an application step of applying the organic semiconductor composition of the present invention onto a substrate and a removing step of removing at least a portion of Component B from the applied organic semiconductor composition.

For the drying treatment in the removing step, optimal conditions are appropriately selected according to the type of the solvent containing components A and B used. Particularly, in view of further improving the mobility and the film uniformity of the obtained organic semiconductor and in view of excellent productivity, the heating temperature is preferably 30° C. to 100° C. and more preferably 40° C. to 80° C., and the heating time is preferably 10 to 300 minutes and more preferably 30 to 180 minutes.

The film thickness of the formed organic semiconductor film is not particularly limited. However, from the viewpoint of the mobility and the film uniformity of the obtained organic semiconductor, the film thickness of the organic semiconductor film is preferably 10 to 500 nm, and more preferably 30 to 200 nm.

The organic semiconductor film manufactured using the composition of the present invention can be suitably used in an organic semiconductor element, and can be particularly suitably used in an organic transistor (organic thin film transistor).

The organic semiconductor element is not particularly limited. However, the organic semiconductor element is preferably a semiconductor element having a plurality of terminals, more preferably an organic semiconductor element having 2 to 5 terminals, and even more preferably an organic semiconductor element having 2 or 3 terminals.

Furthermore, the organic semiconductor element is preferably an element which does not use a photoelectric function. In a case where the organic semiconductor element actively uses a photoelectric function, the organic substance is likely to deteriorate due to light.

Examples of a 2-terminal element include a rectifier diode, a constant voltage diode, a PIN diode, a Schottky barrier diode, a surge protection diode, a diac, a varistor, a tunnel diode, and the like.

Examples of a 3-terminal element include a bipolar transistor, a Darlington transistor, a field effect transistor, insulated gate bipolar transistor, a uni-junction transistor, a static induction transistor, a gate turn thyristor, a triac, a static induction thyristor, and the like.

Among these, a rectifier diode and transistors are preferable, and a field-effect transistor is more preferable.

Examples of the field-effect transistor preferably include an organic thin film transistor.

An aspect of the organic thin film transistor of the present invention will be described with reference to a drawing.

FIG. 1 is a schematic cross-sectional view of an aspect of the organic semiconductor element (organic thin film transistor (TFT)) of the present invention.

In FIG. 1, an organic thin film transistor 100 includes a substrate 10, a gate electrode 20 disposed on the substrate 10, a gate insulating film 30 covering the gate electrode 20, a source electrode 40 and a drain electrode 42 which contact a surface of the gate insulating film 30 that is on the side opposite to the gate electrode 20 side, an organic semiconductor film 50 covering a surface of the gate insulating film 30 between the source electrode 40 and the drain electrode 42, and a sealing layer 60 covering each member. The organic thin film transistor 100 is a bottom gate-bottom contact type organic thin film transistor.

In FIG. 1, the organic semiconductor film 50 corresponds to a film formed of the composition described above.

Hereinafter, the substrate, the gate electrode, the gate insulating film, the source electrode, the drain electrode, the organic semiconductor film, the sealing layer, and methods for forming each of these will be specifically described.

<Substrate>

The substrate plays a role of supporting the gate electrode, the source electrode, the drain electrode, and the like which will be described later.

The type of the substrate is not particularly limited, and examples thereof include a plastic substrate, a glass substrate, a ceramic substrate, and the like. Among these, from the viewpoint of applicability to each device and costs, a glass substrate or a plastic substrate is preferable.

Examples of materials of the plastic substrate include a thermosetting resin (for example, an epoxy resin, a phenol resin, a polyimide resin, or a polyester resin (for example, polyethylene terephthalate (PET) or polyethylene naphthalate (PEN)) and a thermoplastic resin (for example, a phenoxy resin, a polyethersulfone, polysulfone, or polyphenylene sulfone).

Examples of materials of the ceramic substrate include alumina, aluminum nitride, zirconia, silicon, silicon nitride, silicon carbide, and the like.

Examples of materials of the glass substrate include soda lime glass, potash glass, borosilicate glass, quartz glass, aluminosilicate glass, lead glass, and the like.

<Gate Electrode, Source Electrode, and Drain Electrode>

Examples of materials of the gate electrode, the source electrode, and the drain electrode include a metal such as gold (Au), silver, aluminum (Al), copper, chromium, nickel, cobalt, titanium, platinum, tantalum, magnesium, calcium, barium, or sodium; a conductive oxide such as $InO_2$, $SnO_2$, or indium tin oxide (ITO); a conductive polymer such as polyaniline, polypyrrole, polythiophene, polyacetylene, or polydiacetylene; a semiconductor such as silicon, germanium, or gallium arsenide; a carbon material such as fullerene, carbon nanotubes, or graphite; and the like. Among these, a metal is preferable, and silver and aluminum are more preferable.

The thickness of each of the gate electrode, the source electrode, and the drain electrode is not particularly limited, but is preferably 20 to 200 nm.

The method for forming the gate electrode, the source electrode, and the drain electrode is not particularly limited, but examples thereof include a method of vacuum vapor-depositing or sputtering an electrode material onto a substrate, a method of coating a substrate with a composition for forming an electrode, a method of printing a composition for forming an electrode onto a substrate, and the like. In a case where the electrode is patterned, examples of the patterning method include a photolithography method; a printing method such as ink jet printing, screen printing, offset printing, or relief printing a mask vapor deposition method; and the like.

<Gate Insulating Film>

Examples of materials of the gate insulating film include a polymer such as polymethyl methacrylate, polystyrene, polyvinylphenol, polyimide, polycarbonate, polyester, polyvinylalcohol, polyvinyl acetate, polyurethane, polysulfone, polybenzoxazole, polysilsesquioxane, an epoxy resin, or a phenol resin; an oxide such as silicon dioxide, aluminum oxide, or titanium oxide; a nitride such as silicon nitride; and the like. Among these materials, in view of the compatibility with the organic semiconductor film, a polymer is preferable.

In a case where a polymer is used as the material of the gate insulating film, it is preferable to use a cross-linking agent (for example, melamine) in combination. If the cross-linking agent is used in combination, the polymer is cross-linked, and hence the durability of the formed gate insulating film is improved.

The film thickness of the gate insulating film is not particularly limited, but is preferably 100 to 1,000 nm.

The method for forming the gate insulating film is not particularly limited, but examples thereof include a method of coating a substrate, on which the gate electrode is formed, with a composition for forming a gate insulating film, a method of vapor-depositing or sputtering the material of the gate insulating film onto a substrate on which the gate electrode is formed, and the like. A method for coating the aforementioned substrate with the composition for forming a gate insulating film is not particularly limited, and it is possible to use a known method (a bar coating method, a spin coating method, a knife coating method, or a doctor blade method).

In a case where the gate insulating film is formed by coating the substrate with the composition for forming a gate insulating film, for the purpose of removing the solvent, causing cross-linking, or the like, the composition may be heated (baked) after coating.

<Organic Semiconductor Film>

The organic semiconductor film of the present invention is a film formed of the organic semiconductor composition of the present invention.

The method for forming the organic semiconductor film is not particularly limited. By applying the aforementioned composition onto the source electrode, the drain electrode, and the gate insulating film and, if necessary, performing a drying treatment, a desired organic semiconductor film can be formed.

<Sealing Layer>

From the viewpoint of durability, the organic semiconductor element of the present invention preferably includes a sealing layer as an outermost layer. In the sealing layer, a known sealant can be used.

The thickness of the sealing layer is not particularly limited, but is preferably 0.2 to 10 μm.

The method for forming the sealing layer is not particularly limited, but examples thereof include a method of coating a substrate, on which the gate electrode, the gate insulating film, the source electrode, the drain electrode, and the organic semiconductor film are formed, with a composition for forming a sealing layer, and the like. Specific examples of the method of coating the substrate with the composition for forming a sealing layer are the same as the examples of the method of coating the substrate with the composition for forming a gate insulating film. In a case where the organic semiconductor film is formed by coating the substrate with the composition for forming a sealing layer, for the purpose of removing the solvent, causing cross-linking, or the like, the composition may be heated (baked) after coating.

Figure 2:
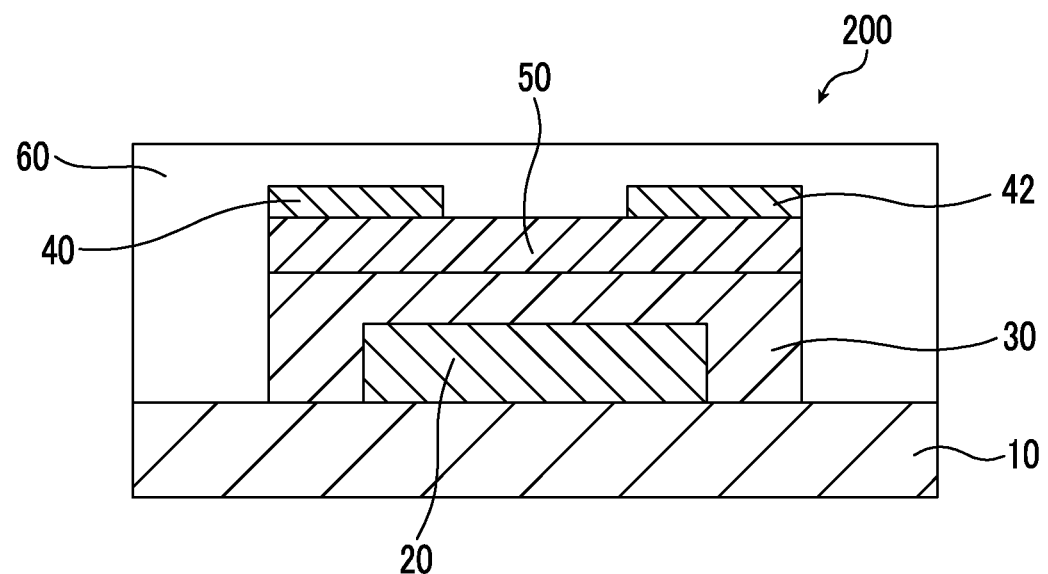
FIG. 2 is a schematic cross-sectional view of another aspect of the organic semiconductor element of the present invention.

FIG. 2 is a schematic cross-sectional view of another aspect of the organic semiconductor element (organic thin film transistor) of the present invention.

In FIG. 2, an organic thin film transistor 200 includes the substrate 10, the gate electrode 20 disposed on the substrate 10, the gate insulating film 30 covering the gate electrode 20, the organic semiconductor film 50 disposed on the gate insulating film 30, the source electrode 40 and the drain electrode 42 disposed on the organic semiconductor film 50, and the sealing layer 60 covering each member. Herein, the source electrode 40 and the drain electrode 42 are formed using the aforementioned composition of the present invention. The organic thin film transistor 200 is a bottom gate-top contact type organic thin film transistor.

The substrate, the gate electrode, the gate insulating film, the source electrode, the drain electrode, the organic semiconductor film, and the sealing layer are as described above.

In FIGS. 1 and 2, the aspects of the bottom gate-bottom contact type organic thin film transistor and the bottom gate-top contact type organic thin film transistor were specifically described. However, the organic semiconductor composition of the present invention can also be applied to a top gate-bottom contact type organic thin film transistor and a top gate-top contact type organic thin film transistor.

The aforementioned organic thin film transistor can be suitably used in electronic paper, a display device, and the like.

EXAMPLES

Hereinafter, the present invention will be more specifically described based on examples. The materials and the amount thereof used, the proportion of the materials, the content and procedure of treatments, and the like described in the following examples can be appropriately changed within a scope that does not depart from the gist of the present invention. Accordingly, the scope of the present invention is not limited to the following specific examples. Herein, unless otherwise specified, "part" and "%" are based on mass.

Examples 1 to 26 and Comparative Examples 1 to 6

—Preparation of Organic Semiconductor Composition—

The organic semiconductor (Component A) shown in Table 1 which will be described later, the organic solvent (Component B) shown in Table 1, and the polymer compound (Component C) shown in Table 1 were weight and moved into a glass vial at a predetermined ratio (mass ratio with respect to the total mass of the composition) shown in Table 1, and stirred and mixed together for 10 minutes by using MIX ROTOR (manufactured by AS ONE Corporation). The mixture was filtered through a 0.5 µm membrane filter, thereby obtaining an organic semiconductor composition.

—Manufacturing of Organic Transistor—

A bottom gate-bottom contact type organic transistor was formed in the following manner.

<Formation of Gate Electrode>

Silver nano-ink (H-1, manufactured by Mitsubishi Materials Corporation) was printed on an alkaline-free glass substrate (5 cm×5 cm) by means of ink jet printing using an ink jet recording device DMP 2831 (with a 1 µL head, manufactured by FUJIFILM Graphic Systems), thereby forming a wiring pattern having a width of 100 µm and a film thickness of 100 nm. Then, the substrate was fired on a hot plate at 200° C. for 90 minutes in the atmosphere, thereby forming gate electrode wiring.

<Formation of Gate Insulating Film>

Five parts by mass of polyvinyl phenol (Mw: 25,000, manufactured by Sigma-Aldrich Co. LLC.), 5 parts by mass of melamine, and 90 parts by mass of polyethylene glycol monomethyl ether acetate were stirred and mixed together and then filtered through a 0.2 µm membrane filter, thereby preparing a solution. The glass substrate on which the gate electrode was formed was spin-coated (1,000 rpm, 120 seconds) with the obtained solution by adding the solution dropwise onto the substrate, and then heated to 150° C. for 30 minutes, thereby forming a gate insulating film having a film thickness of 500 nm.

<Formation of Source Electrode and Drain Electrode>

A metal mask having a plurality of patterns was placed at the center of the substrate coated with the insulating film, and the substrate was irradiated with UV ozone for 30 minutes such that the opening portions of the mask were modified into a hydrophilic treated surface. Herein, the metal mask had mask portions which block light and opening portions. In the vicinity of the modified portions, by means of ink jet printing using DMP 2831 (with a 1 pL head), patterns of a source electrode and a drain electrode having a channel length of 50 µm and a channel width of 320 µm were formed. The obtained substrate was fired on a hot plate at 200° C. for 90 minutes in a $N_2$ atmosphere (in a glove box, an environment with an oxygen concentration of equal to or lower than 20 ppm), thereby forming a source electrode and a drain electrode having a film thickness of 200 nm.

<Formation of Organic Semiconductor Film: Flexographic Printing Method>

The substrate on which the source and drain electrodes were formed was coated with the composition (composition in Table 1) prepared as above by a flexographic printing method. As a printing device, a flexographic printability tester F1 (manufactured by IGT Testing Systems K.K.) was used, and as a flexographic resin plate, AFP DSH 1.70% (manufactured by Asahi Kasei Corporation.)/solid image was used. Printing was performed at a transport rate of 0.3 m/sec with applying a pressure of 60 N between the plate and the substrate, and then the substrate was dried as it was for 2 hours at 60° C., thereby preparing an organic semiconductor film (film thickness: 100 nm) between the source electrode and the drain electrode. In this way, an organic transistor was manufactured.

<Formation of Organic Semiconductor Film: Ink Jet Printing Method>

The substrate on which the source and drain electrodes were formed was coated with the composition (composition in Table 1) prepared as above by an ink jet method. By using DMP 2831 (manufactured by FUJIFILM Graphic Systems) as an ink jet device and a 10 pL head, a solid film was formed at a jetting frequency of 5 Hz and a dot pitch (distance between dots (ink droplets) in ink jet printing) of 20 µm. The substrate was dried as it was for 2 hours at 60° C., thereby preparing an organic semiconductor film between the source electrode and the drain electrode.

The obtained organic transistors of examples were tested regarding the variation in mobility. As a result, it was understood that the organic transistors are highly reliable devices that exhibit excellent mobility characteristics with a small variation. In contrast, the organic transistors of comparative examples were poorly reliable devices with a big variation.

—Evaluation—

<Film Uniformity>

Within the organic semiconductor film, which was obtained as above by applying the organic semiconductor composition by means of ink jet printing or flexographic printing and drying the composition, 3 sites were randomly selected and the film thickness thereof was measured using a film thickness measuring instrument (DEKTAK, manufactured by Bruker). Regarding the obtained film thicknesses of the three sites, the variation was evaluated. As a method for calculating the variation, the arithmetic mean of the obtained film thicknesses of the three sites was determined and denoted by an average X, a "difference" between the average X and the value of a film thickness of each sample was then calculated, an average Y of an absolute value of the "difference" was calculated, and the variation was determined by (average Y/average X)×100.

The evaluation standards are as below. For practical use, the organic semiconductor films evaluated to be AA to B are preferable.

AA: the variation in the film thickness was less than 10%.

A: the variation in the film thickness was equal to or greater than 10% and less than 20%.

B: the variation in the film thickness was equal to or greater than 20% and less than 30%.

C: the variation in the film thickness was equal to or greater than 30%.

<Mobility>

Within the organic semiconductor film, which was obtained as above by applying the organic semiconductor composition by means of ink jet printing or flexographic printing and drying the composition, the carrier mobility of 5 sites was measured using a semiconductor measuring device B2900A (manufactured by Agilent's Electronic Measurement Group), and the average mobility thereof was calculated. The mobility was measured under the following conditions.

Between the source electrode and the drain electrode of each organic TFT element, a voltage of −60 V was applied, and the gate voltage was varied within a range of +10 V to −60 V. In this way, a carrier mobility μ was calculated using the following equation showing a drain current $I_d$.

$$I_d = (w/2L)\mu C_i(V_g - V_{th})^2$$

In the equation, L represents a gate length, W represents a gate width, $C_i$ represents a capacity of the insulating layer per unit area, $V_g$ represents a gate voltage, and $V_{th}$ represents a threshold voltage.

In the present evaluation, the organic semiconductor film was formed such that L became 100 μm and W became 1 mm. The evaluation standards are as below. The higher the mobility, the better.

S: the average mobility was equal to or higher than 0.2 cm²/V·s.

AA: the average mobility was equal to or higher than 0.1 cm²/V·s and less than 0.2 cm²N/Vs.

A: the average mobility was equal to or higher than 0.05 cm²/V·s and less than 0.1 cm²N/V·s B: the average mobility was equal to or higher than 0.02 cm²/V·s and less than 0.05 cm²/V·s.

C: the average mobility was less than 0.02 cm²/V·s.

<Heat Resistance>

The organic transistors prepared as above were stored for 2 hours in a constant-temperature tank with a temperature of 85° C. in the atmosphere, and then the mobility after storage was measured. The mobility of each sample measured before storage was expressed as "1", a relative value of the mobility after storage was calculated, and the heat resistance was evaluated based on the following standards. The results are shown in Table 1.

In the present invention, in the evaluation of heat resistance, "A" and "B" are pass levels. For practical use, the organic transistors evaluated to be "A" are preferable. The organic transistors evaluated to be "C" have poor heat resistance and do not reach the pass level in the present invention.

A: the relative value was equal to or greater than 0.7.

B: the relative value was equal to or greater than 0.4 and less than 0.7.

C: the relative value was less than 0.4

The evaluation results are summarized in Table 1.

TABLE 1

| | Printing method | Component A (% by mass) | Thin film of Component A Ip (eV) | Component B (% by mass) | Melting point of Component B (°C) | Boiling point of Component B (°C) | Component C (% by mass) | Film uniformity | Mobility | Heat resistance |
|---|---|---|---|---|---|---|---|---|---|---|
| Example 1 | FL | OSC-15 (0.8) | ≥5.1 | (1) (98.4) | ≤25 | 160-170 | Polystyrene (0.8) | AA | AA | A |
| Example 2 | FL | OSC-15 (0.8) | ≥5.1 | (2) (98.4) | ≤25 | 210-220 | Polystyrene (0.8) | AA | S | A |
| Example 3 | FL | OSC-15 (0.8) | ≥5.1 | (2) (98.9) | ≤25 | 210-220 | Polystyrene (0.3) | AA | S | A |
| Example 4 | FL | OSC-15 (0.8) | ≥5.1 | (2) (99.0) | ≤25 | 210-220 | Polystyrene (0.2) | A | AA | A |
| Example 5 | FL | OSC-15 (0.8) | ≥5.1 | (2) (98.0) | ≤25 | 210-220 | Polystyrene (1.2) | AA | AA | A |
| Example 6 | FL | OSC-15 (0.8) | ≥5.1 | (2) (97.9) | ≤25 | 210-220 | Polystyrene (1.3) | AA | A | A |
| Example 7 | FL | OSC-15 (0.8) | ≥5.1 | (2) (97.2) | ≤25 | 210-220 | Poly(α-methylstyrene) (2.0) | AA | A | A |
| Example 8 | IJ | OSC-15 (0.8) | ≥5.1 | (2) (99.1) | ≤25 | 210-220 | Poly(α-methylstyrene) (0.1) | AA | S | A |
| Example 9 | IJ | OSC-15 (0.8) | ≥5.1 | (2) (99.2) | ≤25 | 210-220 | — | A | S | A |
| Example 10 | IJ | OSC-15 (0.4) | ≥5.1 | (2) (99.6) | ≤25 | 210-220 | — | A | A | A |
| Example 11 | FL | OSC-15 (0.8) | ≥5.1 | (3) (98.4) | ≤25 | 220-230 | Polystyrene (0.8) | AA | AA | A |
| Example 12 | FL | OSC-15 (0.8) | ≥5.1 | (4) (98.4) | ≤25 | 180-190 | Polystyrene (0.8) | AA | AA | A |
| Example 13 | FL | OSC-15 (0.8) | ≥5.1 | (5) (98.4) | ≤25 | 180-190 | Polystyrene (0.8) | AA | AA | A |
| Example 14 | FL | OSC-15 (0.8) | ≥5.1 | (6) (98.4) | ≤25 | 190-200 | Polystyrene (0.8) | AA | A | A |
| Example 15 | FL | OSC-15 (0.8) | ≥5.1 | (7) (98.4) | ≤25 | 220-230 | Polystyrene (0.8) | AA | A | A |
| Example 16 | FL | OSC-15 (0.8) | ≥5.1 | (8) (98.4) | ≤25 | 240-250 | Polystyrene (0.8) | AA | A | A |
| Example 17 | FL | OSC-15 (0.8) | ≥5.1 | (9) (98.4) | ≤25 | 220-230 | Polystyrene (0.8) | A | A | A |
| Example 18 | FL | OSC-15 (0.8) | ≥5.1 | (10) (98.4) | ≤25 | 190-200 | Polystyrene (0.8) | AA | A | A |
| Example 19 | FL | OSC-15 (0.8) | ≥5.1 | (11) (98.4) | ≤25 | 220-230 | Polystyrene (0.8) | AA | A | A |
| Example 20 | FL | OSC-15 (0.8) | ≥5.1 | (12) (98.4) | ≤25 | 235-245 | Polystyrene (0.8) | A | B | A |
| Example 21 | FL | OSC-15 (0.8) | ≥5.1 | (13) (98.4) | ≤25 | 230-240 | Polystyrene (0.8) | A | B | A |
| Example 22 | FL | OSC-15 (0.8) | ≥5.1 | (14) (98.4) | ≤25 | 220-230 | Polystyrene (0.8) | A | A | A |
| Example 23 | FL | OSC-15 (0.8) | ≥5.1 | (15) (98.4) | ≤25 | 220-230 | Polystyrene (0.8) | A | B | A |
| Example 24 | FL | OSC-17 (0.8) | ≥5.1 | (2) (98.4) | ≤25 | 210-220 | Polystyrene (0.8) | AA | S | A |
| Example 25 | FL | OSC-19 (1.2) | ≥5.1 | (2) (98.0) | ≤25 | 210-220 | Polystyrene (0.8) | A | A | B |
| Example 26 | FL | OSC-7 (0.6) | ≥5.1 | (2) (98.6) | ≤25 | 210-220 | Polystyrene (0.8) | A | AA | A |
| Comparative Example 1 | FL | OSC-15 (0.8) | ≥5.1 | Anisole (98.4) | ≤25 | 150-160 | Polystyrene (0.8) | C | C | C |
| Comparative Example 2 | FL | OSC-15 (0.8) | ≥5.1 | Tetralin (98.4) | ≤25 | 200-210 | Polystyrene (0.8) | C | C | C |
| Comparative Example 3 | FL | OSC-15 (0.8) | ≥5.1 | O-Dichlorobenzene (98.4) | ≤25 | 175-185 | Polystyrene (0.8) | B | C | C |
| Comparative Example 4 | FL | OSC-15 (0.8) | ≥5.1 | 3-chlorothiophene (98.4) | ≤25 | 130-140 | Polystyrene (0.8) | C | B | C |
| Comparative Example 5 | FL | OSC-15 (0.8) | ≥5.1 | 2,3-benzofuran (98.4) | ≤25 | 170-180 | Polystyrene (0.8) | B | B | C |
| Comparative Example 6 | IJ | P3HT (0.8) | <5.1 | (2) (99.2) | ≤25 | 210-220 | — | A | B | C |

In Table 1, IJ means that the organic semiconductor film was formed by ink jet printing, and FL means that the organic semiconductor film was formed by flexographic printing.

Furthermore, in Table 1, the mark "-" means that the film does not contain the corresponding component.

The materials used in Table 1 are as below.

(Component A)

*Organic semiconductor A: OSC-15 (following structure), synthetic product, synthesized according to the method described in JP2009-190999A.

OSC-15

Organic semiconductor B: OSC-17 (following structure), synthetic product, synthesized according to the method described in JP2012-209329A.

OSC-17

Organic semiconductor C: OSC-19 (following structure), synthetic product, synthesized according to the method described in J. Am. Chem. Soc., 2008, 130, 2706-2707.

Et in the following structure represents an ethyl group.

OSC-19

Organic semiconductor D: OSC-7 (following structure), synthetic product, synthesized according to the method described in US2008/0142792A.

OSC-7

P3HT: poly(3-hexylthiophene-2,5-diyl): number-average molecular weight of 15,000 to 45,000, manufactured by Sigma-Aldrich Co. LLC.

(Component B)

(1), (10), and (11): the following compounds, manufactured by Sigma-Aldrich Co. LLC.

(2): the following compound, manufactured by Wako Pure Chemical Industries, Ltd.

(3), (4), (5), (6), (7), (8), (9), (12), (13), (14), and (15): the following compounds, manufactured by TOKYO CHEMICAL INDUSTRY CO., LTD.

(1)

(2)

(3)

(4)

(5)

-continued (6) 

(7) 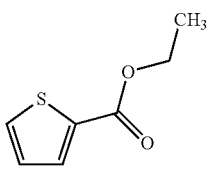

(8) 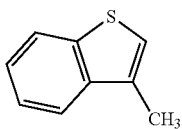

(9) 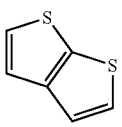

(10) 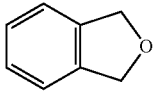

(11) 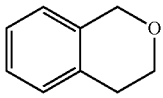

(12) 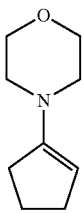

(13) 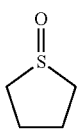

(14) 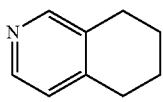

(15) 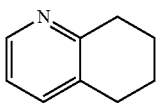

Anisole (manufactured by Sigma-Aldrich Co. LLC.)
Tetralin (manufactured by Sigma-Aldrich Co. LLC.)
o-Dichlorobenzene (manufactured by Sigma-Aldrich Co. LLC.)
3-Chlorothiophene (manufactured by TOKYO CHEMICAL INDUSTRY CO., LTD.)
2,3-Benzofuran (manufactured by TOKYO CHEMICAL INDUSTRY CO., LTD.)
(Component C)
Poly(α-methylstyrene): number-average molecular weight of 300,000 to 400,000, manufactured by Sigma-Aldrich Co. LLC.
Polystyrene: number-average molecular weight of 2,000,000, manufactured by Tosoh Corporation The ionization potential of the organic semiconductors of present Examples 1 to 26 and Comparative Examples 1 to 6 was measured as below.

A solution obtained by mixing an organic semiconductor (0.4% by mass) with a solvent (99.6% by mass) was formed into a film on a glass substrate by a drop casting method and then dried for 2 hours at 60° C. By using AC-2 manufactured by RIKEN KIKAI Co., Ltd., the ionization potential of each of the obtained organic thin films was measured.

EXPLANATION OF REFERENCES

10: substrate
20: gate electrode
30: gate insulating film
40: source electrode
42: drain electrode
50: organic semiconductor film
60: sealing layer
100, 200: organic thin film transistor

What is claimed is:
1. An organic semiconductor composition comprising:
an organic semiconductor as Component A; and
an organic solvent, which is represented by Formula B-1 and has a melting point of equal to or lower than 25° C. and a boiling point of equal to or higher than 150° C. and equal to or lower than 280° C., as Component B,
wherein an ionization potential of Component A is equal to or higher than 5.1 eV,

(B-1)

in Formula B-1, X represents O, S, S=O, O=S=O, or NR; $Y_1$ to $Y_4$ each independently represent $NR_1$ or $CR_{10}R_{11}$; R, $R_1$, $R_{10}$, and $R_{11}$ each independently represent a hydrogen atom or a substituent; n represents 1 or 2; in a case where n is 2, two $Y_4$'s may be the same as or different from each other; in a case where X is NR, a substituent on $Y_1$ or $Y_4$ and the substituent R on N may form a ring or may form a double bond in a 5-membered or 6-membered ring containing X by being bonded to each other; substituents of $Y_1$ to $Y_4$ adjacent to each other may form a ring or may form a double bond in a 5-membered or 6-membered ring containing X by being bonded to each other; and in a case where X is O, a substituent of $Y_1$ and a substituent of $Y_2$ do not form a double bond by being bonded to each other.

2. The organic semiconductor composition according to claim 1,
wherein Component B is an organic solvent which is represented by the following Formula B-2 and has a melting point of equal to or lower than 25° C. and a boiling point of equal to or higher than 150° C. and equal to or lower than 280° C.,

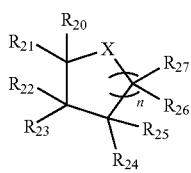
(B-2)

in Formula B-2, X represents O, S, S=O, O=S=O, or NR; n represents 1 or 2; R and $R_{20}$ to $R_{27}$ each independently represent a hydrogen atom or a substituent; in a case where n is 2, two $R_{26}$'s and two $R_{27}$'s may be the same as or different from each other; two out of R and $R_{20}$ to $R_{27}$ may form a ring by being bonded to each other; R and $R_{20}$, $R_{20}$ and R2, R2 and $R_{24}$, and $R_{24}$ and $R_{26}$ may form a double bond in a 5-membered or 6-membered ring containing X by being bonded to each other; and in a case where X is O, $R_{20}$ and $R_{22}$ do not form a double bond by being bonded to each other.

3. The organic semiconductor composition according to claim 1,
wherein Component B is an organic solvent which is represented by any one of the following Formulae B-3 to B-6 and has a melting point of equal to or lower than 25° C. and a boiling point of equal to or higher than 150° C. and equal to or lower than 280° C.,

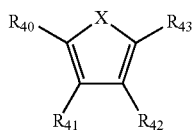
(B-3)

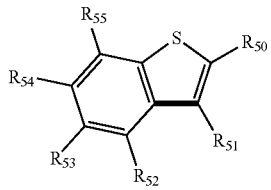
(B-4)

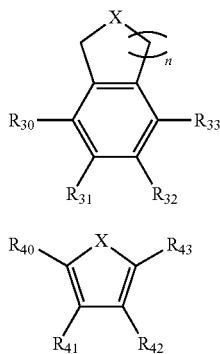
(B-5)

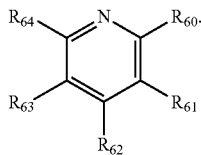
(B-6)

in Formulae B-3 to B-6, X represents an oxygen atom or a sulfur atom; n represents 1 or 2; $R_{30}$ to $R_{33}$, $R_{40}$ to $R_{43}$, $R_{50}$ to $R_{55}$, and R to $R_{64}$ each independently represent a hydrogen atom or a substituent; at least one of $R_{40}$, $R_{41}$, $R_{42}$, or $R_{43}$ represents a halogen atom; and $R_{60}$ and $R_{61}$ and $R_{61}$ and $R_{62}$ may form a ring by being linked to each other.

4. The organic semiconductor composition according to claim 1,
wherein Component A has a condensed polycyclic aromatic group,
the number of rings in the condensed polycyclic aromatic group is equal to or greater than 4,
at least one ring in the condensed polycyclic aromatic group is a heterocyclic ring, and
at least one structure selected from the group consisting of a benzene ring, a naphthalene ring, and a phenanthrene ring is contained as a partial structure in the condensed polycyclic aromatic group.

5. The organic semiconductor composition according to claim 4,
wherein the number of rings in the condensed polycyclic aromatic group is 5 or 6.

6. The organic semiconductor composition according to claim 1,
wherein Component A contains at least one kind of compound represented by any one of Formulae 1 to 16,

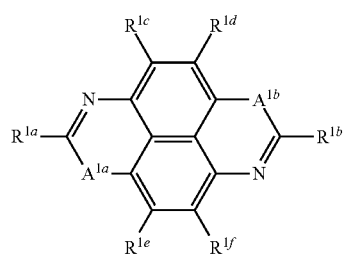
(1)

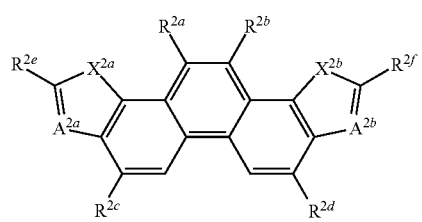
(2)

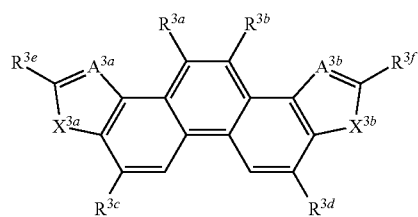
(3)

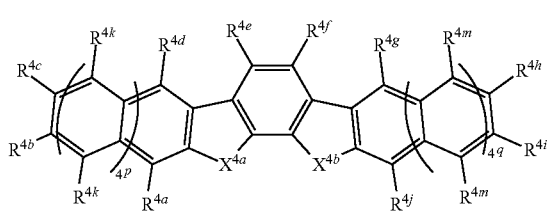
(4)

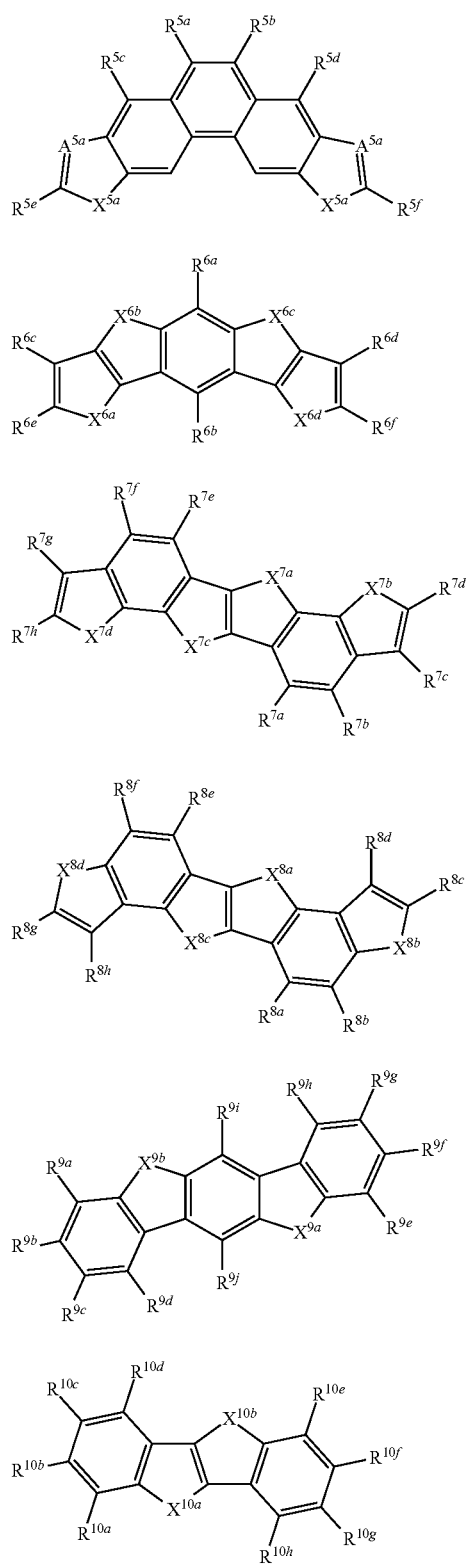
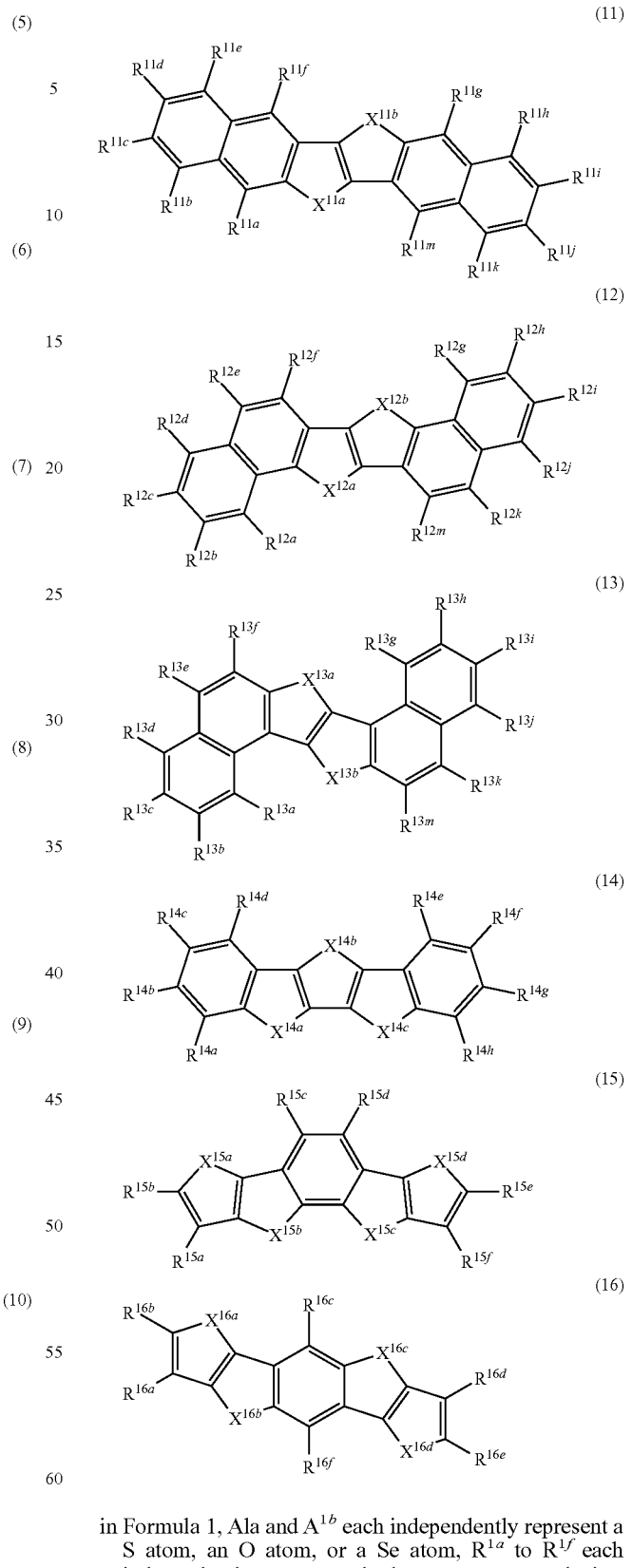
in Formula 1, A1a and A$^{1b}$ each independently represent a S atom, an O atom, or a Se atom, R$^{1a}$ to R$^{1f}$ each independently represent a hydrogen atom or a substituent, and at least one of R$^{1a}$, R$^{1b}$, R$^{1c}$, R$^{1d}$, R$^{1e}$, or R$^{1f}$ is a group represented by the following Formula W,
-L$^W$-R$^W$                     (W)

in Formula W, $L^W$ represents a divalent linking group represented by any one of the following Formulae L-1 to L-25 or a divalent linking group in which 2 or more divalent linking groups represented by any one of the following Formulae L-1 to L-25 are bonded to each other, and $R^W$ represents an alkyl group, a cyano group, a vinyl group, an ethynyl group, an oxyethylene group, an oligo-oxyethylene group in which a repetition number v of an oxyethylene unit is equal to or greater than 2, a siloxane group, an oligosiloxane group having 2 or more silicon atoms, or a trialkylsilyl group,

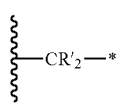
(L-1)

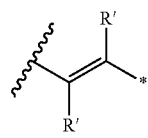
(L-2)

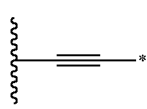
(L-3)

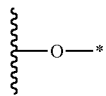
(L-4)

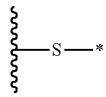
(L-5)

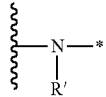
(L-6)

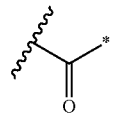
(L-7)

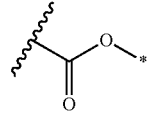
(L-8)

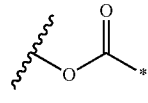
(L-9)

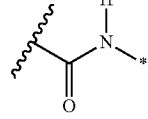
(L-10)

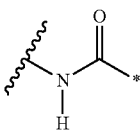
(L-11)

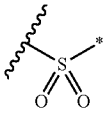
(L-12)

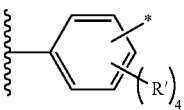
(L-13)

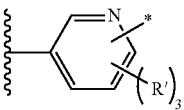
(L-14)

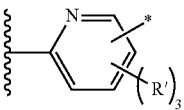
(L-15)

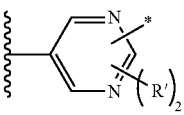
(L-16)

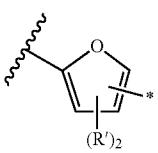
(L-17)

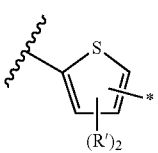
(L-18)

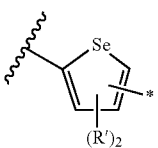
(L-19)

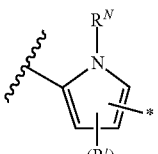
(L-20)

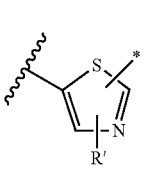
(L-21)

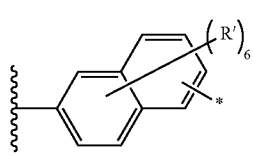
(L-22)

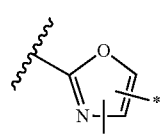
(L-23)

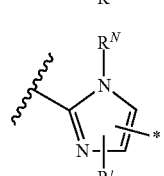
(L-24)

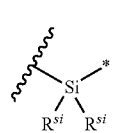
(L-25)

in Formulae L-1 to L-25, * represents a bonding position with respect to $R^W$, the portion of a wavy line represents a bonding position on the other side, R' in Formulae L-1, L-2, L-6, and L-13 to L-24 each independently represents a hydrogen atom or a substituent, $R^N$ in Formulae L-20 and L-24 represents a hydrogen atom or a substituent, and $R^{si}$ in Formula L-25 each independently represents a hydrogen atom, an alkyl group, an alkenyl group, or an alkynyl group, in Formula 2, $X^{2a}$ and $X^{2b}$ each independently represent $NR^{2i}$, an O atom, or a S atom, $A^{2a}$ represents $CR^{2g}$ or a N atom, $A^{2b}$ represents $CR^{2h}$ or a N atom, $R^{2i}$ represents a hydrogen atom, an alkyl group, an alkenyl group, an alkynyl group, or an acyl group, $R^{2a}$ to $R^{2h}$ each independently represent a hydrogen atom or a substituent, and at least one of $R^{2a}$, $R^{2b}$, $R^{2c}$, $R^{2d}$, $R^{2e}$, $R^{2f}$, $R^{2g}$, or $R^{2h}$ is a group represented by Formula W, in Formula 3, $X^{3a}$ and $X^{3b}$ each independently represent a S atom, an O atom, or $NR^{3g}$, and $A^{3a}$ and $A^{3b}$ each independently represent $CR^{3h}$ or a N atom, $R^{3a}$ to $R^{3h}$ each independently represent a hydrogen atom or a substituent, and at least one of $R^{3a}$, $R^{3b}$, $R^{3c}$, $R^{3d}$, $R^{3e}$, $R^{3f}$, $R^{3g}$, or $R^{3h}$ is a group represented by Formula W, in Formula 4, $X^{4a}$ and $X^{4b}$ each independently represent an O atom, a S atom, or a Se atom, 4p and 4q each independently represent an integer of 0 to 2, $R^{4a}$ to $R^{4j}$, $R^{4k}$, and $R^{4m}$ each independently represent a hydrogen atom, a halogen atom, or a group represented by Formula W, and at least one of $R^{4a}$, $R^{4b}$, $R^{4c}$, $R^{4d}$, $R^{4e}$, $R^{4f}$, $R^{4g}$, $R^{4h}$, $R^{4i}$, $R^{4j}$, $R^{4k}$, or $R^{4m}$ is a group represented by Formula W, and in a case where at least one of $R^{4e}$ or $R^{4f}$ is a group represented by Formula W, $L^W$ in Formula W represented by $R^{4e}$ and $R^{4f}$ is a divalent linking group represented by Formula L-2 or L-3, in Formula 5, $X^{5a}$ and $X^{5b}$ each independently represent $NR^{5i}$, an O atom, or a S atom, $A^{5a}$ represents $CR^{5g}$ or a N atom, $A^{5b}$ represents $CR^{5h}$ or a N atom, $R^{5i}$ represents a hydrogen atom, an alkyl group, an alkenyl group, an alkynyl group, an acyl group, an aryl group, or a heteroaryl group, $R^{5a}$ to $R^{5h}$ each independently represent a hydrogen atom or a substituent, and at least one of $R^{5a}$, $R^{5b}$, $R^{5c}$, $R^{5d}$, $R^{5e}$, $5^{5f}$, $R^{5g}$, or $R^{5h}$ is a group represented by Formula W, in Formula 6, $X^{6a}$ to $X^{6d}$ each independently represent $NR^{6g}$, an O atom, or a S atom, $R^{6g}$ represents a hydrogen atom, an alkyl group, an alkenyl group, an alkynyl group, an acyl group, an aryl group, or a heteroaryl group, $R^{6a}$ to $R^{6f}$ each independently represent a hydrogen atom or a substituent, and at least one of $R^{6a}$, $R^{6b}$, $R^{6c}$, $R^{6d}$, $R^{6e}$, or $R^{6f}$ is a group represented by Formula W, in Formula 7, $X^{7a}$ and $X^{7c}$ each independently represent a S atom, an O atom, a Se atom, or $NR^{7i}$, $X^{7b}$ and $X^{7d}$ each independently represent a S atom, an O atom, or a Se atom, $R^{7a}$ to $R^{7i}$ each independently represent a hydrogen atom or a substituent, and at least one of $R^{7a}$, $R^{7b}$, $R^{7c}$, $R^{7d}$, $R^{7e}$, $R^{7f}$, $R^{7g}$, $R^{7h}$, or $R^{7i}$ is a group represented by Formula W, in Formula 8, $X^{8a}$ and $X^{8c}$ each independently represent a S atom, an O atom, a Se atom, or $NR^{8i}$, $X^{8b}$ and $X^{8c}$ each independently represent a S atom, an O atom, or a Se atom, $R^{8a}$ to $R^{8i}$ each independently represent a hydrogen atom or a substituent, and at least one of $R^{8a}$, $R^{8b}$, $R^{8c}$, $R^{8d}$, $R^{8e}$, $R^{8f}$, $R^{8g}$, $R^{8h}$, or $R^{8i}$ is a group represented by Formula W, in Formula 9, $X^{9a}$ and $X^{9b}$ each independently represent an O atom, a S atom, or a Se atom, $R^{9c}$, $R^{9d}$, and $R^{9g}$ to $R^{9j}$ each independently represent a hydrogen atom, a halogen atom, or a group represented by Formula W, and $R^{9a}$, $R^{9b}$, $R^{9e}$, and $R^{9f}$ each independently represent a hydrogen atom or a substituent, in Formula 10, $R^{10a}$ to $R^{10h}$ each independently represent a hydrogen atom or a substituent, at least one of $R^{10a}$, $R^{10b}$, $R^{10c}$, $R^{10d}$, $R^{10e}$, $R^{10f}$, $R^{10g}$, or $R^{10h}$ represents a substituent represented by Formula W, $X^{10a}$ and $X^{10b}$ each independently represent a S atom, an O atom, a Se atom, or $NR^{10i}$, and $R^{10i}$ each independently represents a hydrogen atom or a group represented by Formula W, in Formula 11, $X^{11a}$ and $X^{11b}$ each independently represent a S atom, an O atom, a Se atom, or $NR^{11n}$, $R^{11a}$ to $R^{11k}$, $R^{11m}$, and $R^{11n}$ each independently represent a hydrogen atom or a substituent, and at least one of $R^{11a}$, $R^{11b}$, $R^{11c}$, $R^{11d}$, $R^{11e}$, $R^{11f}$, $R^{11g}$, $R^{11h}$, $R^{11i}$, $R^{11j}$, $R^{11k}$, $R^{11m}$, or $R^{11n}$ is a group represented by Formula W, in Formula 12, $X^{12a}$ and $X^{12b}$ each independently represent a S atom, an O atom, a Se atom, or $NR^{12n}$, $R^{12a}$ to $R^{12k}$, $R^{12m}$, and $R^{12n}$ each independently represent a hydrogen atom or a substituent, and at least one of $R^{12a}$, $R^{12b}$, $R^{12c}$, $R^{12d}$, $R^{12e}$, $R^{12f}$, $R^{12g}$, $R^{12h}$, $R^{12i}$, $R^{12j}$, $R^{12k}$, $R^{12m}$, or $R^{12n}$ is a group represented by Formula W, in Formula 13, $X^{13a}$ and $X^{13b}$ each independently represent a S atom, an O atom, a Se atom, or $NR^{13n}$, $R^{13a}$ to $R^{13k}$, $R^{13m}$, and $R^{13n}$ each independently represent a hydrogen atom or a substituent, and at least one of $R^{13a}$, $R^{13b}$, $R^{13c}$, $R^{13d}$, $R^{13e}$, $R^{13f}$, $R^{13g}$, $R^{13h}$, $R^{13i}$, $R^{13j}$, $R^{13k}$, $R^{13m}$, or $R^{13n}$ is a group represented by Formula W, in Formula 14, $X^{14a}$ to $X^{14c}$ each independently represent a S atom, an O atom, a Se atom, or $NR^{14i}$, $R^{14a}$ to $R^{14i}$ each independently represent a hydrogen atom or a substituent, and at least one of $R^{14a}$, $R^{14b}$, $R^{14c}$, $R^{14d}$, $R^{14e}$, $R^{14f}$, $R^{14g}$, $R^{14h}$, or $R^{14i}$ is a group represented by Formula W, in Formula 15, $X^{15a}$ to $X^{15d}$ each independently represent a S atom, an O atom, a Se atom, or $N^{15g}$, $R^{15a}$ to $R^{15g}$ each independently represent a hydrogen atom or a substituent, and at least one of $R^{15a}$, $R^{15b}$, $R^{15c}$, $R^{15d}$, $R^{15e}$, $R^{15f}$, or $R^{15g}$ is a group represented by Formula W, and in Formula 16, $X^{16a}$ to $X^{16d}$ each independently represent a S atom, an O atom, a Se atom, or $NR^{16g}$, $R^{16a}$ to $R^{16g}$ each independently represent a hydrogen atom or a substituent, and at least one of $R^{16a}$, $R^{16b}$, $R^{16c}$, $R^{16d}$, $R^{16e}$, $R^{16f}$, or $R^{16g}$ is a group represented by Formula W.

7. The organic semiconductor composition according to claim 1, further comprising:

a polymer compound as Component C.

8. The organic semiconductor composition according to claim 7, wherein a content of Component C is 0.01% to 2.0% by mass with respect to a total mass of the organic semiconductor composition.

9. The organic semiconductor composition according to claim 1 that has a viscosity of 2 to 50 mPa·s at 25° C.

10. The organic semiconductor composition according to claim 1, wherein a content of Component A is 0.2% to 5% by mass with respect to the total mass of the organic semiconductor composition.

11. The organic semiconductor composition according to claim 1 that is for ink jet printing and/or flexographic printing.

12. A method for manufacturing an organic semiconductor element, comprising:

an application step of applying the organic semiconductor composition according to claim 1 onto a substrate; and a removing step of removing at least a portion of Component B from the applied organic semiconductor composition.

13. The method for manufacturing an organic semiconductor element according to claim 12, wherein the application step is performed by ink jet printing or flexographic printing.

* * * * *